United States Patent
Suzuki et al.

(10) Patent No.: US 8,669,373 B2
(45) Date of Patent: Mar. 11, 2014

(54) CARBAZOLE DERIVATIVE AND METHOD FOR PRODUCING THE SAME

(75) Inventors: Hiroki Suzuki, Kanagawa (JP); Sachiko Kawakami, Kanagawa (JP); Nobuharu Ohsawa, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 45 days.

(21) Appl. No.: 12/560,903

(22) Filed: Sep. 16, 2009

(65) Prior Publication Data

US 2010/0076201 A1   Mar. 25, 2010

(30) Foreign Application Priority Data

Sep. 19, 2008   (JP) ................................ 2008-240299

(51) Int. Cl.
   *C07D 209/82* (2006.01)
(52) U.S. Cl.
   USPC ....................................................... 548/440
(58) Field of Classification Search
   USPC ....................................................... 548/440
   See application file for complete search history.

(56) References Cited

U.S. PATENT DOCUMENTS

| | | | |
|---|---|---|---|
| 5,811,834 A | 9/1998 | Tamano et al. |
| 6,482,986 B1 | 11/2002 | Boigegrain et al. |
| 6,617,051 B1 | 9/2003 | Higashi et al. |
| 6,713,566 B1 | 3/2004 | Marcuccio et al. |
| 6,815,094 B2 | 11/2004 | Lee et al. |
| 6,984,462 B2 | 1/2006 | Kim et al. |
| 7,132,456 B2 | 11/2006 | Gillig et al. |
| 7,161,185 B2 | 1/2007 | Yamazaki et al. |
| 7,252,894 B2 | 8/2007 | Yu et al. |
| 7,387,845 B2 | 6/2008 | Saitoh et al. |
| 7,541,097 B2 | 6/2009 | Seo et al. |
| 7,629,060 B2 | 12/2009 | Oshiyama et al. |
| 7,649,197 B2 | 1/2010 | Iwaki et al. |
| 7,651,787 B2 | 1/2010 | Seo et al. |
| 7,704,912 B2 | 4/2010 | Reetz et al. |
| 7,723,722 B2 | 5/2010 | Kawakami et al. |
| 7,745,988 B2 | 6/2010 | Sasaki et al. |
| 7,790,892 B2 | 9/2010 | Ikeda et al. |
| 7,919,773 B2 | 4/2011 | Kawakami et al. |
| 8,039,122 B2 | 10/2011 | Kawakami et al. |
| 8,298,687 B2 | 10/2012 | Kawakami et al. |
| 2003/0205696 A1 | 11/2003 | Thoms et al. |
| 2004/0086745 A1 | 5/2004 | Iwakuma et al. |
| 2004/0146746 A1 | 7/2004 | Lee et al. |
| 2004/0161632 A1 | 8/2004 | Seo et al. |
| 2004/0161633 A1 | 8/2004 | Seo et al. |
| 2005/0214565 A1 | 9/2005 | Ikeda et al. |
| 2005/0244670 A1 | 11/2005 | Saitoh et al. |
| 2006/0068221 A1 | 3/2006 | Saitoh et al. |
| 2006/0115680 A1* | 6/2006 | Hwang et al. .................. 428/690 |
| 2007/0049760 A1 | 3/2007 | Kawakami et al. |
| 2007/0075623 A1 | 4/2007 | Kawakami et al. |
| 2007/0075632 A1 | 4/2007 | Kawakami et al. |
| 2007/0106103 A1 | 5/2007 | Ikeda et al. |
| 2007/0215889 A1 | 9/2007 | Kawakami et al. |
| 2007/0247063 A1 | 10/2007 | Murase et al. |
| 2008/0107918 A1 | 5/2008 | Egawa et al. |
| 2008/0242871 A1 | 10/2008 | Kawakami et al. |
| 2009/0015140 A1 | 1/2009 | Kawakami et al. |

(Continued)

FOREIGN PATENT DOCUMENTS

| | | |
|---|---|---|
| CN | 1526689 A | 9/2004 |
| CN | 1837324 A | 9/2006 |

(Continued)

OTHER PUBLICATIONS

Kim et al. Mol. Cryst. Liq. Cryst. 2008, vol. 491, 133-144.*

(Continued)

*Primary Examiner* — Joseph Kosack
*Assistant Examiner* — Matthew Coughlin
(74) *Attorney, Agent, or Firm* — Husch Blackwell LLP

(57) ABSTRACT

To provide a method for producing a wide variety of carbazole derivatives which have a simple and uncomplicated process and in which variations in the yield, purity, etc. of a desired substance which are caused by an aryl group introduced is reduced as much as possible. A method for producing a carbazole derivative represented by General Formula (1) is provided, in which 9-[4-(10-phenyl-9-anthryl)phenyl]-9H-carbazole having an active site at the 3-position of the carbazole skeleton and an aromatic compound having an active site are coupled.

General Formula (1)

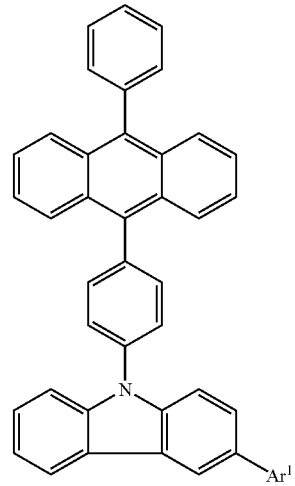

In the formula, $Ar^1$ represents an aryl group with 6 to 13 carbon atoms in a ring, and $Ar^1$ may have a substituent.

33 Claims, 34 Drawing Sheets

(56) References Cited

U.S. PATENT DOCUMENTS

| | | |
|---|---|---|
| 2009/0102360 A1 | 4/2009 | Kawakami et al. |
| 2010/0069647 A1* | 3/2010 | Suzuki et al. .................. 548/445 |
| 2010/0084645 A1 | 4/2010 | Iwaki et al. |
| 2010/0200847 A1 | 8/2010 | Kawakami et al. |
| 2013/0005067 A1 | 1/2013 | Kawakami et al. |

FOREIGN PATENT DOCUMENTS

| | | |
|---|---|---|
| CN | 101041633 A | 9/2007 |
| CN | 101184732 A | 5/2008 |
| CN | 101200634 A | 6/2008 |
| EP | 1 748 045 A1 | 1/2007 |
| EP | 1 829 871 A1 | 9/2007 |
| EP | 1 972 619 A1 | 9/2008 |
| EP | 2 479 814 A1 | 7/2012 |
| JP | 2003-31371 | 1/2003 |
| JP | 2003-167550 | 6/2003 |
| JP | 2003-229273 | 8/2003 |
| JP | 2003-238534 | 8/2003 |
| JP | 2004-87396 | 3/2004 |
| JP | 2004-91334 | 3/2004 |
| JP | 2004-210786 | 7/2004 |
| JP | 2007-39431 | 2/2007 |
| JP | 2007-131722 | 5/2007 |
| JP | 2008-81497 | 4/2008 |
| JP | 2008-266309 | 11/2008 |
| JP | 2010-168345 | 8/2010 |
| WO | WO 01/23353 A2 | 4/2001 |
| WO | WO 2004/020548 A1 | 3/2004 |
| WO | WO 2006/104221 A1 | 10/2006 |
| WO | WO 2006104221 A1 * | 10/2006 |
| WO | WO 2010/005066 A1 | 1/2010 |

OTHER PUBLICATIONS

Table of Contents of Mol. Cryst. Liq. Cryst. 2008, vol. 491, obtained from Ebsco Host on Aug. 4, 2010.*
Grisorio et al. Tetrahedron 2006, 62, 627-634.*
Carey and Sundberg, Advanced Organic Chemistry, Fifth Edition, 2007, p. 731.*
Benaglia et al. Tetrahedron Letters 1997, 38, 4737-4740.*
European Search Report re application No. EP 09169453.9, dated Nov. 3, 2009.
Pine, S.H., *Organic Chemistry*, McGraw-Hill International Editions, $5^{th}$ ed., 1987, cover pages & pp. 744-746.
Li, J.-H. et al, "CuI/DABCO-Catalyzed Cross-Coupling Reactions of Aryl Halides with Arylboronic Acids," Eur. J. Org. Chem., 2006, pp. 2063-2066.
Promarak, V. et al, "Synthesis and Properties of Stable Amorphous Hole-Transporting Molecules for Electroluminescent Devices," Tetrahedron Letters, vol. 47, No. 50, 2006, pp. 8949-8952.
International Search Report re application No. PCT/JP2006/306775, dated May 2, 2006.
Written Opinion re application No. PCT/JP2006/306775, dated May 2, 2006.
International Search Report re application No. PCT/JP2007/066706, dated Oct. 16, 2007.
Written Opinion re application No. PCT/JP2007/066706, dated Oct. 16, 2007.
European Search Report re application No. EP 08003826.8, dated Jul. 14, 2008.
European Search Report re application No. EP 06730723.1, dated Jan. 26, 2010.
Office Action re Chinese application No. CN 200680018801.4, dated Apr. 15, 2010 (with English translation).
Kurti, L. et al., Strategic Applications of Named Reactions in Organic Synthesis, Dec. 31, 2005, p. 448.
Chen, Y.-C. et al., "High Triplet Energy Polymer as Host for Electrophosphorescence with High Efficiency," Journal of the American Chemical Society, vol. 128, No. 26, 2006, pp. 8549-8558.
Office Action re Chinese Application No. CN 200910169057.3, dated Dec. 5, 2012 (with English translation).

* cited by examiner

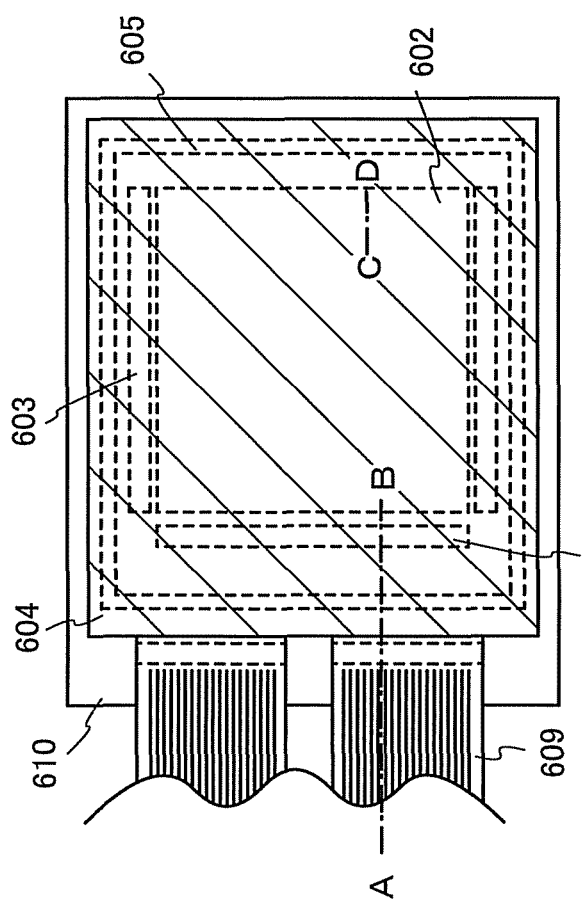
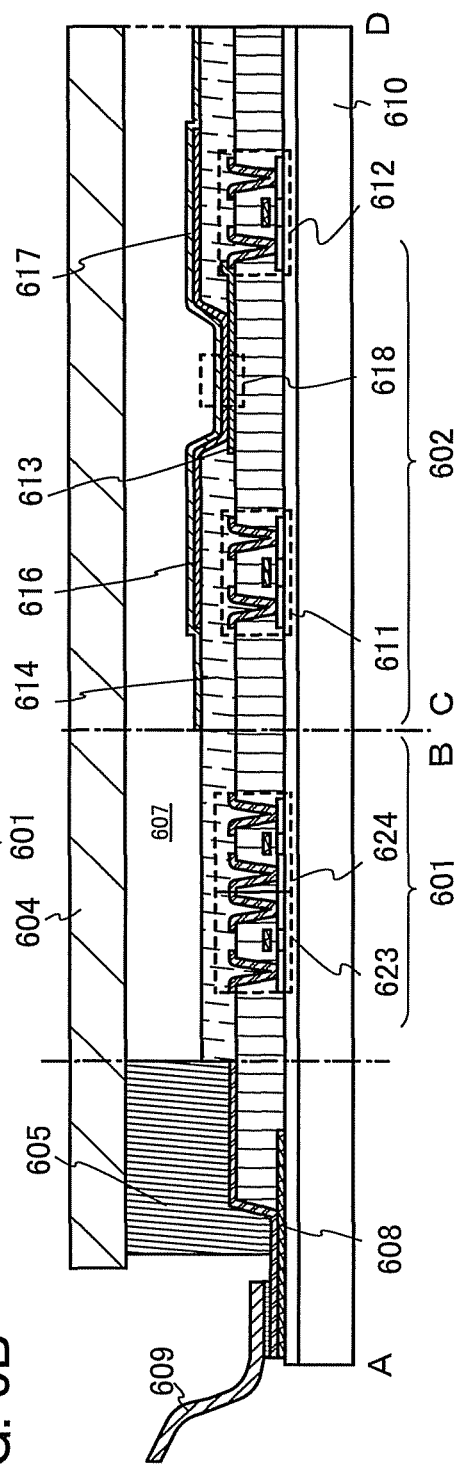
FIG. 5A
FIG. 5B

CARBAZOLE DERIVATIVE AND METHOD FOR PRODUCING THE SAME

BACKGROUND OF THE INVENTION

1. Field of the Invention

The present invention relates to a method for producing carbazole derivatives. Specifically, the present invention relates to a method for producing carbazole derivatives which each have a wide band gap and are good bipolar substances with a high electron-transport property and a high hole-transport property and suitable for use in light-emitting elements.

2. Description of the Related Art

A carbazole derivative represented by General Formula K1 below which covers carbazole derivatives that are desired substances of an embodiment of the present invention and a carbazole derivative represented by General Formula (1) below which is a desired substance of an embodiment of the present invention are well-known substances. It is also well known that each substance has a large band gap, can emit light of an extremely short wavelength, and can exhibit blue light emission with high color purity (see Patent Documents 1 and 2). Further, high electrochemical stability of these derivatives and also methods for producing them are naturally known (see Patent Documents 1 and 2).

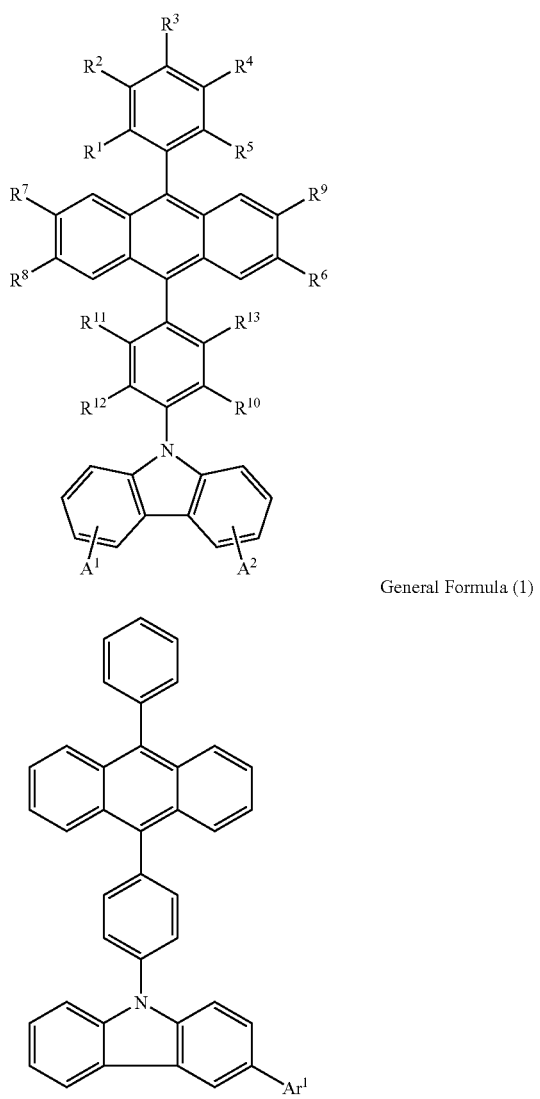

General Formula K1

General Formula (1)

As the known method for producing the derivative represented by General Formula (1), there are two methods, which are described in Patent Documents 1 and 2. The production method described in Patent Document 1 is referred to as a first known method. The first known method will be detailed hereinbelow and consists of three steps: Reaction Formulae (K-1), (K-2), and (K-3).

In accordance with the first known method, 9H-carbazole (Compound K1) is first halogenated to give a carbazole derivative (Compound K2) (Reaction Formula (K-1)). In Reaction Formula (K-1), $X^2$ represents a halogen, preferably iodine or bromine. When bromination is carried out in Reaction Formula (K-1), examples of brominating agents that can be used include bromine, N-bromosuccinimide, and the like. Examples of solvents that can be used in this case include halogen-based solvents such as chloroform and carbon tetrachloride. When N-bromosuccinimide is used as the brominating agent, ethyl acetate, tetrahydrofuran, dimethylformamide, acetic acid, water, or the like can be used as the solvent.

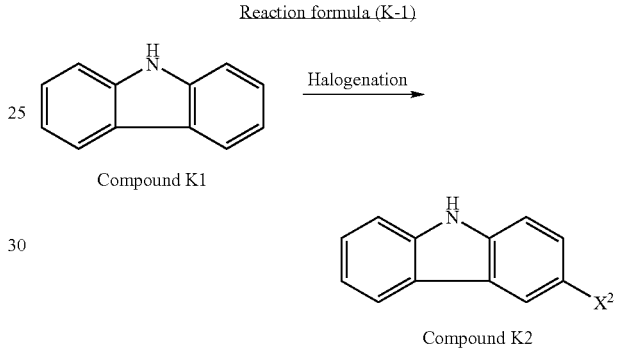

Reaction formula (K-1)

Compound K1

Compound K2

When iodination is carried out in Reaction Formula (K-1), examples of iodinating agents that can be used include N-iodosuccinimide, 1,3-diiodo-5,5-dimethylimidazolidine-2,4-dione (abbreviation: DIH), 2,4,6,8-tetraiodo-2,4,6,8-tetraazabicyclo[3,3,0]octane-3,7-dione, 2-iodo-2,4,6,8-tetraazabicyclo[3,3,0]octane-3,7-dione, and the like.

Further, examples of solvents that can be used alone or in combination for iodination with such an iodinating agent include aromatic hydrocarbons such as benzene, toluene, and xylene; ethers such as 1,2-dimethoxyethane, diethyl ether, methyl-t-butyl ether, tetrahydrofuran, and dioxane; saturated hydrocarbons such as pentane, hexane, heptane, octane, and cyclohexane; halogens such as dichloromethane, chloroform, carbon tetrachloride, 1,2-dichloroethane, and 1,1,1-trichloroethane; nitriles such as acetonitrile and benzonitrile; esters such as ethyl acetate, methyl acetate, and butyl acetate; acetic acid (glacial acetic acid); water; and the like. When water is used, water is preferably mixed with an organic solvent. Furthermore, in this reaction, acid such as sulfuric acid or acetic acid is preferably used at the same time.

Next, the carbazole derivative obtained (Compound K2) and aryl boronic acid [Compound K3 (corresponding to "Compound 3" of the present invention)] are coupled according to a Suzuki-Miyaura reaction using a palladium catalyst, whereby 3-aryl-9H-carbazole (Compound K4) is obtained (Reaction Formula (K-2)). In Reaction Formula (K-2), $X^2$ represents a halogen, preferably iodine or bromine. Alternatively, in Reaction Formula (K-2), a compound in which $X^2$ is a triflate group may be used. Note that an organoboron compound represented by Compound K3 is referred to as aryl boronic acid when $R^{101}$ and $R^{102}$ independently represent hydrogen.

Reaction Formula (K-2)

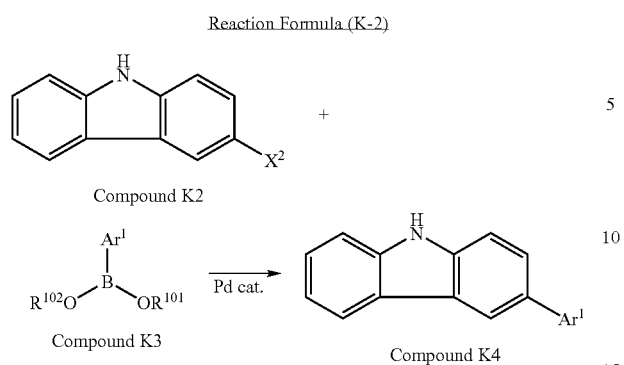

In Reaction Formula (K-2), $Ar^1$ represents an aryl group with 6 to 13 carbon atoms which may have a substituent. Examples of palladium catalysts that can be used in this reaction formula include palladium(II) acetate, tetrakis(triphenylphosphine)palladium(0), and the like. Examples of ligands of the palladium catalyst which can be used in Reaction Formula (K-2) include tri(ortho-tolyl)phosphine, triphenylphosphine, tricyclohexylphosphine, and the like.

Examples of bases that can be used in Reaction Formula (K-2) include organic bases such as sodium tert-butoxide, inorganic bases such as potassium carbonate, and the like. Examples of solvents that can be used in Reaction Formula (K-2) include a mixed solvent of toluene and water, a mixed solvent of toluene, an alcohol such as ethanol, and water, a mixed solvent of xylene and water, a mixed solvent of xylene, an alcohol such as ethanol, and water, a mixed solvent of benzene and water, a mixed solvent of benzene, an alcohol such as ethanol, and water, a mixed solvent of an ether such as ethyleneglycoldimethylether and water, and the like. Note that use of a mixed solvent of toluene and water or a mixed solvent of toluene, ethanol, and water is more preferable.

In Reaction Formula (K-3) which is the last reaction step of the first known method, an anthracene derivative (Compound K5) and the carbazole derivative (Compound K4) are coupled according to a Hartwig-Buchwald reaction using a palladium catalyst or an Ullmann reaction using copper or a copper compound. Thus, a carbazole derivative represented by General Formula (1) which is the same desired substance as a production method of an embodiment of the present invention is obtained.

Reaction Formula (K-3)

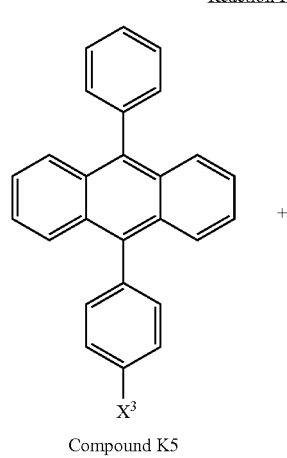

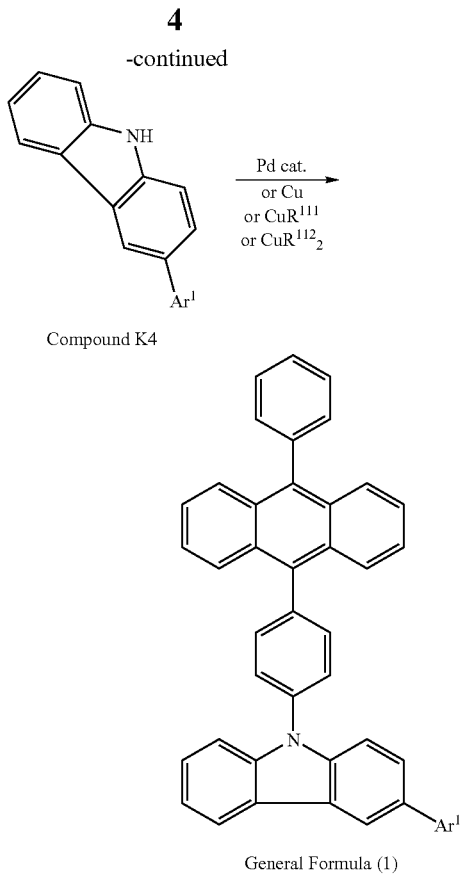

In Reaction Formula (K-3), $X^3$ represents a halogen or a triflate group; when $X^3$ is a halogen, it is preferably iodine, bromine, or chlorine. In this reaction formula, $Ar^1$ represents an aryl group with 6 to 13 carbon atoms which may have a substituent. Examples of palladium catalysts that can be used for a Hartwig-Buchwald reaction in Reaction Formula (K-3) include bis(dibenzylideneacetone)palladium(0), palladium (II) acetate, and the like.

Examples of ligands of the palladium catalyst which can be used in Reaction Formula (K-3) include tri(tert-butyl)phosphine, tri(n-hexyl)phosphine, tricyclohexylphosphine, and the like. Examples of bases that can be used include organic bases such as sodium tert-butoxide, inorganic bases such as potassium carbonate, and the like. Further, examples of solvents that can be used include toluene, xylene, benzene, tetrahydrofuran, and the like.

In Reaction Formula (K-3), an Ullmann reaction can be carried out instead of a Hartwig-Buchwald reaction, as described above, in which case copper or a copper compound is used instead of a palladium catalyst. In this case, $R^{111}$ and $R^{112}$ independently represent a halogen, an acetyl group, or the like; as the halogen, there are chlorine, bromine, and iodine. Further, use of copper(I) iodide in which $R^{111}$ is iodine or copper(II) acetate in which $R^{112}$ is an acetyl group is preferable. As the base that can be used in this case, an inorganic base such as potassium carbonate is given.

Further, examples of solvents that can be used in the above reaction include 1,3-dimethyl-3,4,5,6-tetrahydro-2(1H)pyrimidinone (DMPU), toluene, xylene, benzene, and the like. In an Ullmann reaction, since a reaction temperature of 100° C. or more enables the desired substance in a shorter time and a higher yield, DMPU or xylene, which has a high boiling point, is preferably used. In addition, since the reaction temperature is more preferably 150° C. or more, use of DMPU is preferred.

The first known method is as described above. A second known method is a production method described in Patent Document 2 and consists of three steps: Reaction Formulae (K-4), (K-5), and (K-6), as specifically described hereinbelow. Note that since Compound K4 which is a starting material in Reaction Formula (K-4) is obtained through two reaction steps: Reaction Formulae (K-1) and (K-2), the second known method includes another two reaction steps in a strict sense.

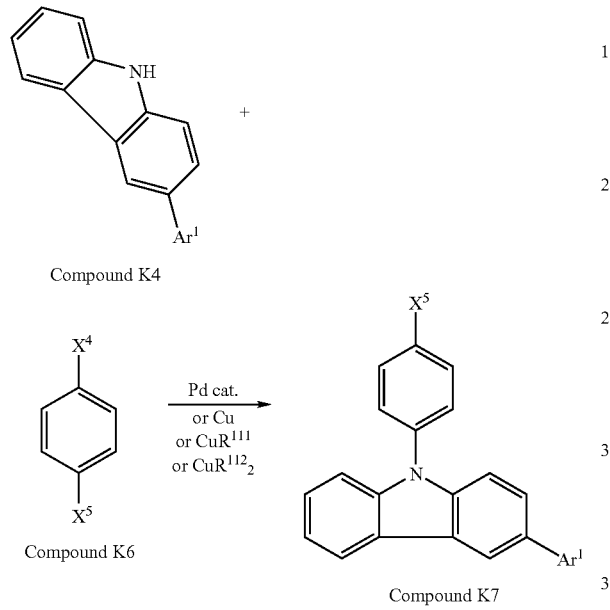

The carbazole derivative synthesized by the first known method (Compound K4) and para-dihalogenated benzene (Compound K6) are coupled according to a Hartwig-Buchwald reaction using a palladium catalyst or an Ullmann reaction using copper or a copper compound, whereby a carbazole derivative (Compound K7) can be obtained (Reaction Formula (K-4)). In Reaction Formula (K-4), $X^4$ and $X^5$ independently represent a halogen or a triflate group; when $X^4$ and $X^5$ independently represent a halogen, it is preferably iodine, bromine, or chlorine. In addition, $X^4$ and $X^5$ may be the same or different from each other. In Reaction Formula (K-4), $Ar^1$ represents an aryl group with 6 to 13 carbon atoms which may have a substituent.

For a Hartwig-Buchwald reaction in Reaction Formula (K-4), examples of palladium catalysts that can be used include bis(dibenzylideneacetone)palladium(0), palladium (II) acetate, and the like. Examples of ligands of the palladium catalyst which can be used include tri(tert-butyl)phosphine, tri(n-hexyl)phosphine, tricyclohexylphosphine, and the like. Examples of bases that can be used include organic bases such as sodium tert-butoxide, inorganic bases such as potassium carbonate, and the like. Further, examples of solvents that can be used include toluene, xylene, benzene, tetrahydrofuran, and the like.

In Reaction Formula (K-4), an Ullmann reaction can be performed instead of a Hartwig-Buchwald reaction, as described above, in which case copper or a copper compound is used instead of a palladium catalyst. In this case, $R^{111}$ and $R^{112}$ independently represent a halogen, an acetyl group, or the like; as the halogen, there are chlorine, bromine, or iodine.

Further, use of copper(I) iodide in which $R^{111}$ is iodine or copper(II) acetate in which $R^{112}$ is an acetyl group is preferable. Instead of a copper compound, copper can alternatively be used.

Furthermore, as a base that can be used in the above reaction formula, an inorganic base such as potassium carbonate is given. Examples of solvents that can be used include 1,3-dimethyl-3,4,5,6-tetrahydro-2(1H)pyrimidinone (DMPU), toluene, xylene, benzene, and the like. In an Ullmann reaction, since a reaction temperature of 100° C. or more enables the desired substance in a shorter time and a higher yield, DMPU or xylene, which has a high boiling point, is preferably used. In addition, since the reaction temperature is more preferably 150° C. or more, use of DMPU is preferred.

Next, the carbazole derivative obtained (Compound K7) undergoes boron oxidation using an alkyl lithium reagent and a boron reagent, whereby a boronic acid body (Compound K8) of the carbazole derivative is obtained (Reaction Formula (K-5)). In Reaction Formula (K-5), $X^5$ represents a halogen or a triflate group; as the halogen, it is preferably iodine, bromine, or chlorine, and $Ar^1$ represents an aryl group with 6 to 13 carbon atoms which may have a substituent. Further, the boronic acid of Compound K8 may be used in the subsequent reaction after being protected with ethylene glycol or pinacol.

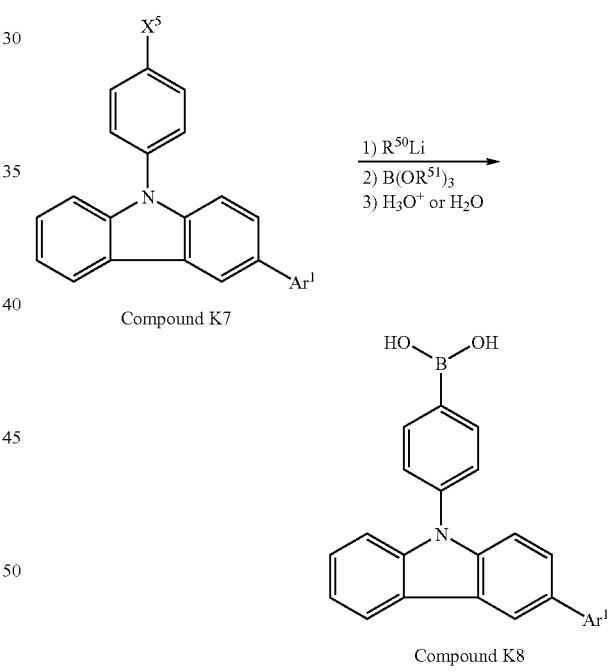

In Reaction Formula (K-5), $R^{50}$ represents an alkyl group with 1 to 6 carbon atoms, and $R^{51}$ represents an alkyl group with 1 to 6 carbon atoms. Examples of solvents that can be used include ether-based solvents such as diethyl ether, tetrahydrofuran (THF), and cyclopentyl methyl ether. Further, examples of alkyl lithium reagents include n-butyllithium in which $R^{50}$ is an n-butyl group, t-butyllithium in which $R^{50}$ is a t-butyl group, and methyllithium in which $R^{50}$ is a methyl group, and the like. Furthermore, examples of boron reagents include trimethyl borate in which $R^{51}$ is a methyl group, triisopropyl borate in which $R^{51}$ is an isopropyl group, and the like.

Lastly, the boronic acid body (Compound K8) of the carbazole derivative and an anthracene derivative (Compound K9) are coupled according to a Suzuki-Miyaura coupling reaction using a palladium catalyst, whereby the desired substance represented by General Formula (1) is obtained (Reaction Formula (K-6)). In Reaction Formula (K-6), $X^6$ represents a halogen or a triflate group; when $X^6$ is a halogen, it is preferably iodine, bromine, or chlorine.

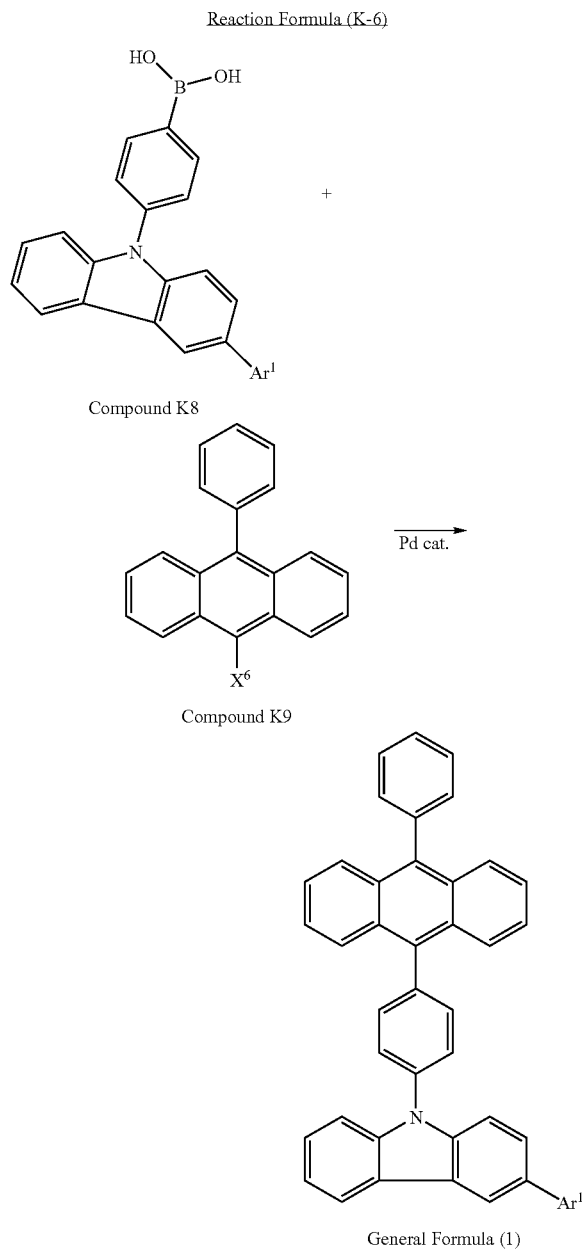

In Reaction Formula (K-6), $Ar^1$ represents an aryl group with 6 to 13 carbon atoms which may have a substituent. Examples of palladium catalysts that can be used include palladium(II) acetate, tetrakis(triphenylphosphine)palladium (0), and the like. Examples of ligands of the palladium catalyst which can be used in this case include tri(ortho-tolyl) phosphine, triphenylphosphine, tricyclohexylphosphine, and the like. Examples of bases that can be used in this reaction formula include organic bases such as sodium tert-butoxide, inorganic bases such as potassium carbonate, and the like Further, examples of solvents that can be used in the above reaction include a mixed solvent of toluene and water, a mixed solvent of toluene, an alcohol such as ethanol, and water, a mixed solvent of xylene and water, a mixed solvent of xylene, an alcohol such as ethanol, and water, a mixed solvent of benzene and water, a mixed solvent of benzene, an alcohol such as ethanol, and water, a mixed solvent of an ether such as ethyleneglycoldimethylether and water, and the like. Further, use of a mixed solvent of toluene and water or a mixed solvent of toluene, ethanol, and water is more preferable. Note that instead of Compound K8, an organoboron compound obtained by protecting the boronic acid of Compound K8 with ethylene glycol or pinacol may be used.

As described above, a compound represented by General Formula (1) which is a desired substance of a production method of the present invention is a known substance, and the two methods for producing the compound is also known. Further, the compound represented by General Formula (1) has a structure in which an anthracene skeleton and a carbazole skeleton are bonded and an aryl group is bonded to the 3-position of the carbazole skeleton.

In each known production method, the formation processes is not simple due to a number of reaction steps up to formation of a desired substance. Further, any of a variety of aryl groups can be applied to an aryl group ($Ar^1$) in a derivative represented by General Formula (1) which is a desired substance of both a production method of the present invention and the known production methods, and a wide variety of carbazole derivatives can be produced by these methods. However, since the known production methods involve, before an anthracene skeleton and a carbazole skeleton are bonded, the introduction of the aryl group that is to be bonded to the 3-position of the carbazole skeleton, it can be said that such methods are not effective in producing a wide variety of carbazole derivatives.

In other words, in the known production methods, because of the introduction of an aryl group to the 3-position of the carbazole skeleton before the anthracene skeleton and the carbazole skeleton are bonded, the bonding reaction of the both skeletons occurs after the introduction. Accordingly, in the first known method, there is a problem in that what kind of aryl group is introduced affects the reaction in which the aryl group is introduced and the following reaction in which the both skeletons are bonded, so that the yield, purity, etc. of a desired substance varies depending on the aryl group introduced.

Moreover, in the second known method, since Compound K4 which is the starting material in Reaction Formula (K-4) which is the first step is carbazole in which an aryl group is introduced, the carbazole undergoes three steps of reactions: Reaction Formulae (K-4), (K-5), and (K-6). Therefore, in each step, the aryl group substituted affects progression of the reaction. Accordingly, the yield, purity, etc. of a desired substance varies depending on the aryl group introduced to the starting material.

REFERENCES

Patent Documents

[Patent Document 1] Japanese Published Patent Application No. 2007-39431
[Patent Document 2] Japanese Published Patent Application No. 2008-81497

SUMMARY OF THE INVENTION

As described above, in the above-described known production methods, the formation process is not simple, and what kind of aryl group is introduced significantly affects the yield, purity, etc. of a desired substance in production of a wide variety of carbazole derivatives. Through detailed studies, the present inventors have found a novel method for producing carbazole derivatives in which such a problem is reduced. Specifically, an object of the present invention is to provide a method for producing a wide variety of carbazole derivatives which have a simple and uncomplicated process and in which variations in the yield, purity, etc. of a desired substance which depend on an aryl group introduced are reduced as much as possible.

An embodiment of the present invention provides a method for producing a carbazole derivative represented by General Formula (1), in which 9-[4-(10-phenyl-9-anthryl)phenyl]-9H-carbazole having an active site at the 3-position of the carbazole skeleton and an aromatic compound having an active site are coupled. Also, an embodiment of the present invention includes 9-[4-(10-phenyl-9-anthryl)phenyl]-9H-carbazole having an active site at the 3-position of the carbazole skeleton, and a production method thereof.

General Formula (1)

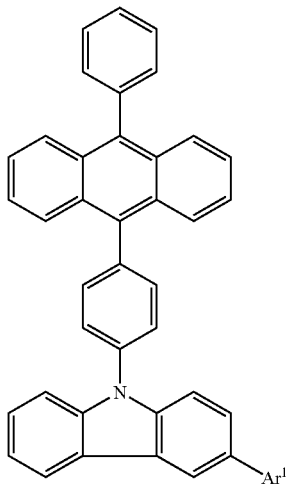

In the formula, $Ar^1$ represents an aryl group with 6 to 13 carbon atoms in a ring. In addition, $Ar^1$ may have a substituent.

Further, a preferable embodiment of the present invention is a method for producing a carbazole derivative represented by General Formula (1a), in which 9-[4-(10-phenyl-9-anthryl)phenyl]-9H-carbazole having an active site at the 3-position of the carbazole skeleton and an aromatic compound having an active site which is represented by Compound (A1) are coupled using a metal catalyst.

Compound (A1)

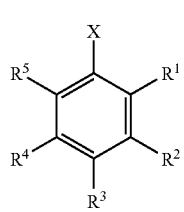

In the formula, X represents an active site, and $R^1$ to $R^5$ independently represent hydrogen, an alkyl group with 1 to 4 carbon atoms, or an aryl group with 6 to 13 carbon atoms in a ring which may have a substituent.

General Formula (1a)

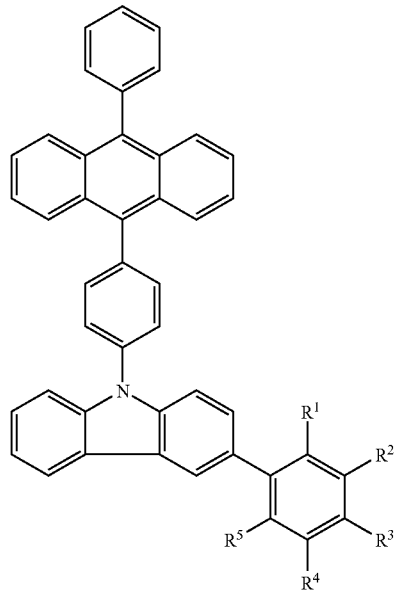

In the formula, $R^1$ to $R^5$ independently represent hydrogen, an alkyl group with 1 to 4 carbon atoms, or an aryl group with 6 to 13 carbon atoms in a ring which may have a substituent.

Further, a more preferable embodiment of the present invention is a method for producing a carbazole derivative represented by General Formula (1b), in which 9-[4-(10-phenyl-9-anthryl)phenyl]-9H-carbazole having an active site at the 3-position of the carbazole skeleton and an organoboron compound which is represented by Compound (A2) are coupled using a palladium catalyst.

Compound (A2)

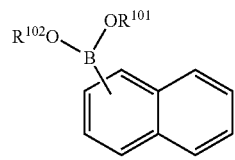

In the formula, $R^{101}$ and $R^{102}$ independently represent hydrogen or an alkyl group having 1 to 6 carbon atoms and may be bonded to form a ring structure. Note that an organoboron compound represented by Compound (A2) is referred to as aryl boronic acid when $R^{101}$ and $R^{102}$ independently represent hydrogen in General Formula (1b).

General Formula (1b)

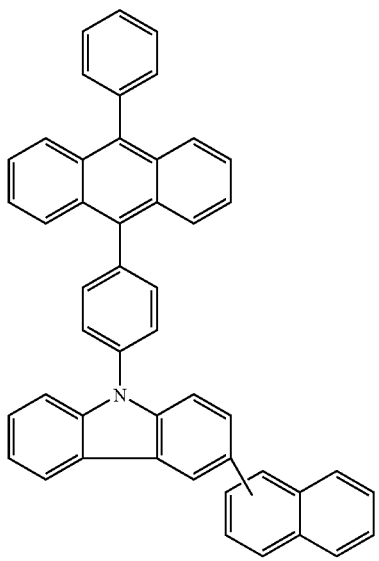

According to the present invention, the aryl group (Ar¹) can have different variations through one reaction step, whereby a wide variety of carbazole derivatives can be produced. Thus, the present invention provides an excellent method in which a variety of carbazole derivatives are produced by a simple and uncomplicated process. Further, unlike known methods, the present invention does not require two or more reaction steps after a functional group of the aryl group (Ar¹) having different variations is introduced to the 3-position of the carbazole skeleton in production of a variety of carbazole derivatives. Accordingly, a reduction in the yield, purity, etc. of a desired substance which is caused by the aryl group introduced to the carbazole group can be suppressed as much as possible.

BRIEF DESCRIPTION OF THE DRAWINGS

FIGS. 5A and 5B illustrate a light-emitting device according to an embodiment of the present invention.

DETAILED DESCRIPTION OF THE INVENTION

Figure 1A:
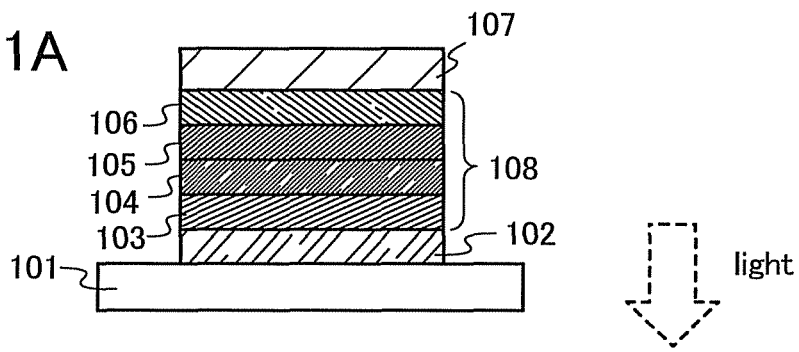
FIGS. 1A to 1C each illustrate a light-emitting element according to an embodiment of the present invention.

Hereinafter, various embodiments of the present invention which include the best mode for implementing the present invention will be described in detail with reference to the accompanying drawings as necessary. Note that the present invention is not limited to the description below. Thus, it is easily understood by those skilled in the art that the modes and details of the present invention can be easily modified in various ways without departing from the spirit and scope of the present invention. Further, applications of the substances that are desired substances produced by a production method of the present invention, etc. will also be detailed below.

An embodiment of the present invention is a method for producing a carbazole derivative represented by General Formula (1), in which 9-[4-(10-phenyl-9-anthryl)phenyl]-9H-carbazole having an active site at the 3-position of the carbazole skeleton and an aromatic compound having an active site are coupled, as described above. Note that the term aromatic compound in this specification does not cover a heterocyclic compound.

An embodiment of the present invention is a method for producing a carbazole derivative represented by the above General Formula (1), in which 9-[4-(10-phenyl-9-anthryl)phenyl]-9H-carbazole having an active site at the 3-position of the carbazole skeleton and an aromatic compound having an active site are coupled, as described above. A step of forming 9-[4-(10-phenyl-9-anthryl)phenyl]-9H-carbazole having an active site at the 3-position which is an early step of the production method and the subsequent coupling step are illustrated in the following Reaction Formulae 1 and 2.

Reaction Formula 1

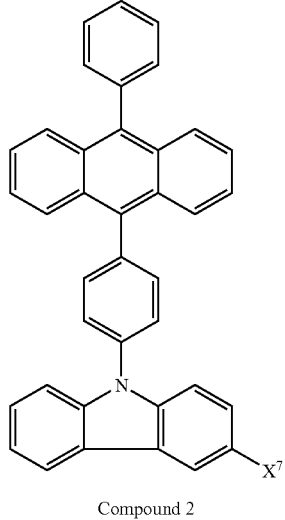

Compound 1

Reaction Formula 2

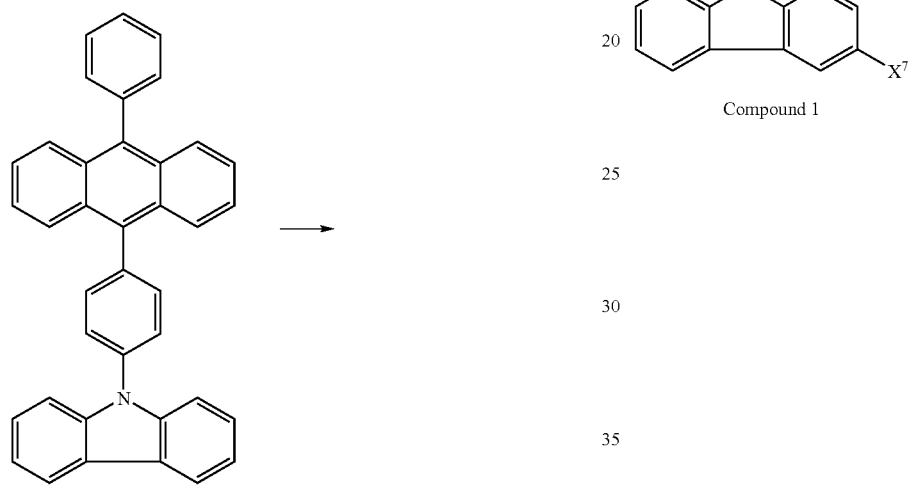

Note that $X^8$ of Compound 3 represents an active site. Examples of the active site $X^8$ include halogens, boronic acid, organoboron compounds, organotin compounds, trifluoromethanesulfonate (triflate), Grignard reagents, organic mercury compounds, thiocyanate, organozinc compounds, organoaluminum compounds, organozirconium compounds, and the like. In General Formula (1), $Ar^1$ represents an aryl group with 6 to 13 carbon atoms in a ring. In addition, $Ar^1$ may have a substituent.

Hereinafter, the substituent $Ar^1$ which is to be introduced to a carbazole derivative represented by General Formula (1) will be further detailed. As examples of the aryl group of this $Ar^1$, there are a phenyl group, a naphthyl group, a fluorenyl group, and the like. When the aryl group has a substituent, as examples of the substituent, there are an alkyl group with 1 to 4 carbon atoms, a haloalkyl group with one carbon atom, a phenyl group, a naphthyl group, a fluorenyl group, and the like. Note that when $Ar^1$ has a substituent, substituents may be Note that $X^7$ of Compound 2 represents an active site. Examples of the active site $X^7$ include halogens, boronic acid, organoboron compounds, organotin compounds, trifluoromethanesulfonate (triflate), Grignard reagents, organic mercury compounds, thiocyanate, organozinc compounds, organoaluminum compounds, organozirconium compounds, and the like.

bonded to form a ring, in which case a spiro ring is included in the ring structure. Further, carbon atoms in the spiro ring of this case are in a ring.

As specific structures of the aryl group of Ar$^1$, there are substituents (S-1) to (S-24) below, and the like, for example. Among these substituents, the substituent (S-1) is a specific example where the aryl group is a phenyl group, and the substituents (S-4) to (S-16) are each a specific example where the phenyl group further has a substituent. Further, the substituents (S-2) and (S-3) are each a specific example where the aryl group is a naphthyl group. The substituents (S-17) to (S-19) are each a specific example where the aryl group is a fluorenyl group and has a substituent. Note that the substituent (S-18) is a specific example where the substituents are bonded to form a spiro ring.

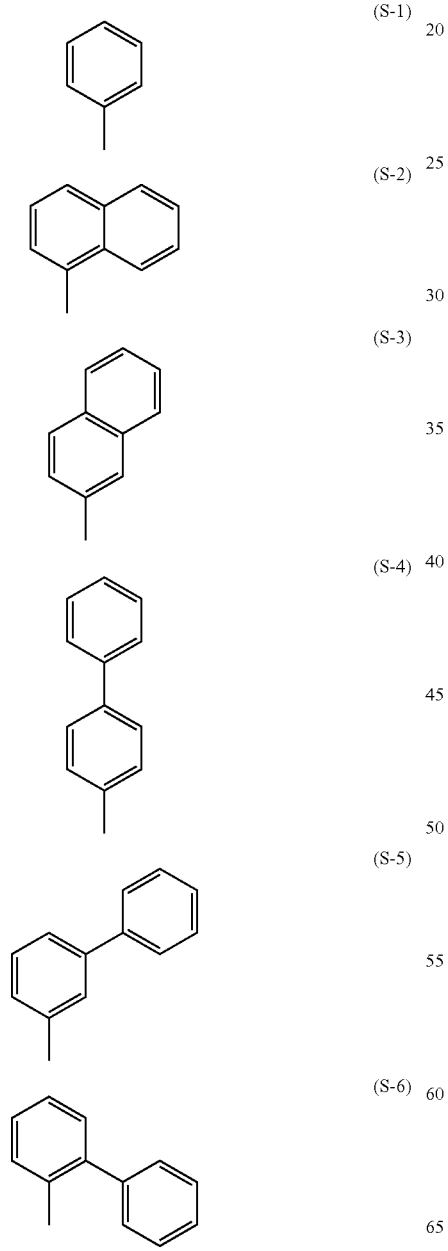
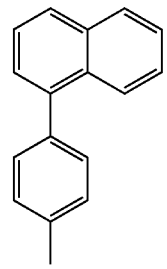
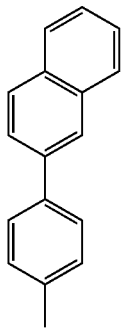
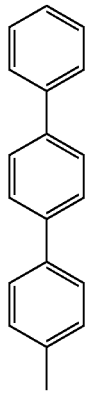
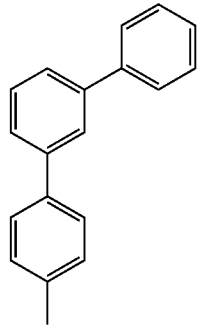
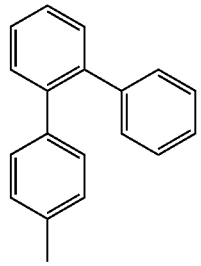

(S-12) 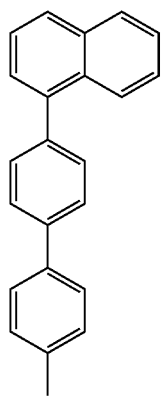
(S-13)
(S-14)
(S-15)
(S-16) 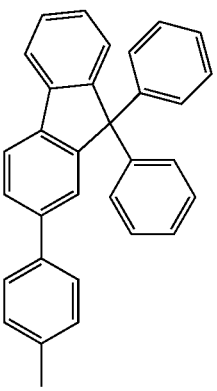
(S-17) 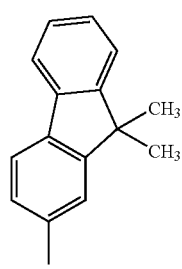
(S-18) 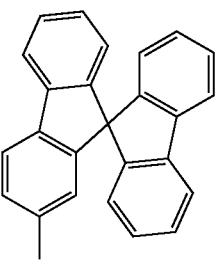
(S-19) 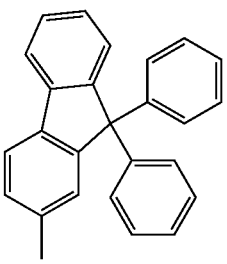
(S-20) 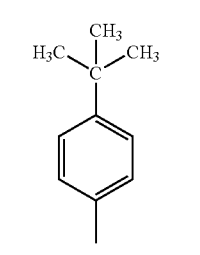
(S-21) 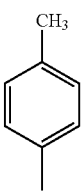

-continued

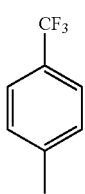
(S-22)

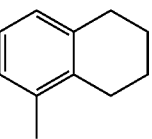
(S-23)

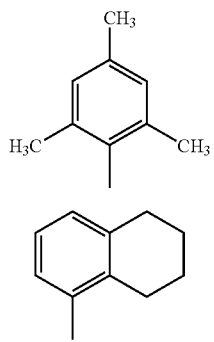
(S-24)

A method for producing carbazole derivatives according to an embodiment of the present invention is a method for producing a carbazole derivative represented by General Formula (1) which is a desired substance, in which a coupling reaction of 9-[4-(10-phenyl-9-anthryl)phenyl]-9H-carbazole having an active site at the 3-position of the carbazole skeleton and an aryl group having an active site is carried out as illustrated in Reaction Formula 2 using a metal catalyst such as a palladium catalyst or a nickel catalyst. As the coupling reaction, Suzuki-Miyaura coupling, Migita-Kosugi-Stille coupling, Kumada-Tamao coupling, Negishi coupling, or the like can be used. The metal catalyst may be a metal such as copper or iron or a metal compound such as copper(I) iodide.

Further, a preferable embodiment of the present invention is the following method, i.e., the method for producing a carbazole derivative represented by the above-described General Formula (1a), in which 9-[4-(10-phenyl-9-anthryl)phenyl]-9H-carbazole having an active site at the 3-position of the carbazole skeleton and an aryl group having an active site which is represented by Compound (A1) are coupled using a metal catalyst. As the metal catalyst used in the reaction, a metal catalyst such as a palladium catalyst or a nickel catalyst can be given.

In addition, the metal catalyst may be a metal such as copper or iron or a metal compound such as copper(I) iodide.

Further, a more preferable embodiment of the present invention is the following method, i.e., the method for producing a carbazole derivative represented by the above-described General Formula (1b), in which 9-[4-(10-phenyl-9-anthryl)phenyl]-9H-carbazole having an active site at the 3-position of the carbazole skeleton and an organoboron compound which is represented by Compound (A2) are coupled using a palladium catalyst. Note that an organoboron compound represented by Compound (A2) is referred to as aryl boronic acid when $R^{101}$ and $R^{102}$ independently represent hydrogen.

Compounds produced by a production method of the present invention are specifically represented by Structural Formulae 1 to 31, for example. The compound names of some of those compounds are 3-phenyl-9-[4-(10-phenyl-9-anthryl)phenyl]-9H-carbazole (abbreviation: CzPAP, the compound represented by Structural Formula 1) and 3-[4-(1-naphthyl)phenyl]-9-[4-(10-phenyl-9-anthryl)phenyl]-9H-carbazole (abbreviation: CzPAαNP, the compound represented by Structural Formula 2).

Structual Formula 1

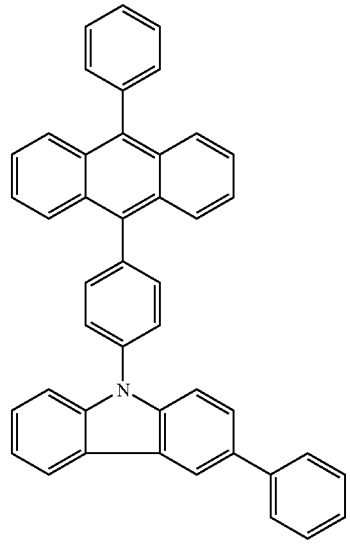

Structual Formula 2

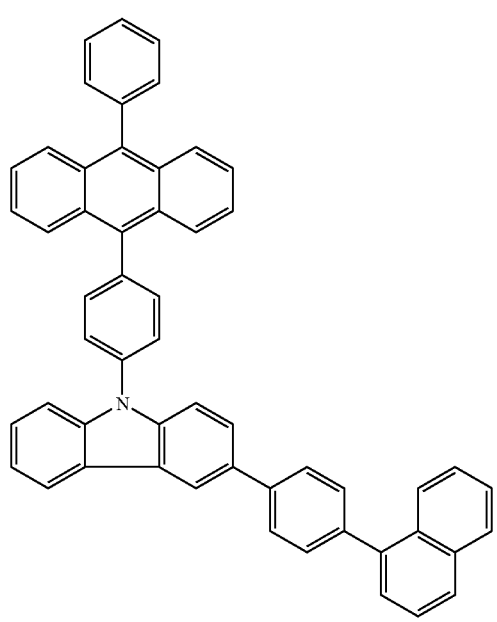

Structual Formula 3
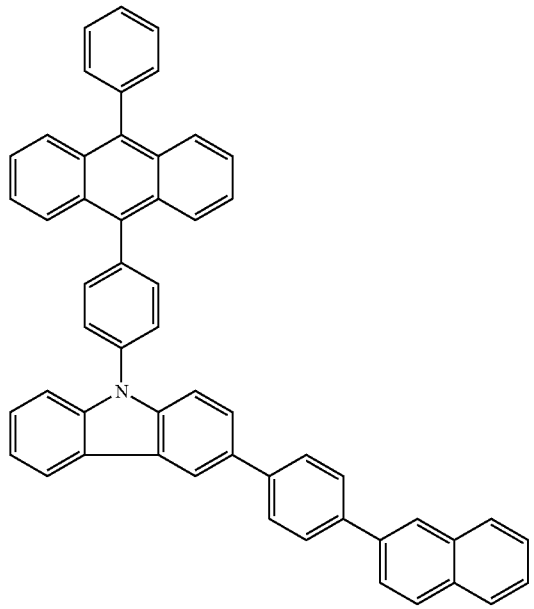
Structual Formula 4
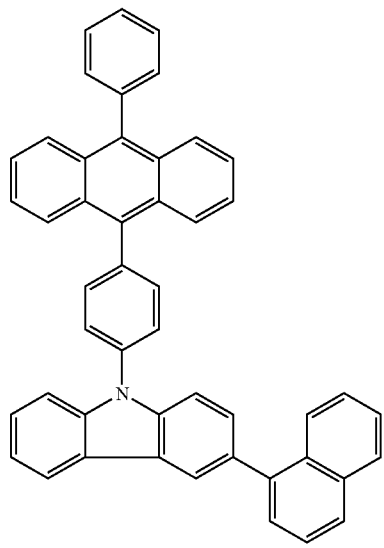
Structual Formula 5
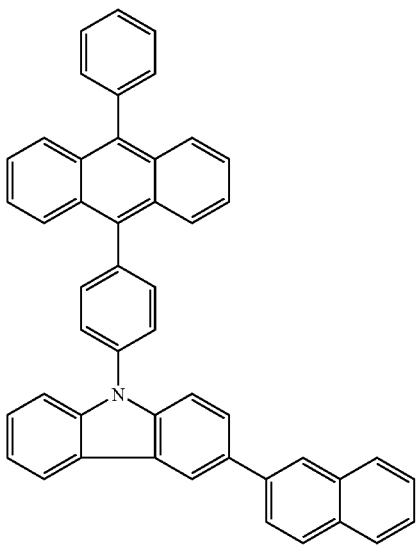
Structual Formula 6
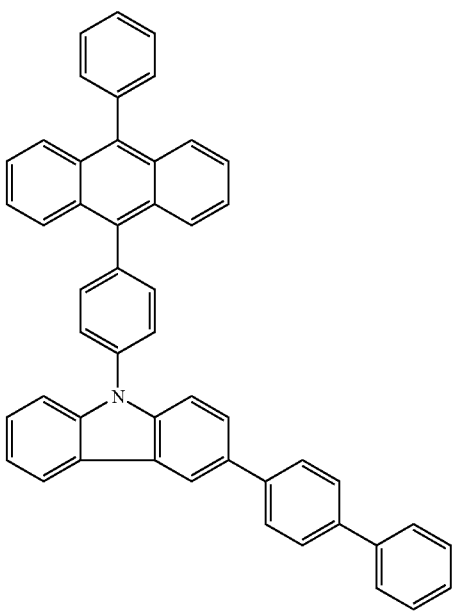

Structual Formula 7
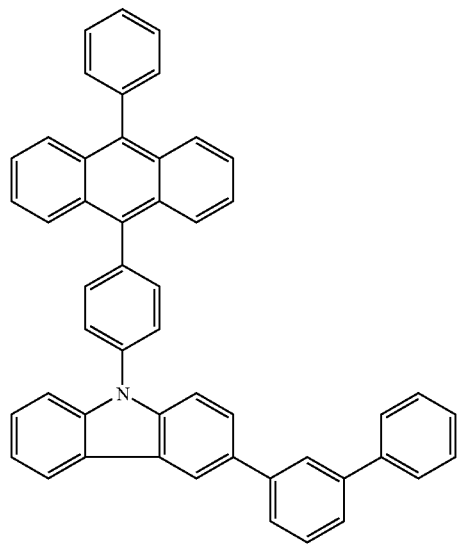
Structual Formula 8
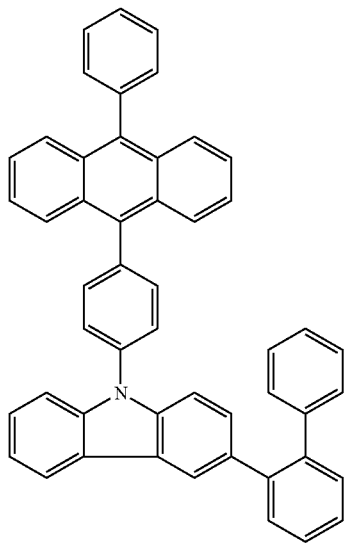
Structual Formula 9
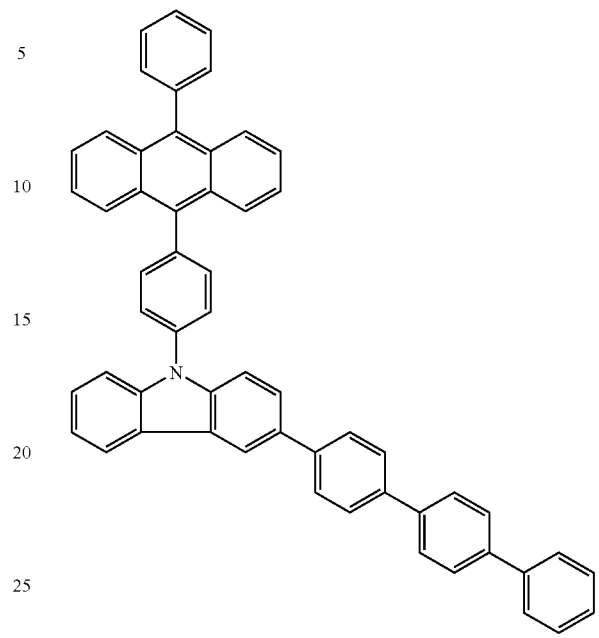
Structual Formula 10
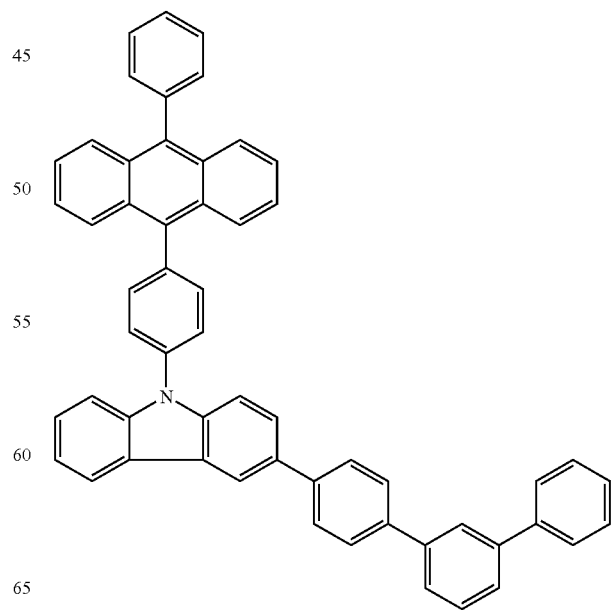

Structual Formula 11
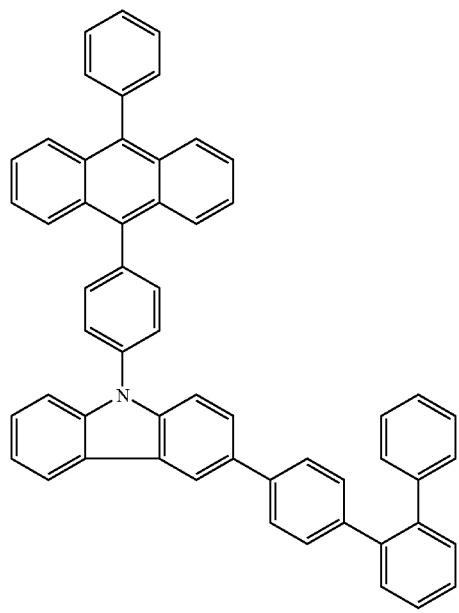
Structual Formula 13
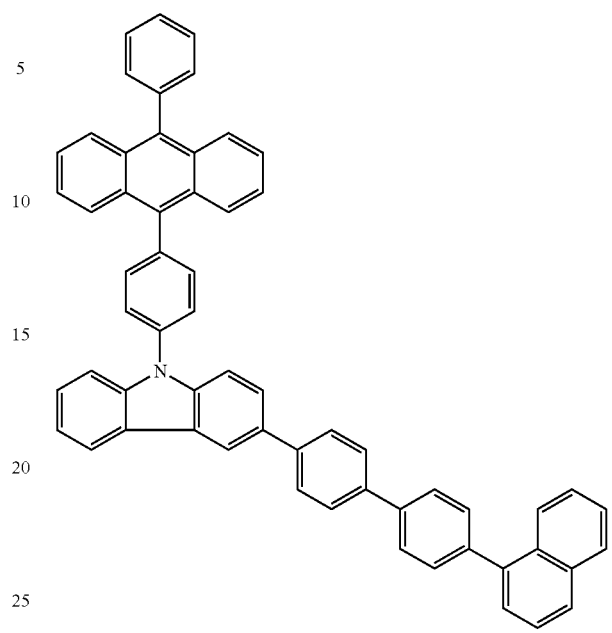
Structual Formula 12
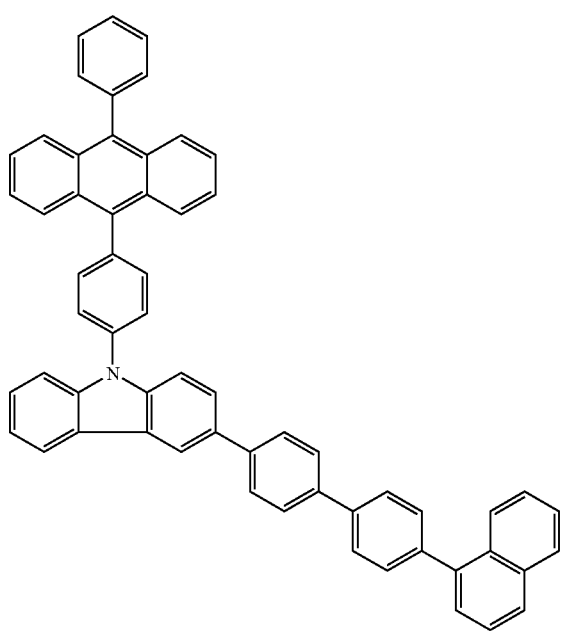
Structual Formula 14
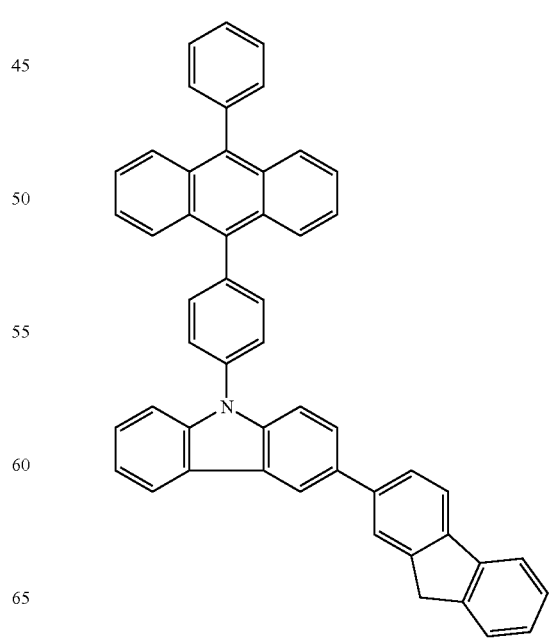

Structual Formula 15
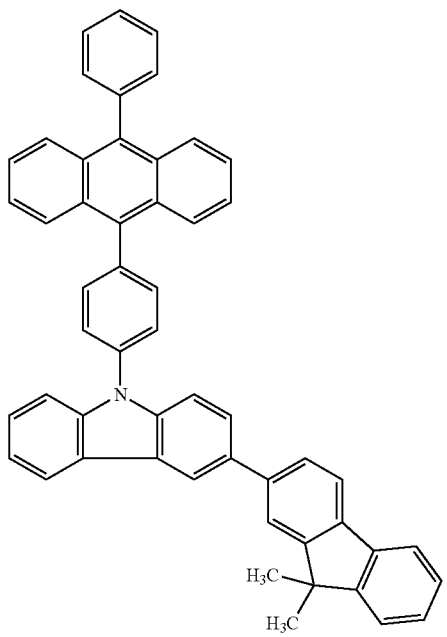
Structual Formula 16
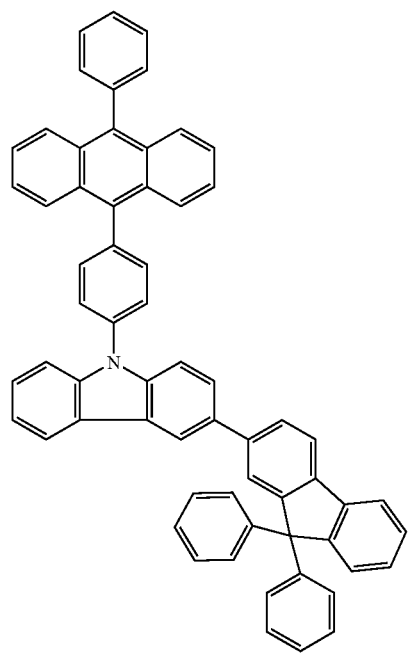
Structual Formula 17
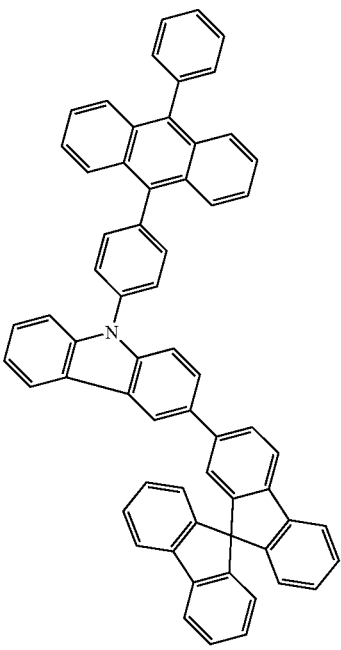
Structual Formula 18
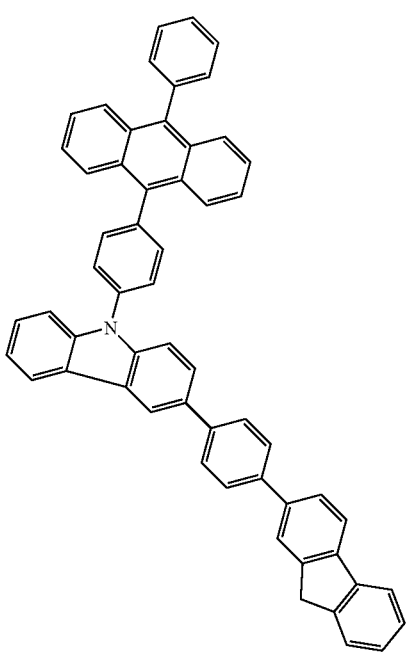

Structual Formula 19
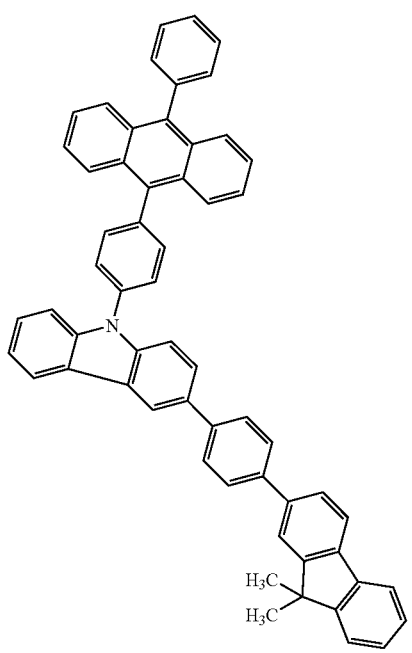
Structual Formula 20
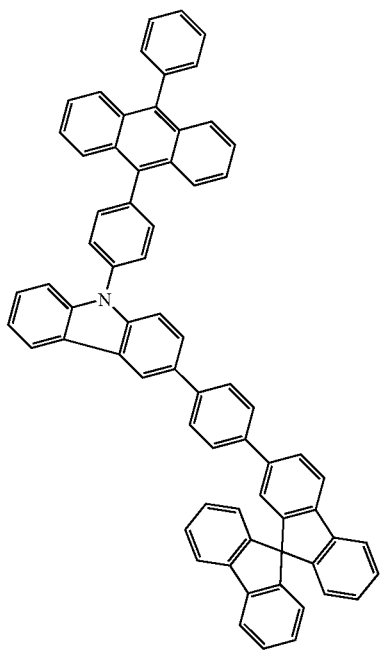
Structual Formula 21
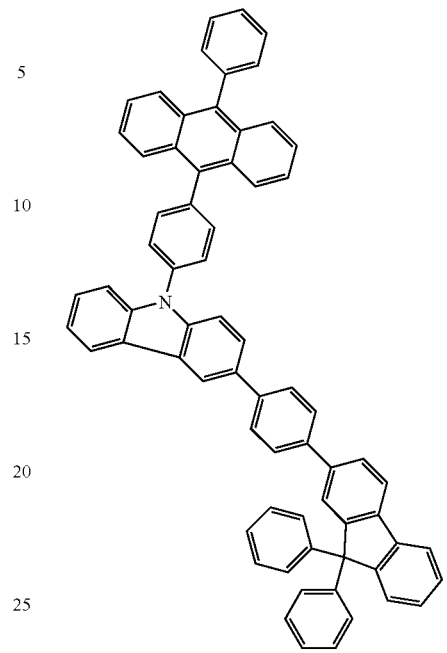
Structual Formula 22
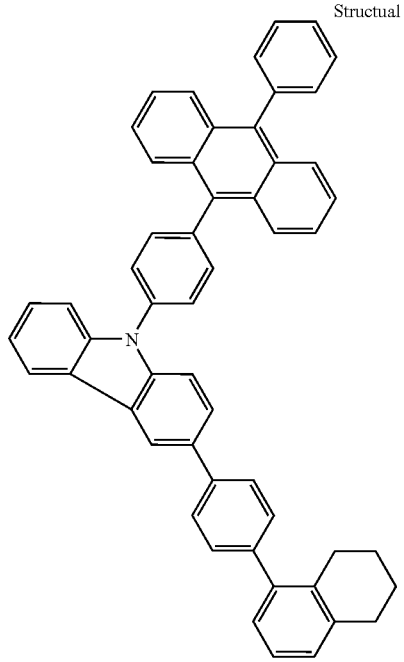

Structual Formula 23
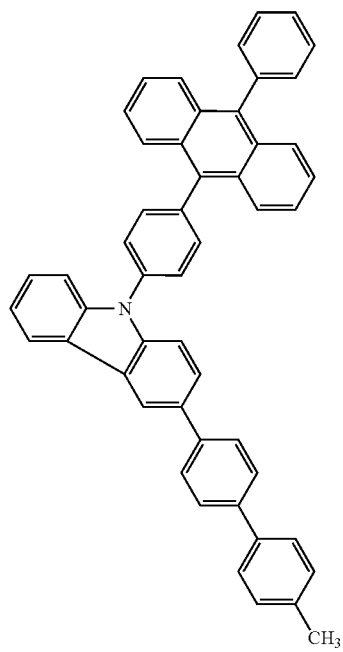
Structual Formula 24
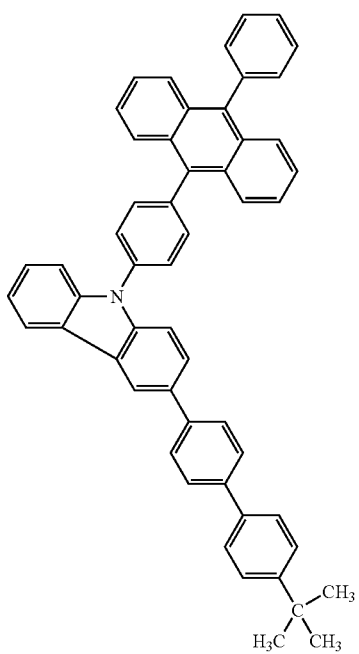
Structual 25
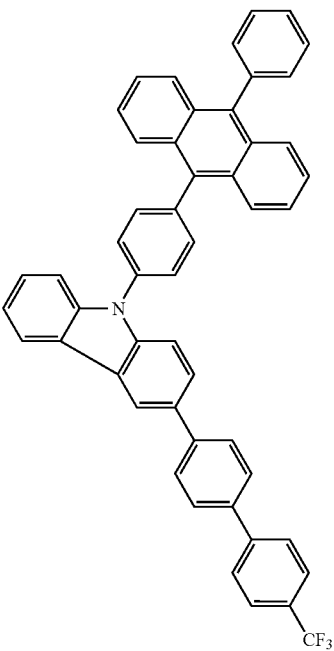
Structual Formula 26
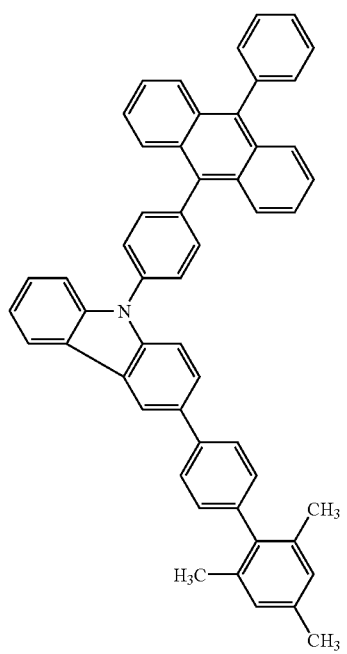

Structual Formula 27
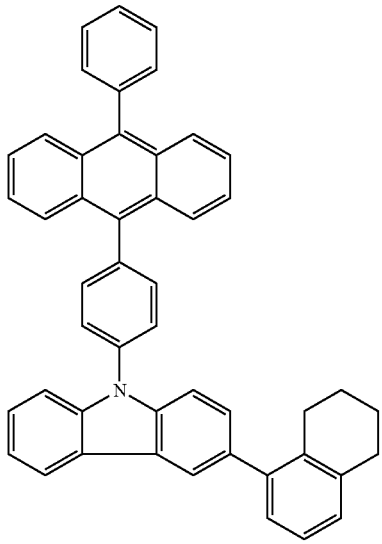
Structual Formula 29
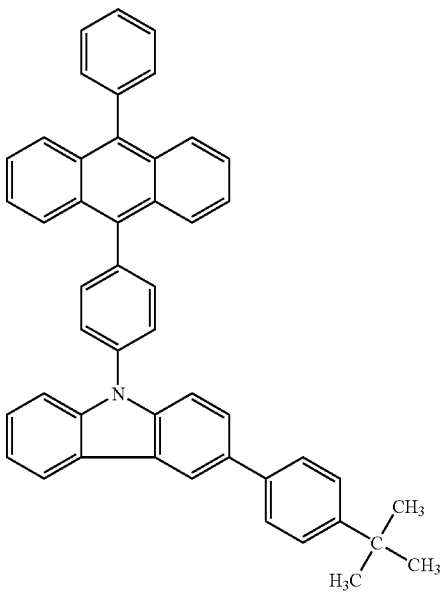
Structual Formula 28
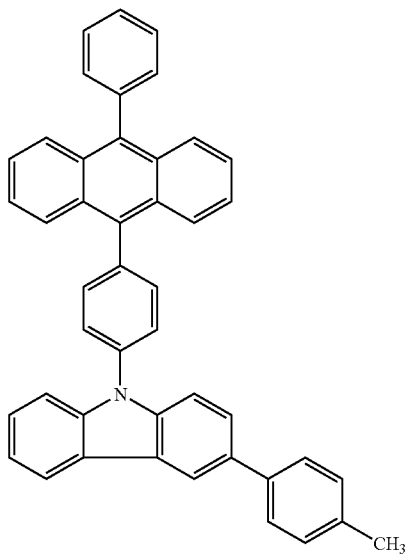
Structual Formula 30
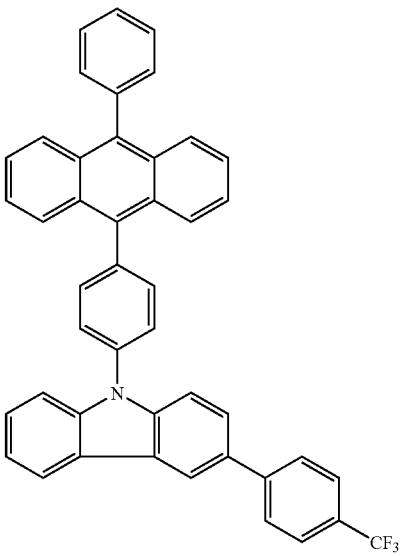

Structual Formula 31

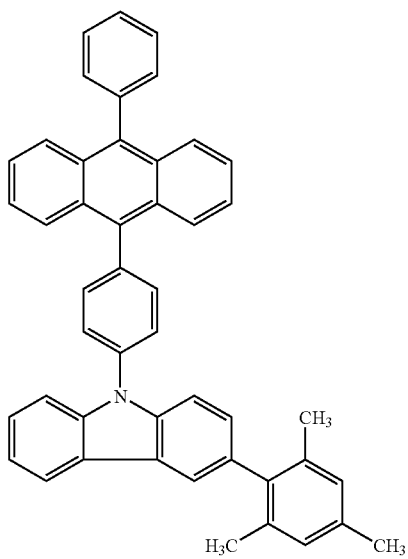

Reaction Formula M1

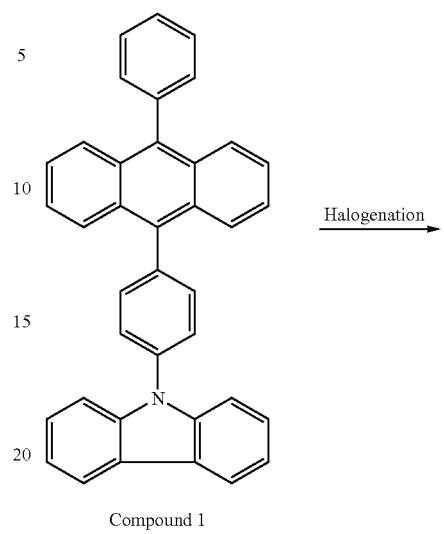

Compound 1

[Embodiment 1]

An example of a production method of the present invention will be detailed hereinbelow. According to the production method which is an embodiment of the present invention, 9-[4-(10-phenyl-9-anthryl)phenyl]-9H-carbazole having an active site at the 3-position of the carbazole skeleton and an aromatic compound having an active site are coupled as described above.

In Embodiment 1, an example in which Suzuki-Miyaura coupling is carried out in the coupling reaction of the above Reaction Formula 2 will be described. When Suzuki-Miyaura coupling is carried out in the coupling reaction of the above Reaction Formula 2, it is preferable that $X^7$ of Compound 2 be a halogen or triflate and that $X^8$ of Compound 3 be boronic acid or an organoboron compound. Alternatively, it is preferable that $X^7$ of Compound 2 be boronic acid or an organoboron compound and that $X^8$ be a halogen or triflate. Moreover, a palladium catalyst is preferably used. In Embodiment 1, an example in which $X^7$ of Compound 2 is a halogen or triflate and $X^8$ of Compound 3 is boronic acid or an organoboron compound will be described. Note that as a coupling reaction of the production method of Embodiment 1, Migita-Kosugi-Stille coupling, Kumada-Tamao coupling, Negishi coupling, or the like can be used.

As described above, the production method also involves: the step for forming 9-[4-(10-phenyl-9-anthryl)phenyl]-9H-carbazole having an active site at the 3-position which is an early step of the production method; and the subsequent coupling step. These reaction steps are illustrated in Reaction Formulae M1 and M2 below. Specifically, as the first step, according to Reaction Formula M1, 9-[4-(10-phenyl-9-anthryl)phenyl]-9H-carbazole (Compound 1, abbreviation: CzPA) is directly halogenated so that Compound M1 in which the 3-position of the carbazole skeleton of CzPA is halogenated is obtained.

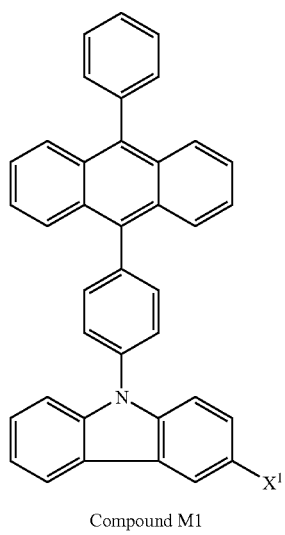

Compound M1

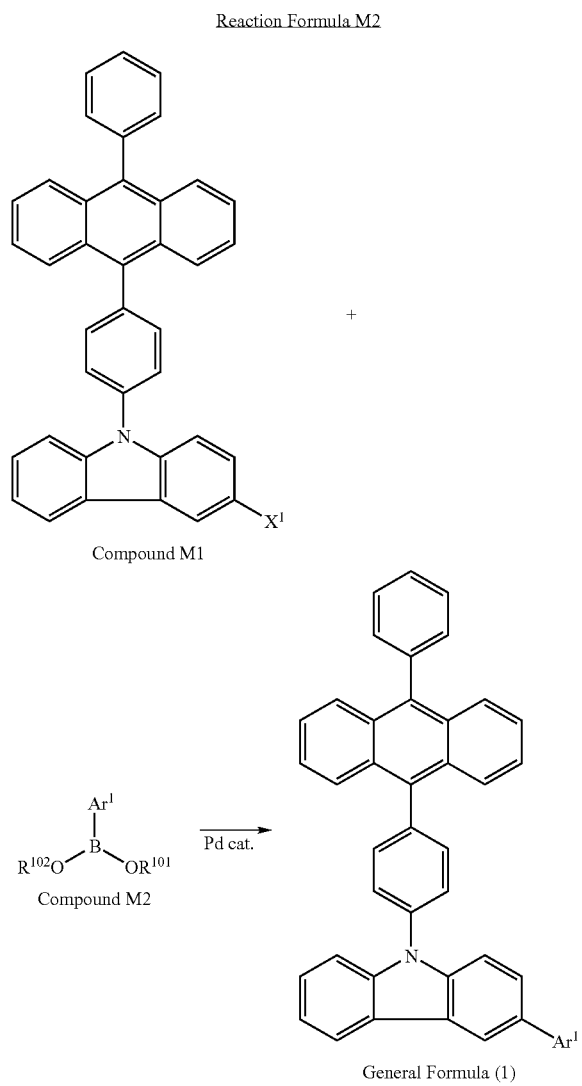

Reaction Formula M2

Compound M1

Compound M2

General Formula (1)

In Reaction Formula M1, $X^1$ represents a halogen, preferably iodine or bromine. When bromination is carried out in this reaction, examples of brominating agents that can be used include bromine, N-bromosuccinimide, and the like. Examples of solvents that can be used for bromination using bromine include, but not limited to, halogen-based solvents such as chloroform and carbon tetrachloride. Examples of solvents that can be used for bromination using N-bromosuccinimide include ethyl acetate, tetrahydrofuran, dimethylformamide, acetic acid, water, and the like.

When iodination is carried out in Reaction Formula M1, examples of iodinating agents that can be used include N-iodosuccinimide, 1,3-diiodo-5,5-dimethylimidazolidine-2,4-dione (abbreviation: DIH), 2,4,6,8-tetraiodo-2,4,6,8-tetrazabicyclo[3,3,0]octane-3,7-dione, 2-iodo-2,4,6,8-tetraazabicyclo[3,3,0]octane-3,7-dione, and the like.

Further, examples of solvents that can be used alone or in combination for iodination using such an iodinating agent include aromatic hydrocarbons such as benzene, toluene, and xylene; ethers such as 1,2-dimethoxyethane, diethyl ether, methyl-t-butyl ether, tetrahydrofuran, and dioxane; saturated hydrocarbons such as pentane, hexane, heptane, octane, and cyclohexane; halogens such as dichloromethane, chloroform, carbon tetrachloride, 1,2-dichloroethane, and 1,1,1-trichloroethane; nitriles such as acetonitrile and benzonitrile; esters such as ethyl acetate, methyl acetate, and butyl acetate; acetic acid (glacial acetic acid); water; and the like.

In the above case, when water is used, water is preferably mixed with an organic solvent. Further, in this reaction, acid such as sulfuric acid or acetic acid is preferably used at the same time, and the acid that can be used is not limited to these examples. Note that a method other than halogenation illustrated in Reaction Formula M1 may be used, and a compound in which a triflate group is substituted at the 3-position of the carbazole skeleton of CzPA may be synthesized.

Next, the reaction of Reaction Formula M2 which is a reaction of the second step is carried out. In this reaction, Compound M1 in which the 3-position of the carbazole skeleton of CzPA is halogenated and an organoboron compound which is Compound M2 are coupled according to a Suzuki-Miyaura reaction using a palladium catalyst, whereby a CzPA derivative represented by General Formula (1) which is the desired substance is obtained. Note that an organoboron compound represented by Compound M2 is referred to as aryl boronic acid when $R^{101}$ and $R^{102}$ independently represent hydrogen.

In Reaction Formula M2, $X^1$ represents a halogen, preferably iodine or bromine. Alternatively, in this reaction formula, a compound in which $X^1$ is a triflate group may be used. Further, in this reaction formula, $Ar^1$ represents an aryl group with 6 to 13 carbon atoms which may have a substituent. Substituents may be bonded to form a ring, and a spiro ring is included in the ring structure. Furthermore, in this reaction formula, $R^{101}$ and $R^{102}$ independently represent hydrogen or an alkyl group having 1 to 6 carbon atoms and may be bonded to form a ring structure.

Examples of palladium catalysts that can be used in Reaction Formula M2 include palladium(II) acetate, tetrakis(triphenylphosphine)palladium(0), and the like. Examples of ligands of the palladium catalyst which can be used here include tri(ortho-tolyl)phosphine, triphenylphosphine, tricyclohexylphosphine, and the like. Examples of bases that can be used in this reaction formula include organic bases such as sodium tert-butoxide, inorganic bases such as potassium carbonate, and the like.

Examples of solvents that can be used in Reaction Formula M2 include a mixed solvent of toluene and water; a mixed solvent of toluene, an alcohol such as ethanol, and water; a mixed solvent of xylene and water; a mixed solvent of xylene, an alcohol such as ethanol, and water; a mixed solvent of benzene and water; a mixed solvent of benzene, an alcohol such as ethanol, and water; a mixed solvent of an ether such as ethyleneglycoldimethylether and water; and the like. Use of a mixed solvent of toluene and water or a mixed solvent of toluene, ethanol, and water is more preferable.

[Embodiment 2]

An example of a light-emitting element formed using any of the carbazole derivatives produced by a production method of the present invention will be described below with reference to FIG. 1A. In this light-emitting element, an EL layer which includes at least a layer including a light-emitting substance (also referred to as a light-emitting layer) is interposed between a pair of electrodes. The EL layer may also have a plurality of layers in addition to the layer including a light-emitting substance. The plurality of layers are a stack of layers each including a substance with a high carrier-inject property or a substance with a high carrier-transport property such that a light-emitting region is formed in a region away from the electrodes, i.e., such that carriers recombine in an area away from the electrodes.

In this specification, the layer including a substance with a high carrier-inject property or a substance with a high carrier-transport property is also referred to as a functional layer which, for example, functions to inject or transport carriers. As the functional layer, it is possible to use any of the following layers: a layer including a substance with a high hole-inject property (also referred to as a hole-inject layer), a layer including a substance with a high hole-transport property (also referred to as a hole-transport layer), a layer including a substance with a high electron-inject property (also referred to as an electron-inject layer), a layer including a substance with a high electron-transport property (also referred to as an electron-transport layer), and the like.

Figure 1B:
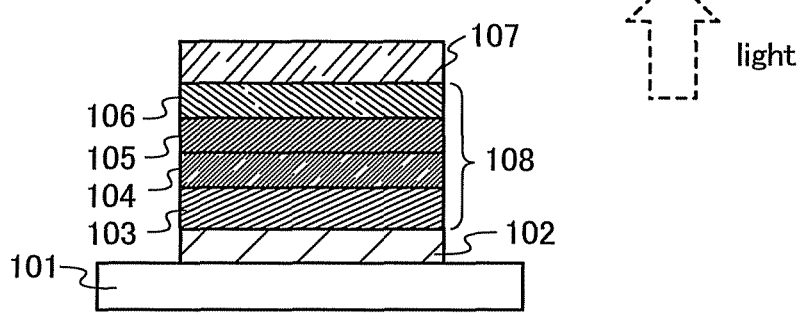
Figure 1C:
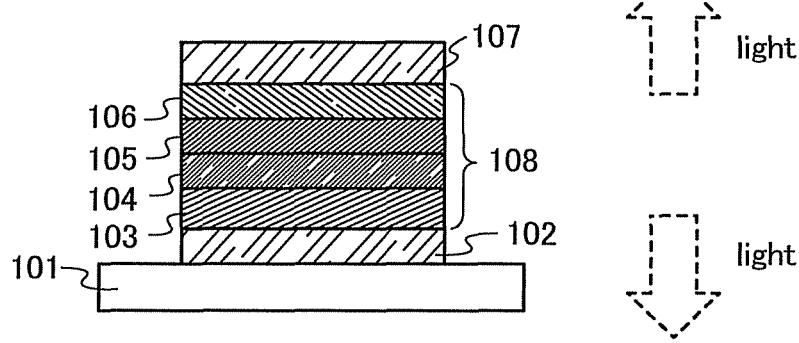

In the light-emitting element of Embodiment 2 which are illustrated in each of FIGS. 1A to 1C, an EL layer 108 is provided between a first electrode 102 and a second electrode 107. The EL layer 108 has a first layer 103, a second layer 104, a third layer 105, and a fourth layer 106. The light-emitting element in each of FIGS. 1A to 1C includes the first electrode 102 over a substrate 101, a stack of the first layer 103, the second layer 104, the third layer 105, and the fourth layer 106 in that order over the first electrode 102, and a second electrode 107 provided thereover. Note that it is assumed that the first electrode 102 functions as an anode and the second electrode 107 functions as a cathode in Embodiment 2.

The substrate 101 is used as a support of the light-emitting element. For the substrate 101, glass, quartz, plastic, or the like may be used, for example. Alternatively, a flexible substrate can be used. The flexible substrate means a substrate that can be bent, such as a plastic substrate made of polycarbonate, polyarylate, polyacrylate, or polyether sulfone, for example. Still alternatively, a film (of polypropylene, polyester, vinyl, polyvinyl fluoride, vinyl chloride, or the like) or a film formed by evaporation of an inorganic material can be used. Note that any material other than these examples may be used as long as the material functions as a support of the light-emitting element during the process of forming the light-emitting element.

Preferably, the first electrode 102 is formed using a metal, an alloy, a conductive compound, a mixture thereof, or the like having a high work function (specifically, 4.0 eV or more). For example, there are ITO (indium oxide-tin oxide), indium oxide-tin oxide containing silicon or silicon oxide, IZO (indium oxide-zinc oxide), IWZO (indium oxide containing tungsten oxide and zinc oxide), and the like. Films of such conductive metal oxides are normally formed by sputtering, but may also be formed by applying a sol-gel method or the like.

For example, a film of IZO (indium oxide-zinc oxide) can be formed by a sputtering method using a target in which zinc oxide is added to indium oxide at 1 to 20 wt %. In addition, a film of IWZO (indium oxide containing tungsten oxide and zinc oxide) can be formed by a sputtering method using a target in which tungsten oxide and zinc oxide are added to indium oxide at 0.5 to 5 wt % and 0.1 to 1 wt % respectively. Further, there are gold (Au), platinum (Pt), nickel (Ni), tungsten (W), chromium (Cr), molybdenum (Mo), iron (Fe), cobalt (Co), copper (Cu), palladium (Pd), a nitride of a metal material (e.g., titanium nitride), and the like.

The first layer 103 is a layer including a substance with a high hole-inject property, and molybdenum oxide, vanadium oxide, ruthenium oxide, tungsten oxide, manganese oxide, or the like can be used. Alternatively, the first layer 103 can be formed using any of the following materials: phthalocyanine compounds such as phthalocyanine (abbreviation: $H_2Pc$) and copper phthalocyanine (CuPc), aromatic amine compounds such as 4,4'-bis[N-(4-diphenylaminophenyl)-N-phenylamino]biphenyl (abbreviation: DPAB) and 4,4'-bis(N-{4-[N-(3-methylphenyl)-N-phenylamino]phenyl}-N-phenylamino)biphenyl (abbreviation: DNTPD), high molecular compounds such as poly(3,4-ethylenedioxythiophene)/poly(styrenesulfonic acid) (PEDOT/PSS), and the like.

Alternatively, for the first layer 103, a composite material formed by composing an organic compound and an inorganic compound can be used. A composite material containing an organic compound and an inorganic compound having an electron-accepting property with respect to the organic compound, in particular, has an excellent hole-inject property and hole-transport property because, in this material, electrons are transported between the organic compound and the inorganic compound to increase the carrier density. When the composite material formed by composing an organic compound and an inorganic compound is used for the first layer 103 as described above, the first layer 103 can achieve an ohmic contact with the first electrode 102; therefore, a material of the first electrode can be selected regardless of the work function.

The inorganic compound used for the composite material is preferably an oxide of a transition metal. Moreover, oxides of metals of Groups 4 to 8 of the periodic table can be given. Specifically, use of vanadium oxide, niobium oxide, tantalum oxide, chromium oxide, molybdenum oxide, tungsten oxide, manganese oxide, or rhenium oxide is preferable because of their high electron-accepting properties. In particular, use of molybdenum oxide is more preferable because of its stability in the atmosphere, a low hygroscopic property, and easily handling.

As the organic compound used for the composite material, any of a variety of compounds such as aromatic amine compounds, carbazole derivatives, aromatic hydrocarbons, or high molecular compounds (oligomers, dendrimers, polymers, etc.) can be used. Note that the organic compound used for the composite material preferably has a high hole-transport property. Specifically, a substance having a hole mobility of $10^{-6}$ cm$^2$/Vs or more is preferably used. Further, any other substance may be used as long as it is a substance in which the hole-transport property is higher than the electron-transport property. Hereinbelow, organic compounds that can be used for the composite material are specifically given.

Examples of the aromatic amine compounds include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), 4,4'-bis(N-{4-[N-(3-methylphenyl)-N-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), and the like.

Specific examples of the carbazole derivatives that can be used for the composite material include 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

Alternatively, 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)]phenyl-10-phenylanthracene (abbreviation: CzPA), 1,4-bis[4-(N-carbazolyl)phenyl]-2,3,5,6-tetraphenylbenzene, or the like can be used.

Further, examples of the aromatic hydrocarbons that can be used for the composite material include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9, 10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl)phenyl]anthracene, 9,10-bis[2-(1-naphthyl)phenyl]anthracene, and the like.

Furthermore, there are 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl) perylene, and the like. Besides, there are pentacene, coronene, and the like. Use of an aromatic hydrocarbon that has a hole mobility of $1 \times 10^{-6}$ cm$^2$/(V·s) or more and has 14 to 42 carbon atoms, as given above, is more preferable.

Note that the aromatic hydrocarbons that can be used for the composite material may have a vinyl skeleton. Examples of the aromatic hydrocarbons having a vinyl skeleton include 4,4'-bis(2,2-diphenylvinyl)biphenyl (abbreviation: DPVBi), 9,10-bis[4-(2,2-diphenylvinyl)phenyl]anthracene (abbreviation: DPVPA), and the like. Alternatively, a high molecular compound such as poly(N-vinylcarbazole) (abbreviation: PVK) or poly(4-vinyltriphenylamine) (abbreviation: PVTPA) can be used.

It is preferable that a substance forming the second layer 104 be a substance with a high hole-transport property, specifically, an aromatic amine compound (i.e., a compound having a benzene ring-nitrogen bond). As widely used materials, there are 4,4'-bis[N-(3-methylphenyl)-N-phenylamino] biphenyl, derivatives thereof such as 4,4'-bis[N-(1-napthyl)-N-phenylamino]biphenyl (hereinafter referred to as NPB), and star burst aromatic amine compounds such as 4,4',4"-tris (N,N-diphenyl-amino)triphenylamine, and 4,4',4"-tris[N-(3-methylphenyl)-N-phenylamino]triphenylamine.

The substances given here are mainly substances having a hole mobility of $10^{-6}$ cm$^2$/Vs or more. Note that any other substance may also be used as long as it is a substance in which the hole-transport property is higher than the electron-transport property. Further, the second layer 104 is not limited to a single layer and may be a mixed layer or a stack of two or more layers including any of the above-mentioned substances. Alternatively, any of the above hole-transport materials may be added to a high molecular compound that is electrically inactive, such as PMMA.

Alternatively, any of the following high molecular compounds may be used: poly(N-vinylcarbazole) (abbreviation: PVK), poly(4-vinyltriphenylamine) (abbreviation: PVTPA), poly [N-(4-{N'-[4-(4-diphenylamino)phenyl]phenyl-N'-phenylamino}phenyl)methacrylamide] (abbreviation: PTP-DMA), and poly[N,N'-bis(4-butylphenyl)-N,N'-bis(phenyl) benzidine] (abbreviation: Poly-TPD). Further alternatively, to any of these high molecular compounds, any of the above-mentioned hole-transport materials may be added as appropriate.

The third layer 105 is a layer including a light-emitting substance (also referred to as a light-emitting layer). In Embodiment 2, the third layer 105 is formed using any of the carbazole derivatives obtained by a production method described in Embodiment 1. The carbazole derivatives exhibit blue light emission and thus are suitable for use as a light-emitting substance in a light-emitting element. Further, the carbazole derivatives obtained by a production method of Embodiment 1 (hereinafter, simply referred to as carbazole derivatives according to an embodiment of the present invention, in some cases) can also be used as a host of the third layer 105, and a structure in which a dopant serving as a light-emitting substance is dispersed in the carbazole derivative can provide light emission from the dopant serving as a light-emitting substance.

When any of the carbazole derivatives according to an embodiment of the present invention is used as a material in which another light-emitting substance is dispersed, an emission color depending on the light-emitting substance can be obtained. Also, a mixture of an emission color depending on the carbazole derivative according to the embodiment of the present invention and an emission color depending on the light-emitting substance dispersed in the carbazole derivative can be obtained.

Alternatively, by formation of a light-emitting element in which any of the carbazole derivatives according to an embodiment of the present invention is included in a layer including a material (host) that has a band gap larger than the carbazole derivative, light emission from the carbazole derivative according to the embodiment of the present invention can be obtained. In other words, any of the carbazole derivatives according to an embodiment of the present invention can serve as a dopant. Here, since the carbazole derivatives according to an embodiment of the invention have an extremely large band gap and emit light of a short wavelength, a light-emitting element which can provide blue light emission with highly color purity can be formed.

Here, any of a variety of materials can be used as a light-emitting substance that is to be dispersed in any of the carbazole derivatives according to an embodiment of the present invention. Specifically, any of the following fluorescent substances which emit fluorescence can be used: 9,10-diphenyl-2-[N-phenyl-N-(9-phenyl-9H-carbazol-3-yl)amino]an-thracene (abbreviation: 2PCAPA), 4-(dicyanomethylene)-2-methyl-6-(p-dimethylaminostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridone (abbreviation: DMQd), rubrene, and the like.

Alternatively, a fluorescent substance which emits fluorescence, such as N,N'-bis[4-(9H-carbazol-9-yl)phenyl]-N,N-diphenylstilbene-4,4'-diamine (abbreviation: YGA2S) or 4-(9H-carbazol-9-yl)-4'-(10-phenyl-9-anthryl)tripheny-lamine (abbreviation: YGAPA), can be used. Further alternatively, a phosphorescent substances which emits phosphorescence, (acetylacetonato)bis[2,3-bis(4-fluorophenyl) quinoxalinato]iridium(III) (abbreviation: Ir(Fdpq)$_2$(acac)) or (2,3,7,8,12,13,17,18-octaethyl-21H,23H-porphyrinato) platinum(II) (abbreviation: PtOEP) can be used.

For the fourth layer 106, a substance with a high electron-transport property can be used. For example, the fourth layer 106 is formed using a metal complex having a quinoline or benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo[h] quinolinato)beryllium (abbreviation: BeBq$_2$), or bis(2-methyl-8-quinolinolato)(4-phenylphenolato)aluminum (abbreviation: BAlq), or the like. Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)-benzothiazolato]zinc (abbreviation: Zn(BTZ)$_2$), or the like can be used.

Instead of the metal complexes, any of the following substances can be used: 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), and the like. The substances given here are substances having an electron mobility of $10^{-6}$ cm$^2$/(V·s) or more. Note that any substance other than the above substances may also be used as long it is a substance in which the electron-transport property is higher than the hole-transport property. Furthermore, the electron-transport layer is not limited to a single layer and may be a stack of two or more layers each containing any of the aforementioned substances.

Further, a layer having a function of promoting electron injection (an electron-inject layer) may be provided between the fourth layer 106 and the second electrode 107. For the layer having a function of promoting electron injection, an alkali metal, an alkaline earth metal, or a compound thereof, such as lithium fluoride (LiF), cesium fluoride (CsF), or calcium fluoride (CaF$_2$), can be used. For example, it is possible to use a layer including an electron-transport substance which includes an alkali metal, an alkaline earth metal, or a compound thereof, a layer including Alq which includes magnesium (Mg), or the like. Note that the use of a layer including an electron-transport substance which includes an alkali metal or an alkaline earth metal is more preferable, in which case electron injection from the second electrode 107 proceeds efficiently.

As a substance Miming the second electrode 107, a metal, an alloy, an electrically conductive compound, a mixture thereof; or the like with a low work function (specifically, a work function of 3.8 eV or lower) can be used. As specific examples of such cathode materials, there are elements of Group 1 or Group 2 of the periodic table, i.e., alkali metals such as lithium (Li) and cesium (Cs), alkaline earth metals such as magnesium (Mg), calcium (Ca), and strontium (Sr), alloys containing any of these metals (e.g., MgAg and AlLi), rare earth metals such as europium (Eu) and ytterbium (Yb), alloys containing any of these metals, and the like.

However, for the second electrode 107, any of a variety of conductive materials such as Al, Ag, ITO, and ITO containing silicon or silicon oxide can be used regardless of the work function by the provision of the layer having a function of promoting electron injection between the second electrode 107 and the fourth layer 106 so as to form a stack with this second electrode.

Further, since the carbazole derivatives according to an embodiment of the present invention are bipolar substances which have a high electron-transport property and a high hole-transport property, the carbazole derivatives can also be used as a carrier-transport material for a functional layer of a light-emitting element. For example, any of the carbazole derivatives according to an embodiment of the present invention can be used for a hole-transport layer or an electron-transport layer, which is a carrier-transport layer, or a hole-inject layer or an electron-inject layer.

Further, for the formation of the first layer 103, the second layer 104, the third layer 105, and the fourth layer 106, any of a variety of methods such as an evaporation method, a sputtering method, a droplet discharging method (an inkjet method), a spin coating method, or a printing method can be employed. Further, a different film formation method may be used for each electrode or each layer. When a wet method is employed to form a thin film using a composition in a solution form which is obtained by dissolving any of the carbazole derivatives according to an embodiment of the present invention in a solvent, the thin film is formed in such a manner that the composition in a solution form which includes the carbazole derivative and the solvent is attached to a region where the thin film is to be formed, the solvent is removed, and the resulting material is solidified.

As the wet method, any of the following methods can be employed: a spin coating method, a roll coating method, a spray method, a casting method, a dipping method, a droplet discharging (ejection) method (an inkjet method), a dispenser method, a variety of printing methods (a method by which a thin film can be formed to have a desired pattern, such as screen (stencil) printing, offset (planographic) printing, letterpress printing, or gravure (intaglio) printing), or the like. Note that as long as a liquid composition is used, there is no limitation on the above-described methods and the composition of the embodiment of the present invention can be used.

Any of a variety of organic compounds can be used as the solvent in the above-described composition. For example, by using a solvent that has an aromatic ring (e.g., a benzene ring), such as toluene, xylene, methoxybenzene (anisole), dodecylbenzene, or a mixed solvent of dodecylbenzene and tetralin, any of the carbazole derivatives can be dissolved. Further, any of the above-described carbazole derivatives can also be dissolved in a solvent that does not have an aromatic ring, such as dimethylsulfoxide (DMSO), dimethylformamide (DMF), or chloroform.

As other examples of the solvents, there are ketone-based solvents such as acetone, methyl ethyl ketone, diethyl ketone, n-propyl methyl ketone, and cyclohexanone, ester-based solvents such as ethyl acetate, n-propyl acetate, n-butyl acetate, ethyl propionate, γ-butyrolactone, and diethyl carbonate, ether-based solvents such as diethyl ether, tetrahydrofuran, and dioxane, alcohol-based solvents such as ethanol, isopropanol, 2-methoxyethanol, and 2-ethoxyethanol, and the like.

The composition described in Embodiment 2 may further include another organic material. As the organic material, there are aromatic compounds or heteroaromatic compounds which are solid at room temperature. A low molecular compound or a high molecular compound can be used as the organic material. When a low molecular compound is used, a low molecular compound having a substituent that improves the solubility in a solvent is preferably used. The composition may further include a binder in order to improve film properties of a film that is to be formed. As the binder, a high molecular compound that is electrically inactive is preferably used. Specifically, polymethylmethacrylate (abbreviation: PMMA), polyimide, or the like can be used.

In the light-emitting element of Embodiment 2 which has the structure as described above, the potential difference generated between the first electrode 102 and the second electrode 107 makes a current flow, whereby holes and electrons recombine in the third layer 105 which is a layer including a high light-emitting property and accordingly light is emitted. In other words, a light-emitting region is formed in the third layer 105. The emitted light is extracted out through one or both of the first electrode 102 and the second electrode 107. Therefore, one or both of the first electrode 102 and the second electrode 107 is/are an electrode having a light-transmitting property.

When only the first electrode 102 is a light-transmitting electrode, light is extracted from the substrate side through the first electrode 102, as illustrated in FIG. 1A. In contrast, when only the second electrode 107 is a light-transmitting electrode, light is extracted from a side opposite to the substrate side through the second electrode 107, as illustrated in FIG. 1B. When both the first electrode 102 and the second electrode 107 are light-transmitting electrodes, light is extracted from both the substrate side and the side opposite to the substrate side through the first electrode 102 and the second electrode 107, as illustrated in FIG. 1C.

Note that the structure of the layers provided between the first electrode 102 and the second electrode 107 is not limited to the above structure and may be any structure as long as the light-emitting region for recombination of holes and electrons is positioned away from the first electrode 102 and the second electrode 107 so as to suppress quenching by the light-emitting region being close to metal. In other words, there is no particular limitation on the stack structure of the layers as long as the light-emitting layer including any of the carbazole derivatives according to an embodiment of the present invention is freely combined with the layer including a substance with a high electron-transport property, the layer including a substance with a high hole-transport property, the layer including a substance with a high electron-inject property, the layer including a substance with a high hole-inject property, the layer including a bipolar substance (a substance with a high electron-transport and a high hole-transport property), the layer including a hole-blocking material, etc.

Figure 2:
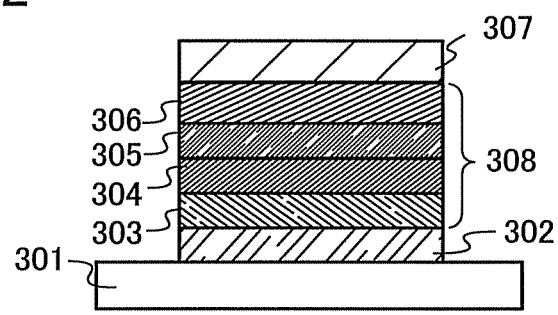
FIG. 2 illustrates a light-emitting element according to an embodiment of the present invention.

In a light-emitting element illustrated in FIG. 2, an EL layer 308 is provided between a first electrode 302 and a second electrode 307 over a substrate 301. The EL layer 308 has a first layer 303 including a substance with a high electron-transport property, a second layer 304 including a light-emitting substance, a third layer 305 including a substance with a high hole-transport property, and a fourth layer 306 including a substance with high hole-inject property. The first electrode 302 which is to function as a cathode, the first layer 303 including a substance with a high electron-transport property, the second layer 304 including a light-emitting substance, the third layer 305 including a substance with a high hole-transport property, the fourth layer 306 including a substance with high hole-inject property, and the second electrode 307 which is to function as an anode are stacked in that order.

Hereinafter, a method of forming the light-emitting element will be described in specific terms. The light-emitting element of Embodiment 2 has a structure in which an EL layer is interposed between a pair of electrodes. The EL layer includes at least the layer including a light-emitting substance (also referred to as a light-emitting layer) which is formed using any of the carbazole derivatives according to an embodiment of the present invention. The EL layer may include the functional layer (the hole-inject layer, the hole-transport layer, the electron-transport layer, the electron-inject layer, etc.). The electrodes (the first electrode and the second electrode), the layer including a light-emitting substance, and the functional layer may be formed by any of the wet methods such as a droplet discharging method (an inkjet method), a spin coating method, or a printing method, or by a dry method such as a vacuum evaporation method, a CVD method, or a sputtering method.

The use of a wet method enables the formation at atmospheric pressure, which can be achieved with a simple device and process, and thus has the effects of simplifying the process and improving the productivity. In contrast, in a dry method, dissolution of a material is not needed, and thus a material that has low solubility in a solution can be used to expand the range of material choices. All the thin films included in the light-emitting element may be formed by a wet method. In this case, the light-emitting element can be formed with only facilities needed for a wet method.

Alternatively, the stack up to the layer including a light-emitting substance may be formed by a wet method, and the functional layer, the second electrode, etc. which are stacked on the layer including a light-emitting substance may be formed by a dry method. Further alternatively, the first electrode and the functional layer may be formed by a dry method before the formation of the layer including a light-emitting substance, and the layer including a light-emitting substance, the functional layer stacked thereover, and the second electrode may be formed by a wet method. Needless to say, the embodiment of the present invention is not limited to this example, and the light-emitting element can be formed by appropriate selection from a wet method and a dry method depending on a material that is to be used, necessary film thickness, and the interface state.

In Embodiment 2, the light-emitting element is formed over a substrate made of glass, plastic, or the like. By formation of a plurality of such light-emitting elements over one substrate, a passive matrix light-emitting device can be fabricated. Alternatively, the light-emitting element may be formed over an electrode that is electrically connected to, for example, a TFT (thin film transistor) formed over a substrate formed using glass, plastic, or the like. Thus, an active matrix light-emitting device in which driving of the light-emitting element is controlled by a TFT can be fabricated.

Note that there is no limitation on the structure of a TFT, and a staggered TFT or an inverted staggered TFT may be used. In addition, there is no limitation on crystallinity of a semiconductor used for the TFT, and an amorphous semiconductor may be used, or a crystalline semiconductor may be used. Further, a driving circuit formed over a TFT substrate may be formed using an n-channel TFT and a p-channel TFT, or may be formed using any one of an n-channel TFT or a p-channel TFT.

The carbazole derivatives according to an embodiment of the present invention have an extremely large band gap. Therefore, even with the use of a dopant that emits light of a relatively short wavelength, particularly blue light, light emission not from the carbazole derivative but from the dopant can be efficiently obtained. Further, these carbazole derivatives have a wide band gap and are bipolar substances which have a high electron-transport property and a high hole-transport property. Accordingly, by using any of the carbazole derivatives according to the embodiment of the present invention for a light-emitting element, the highly reliable light-emitting element with a good carrier balance can be obtained. Furthermore, with the use of any of these derivatives, a highly reliable light-emitting device and electronic device can be obtained.

[Embodiment 3]

Figure 3A:
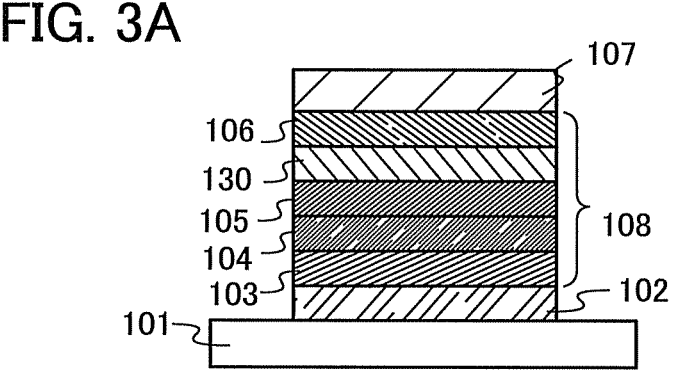
FIGS. 3A and 3B each illustrate a light-emitting element according to an embodiment of the present invention.
Figure 3B:
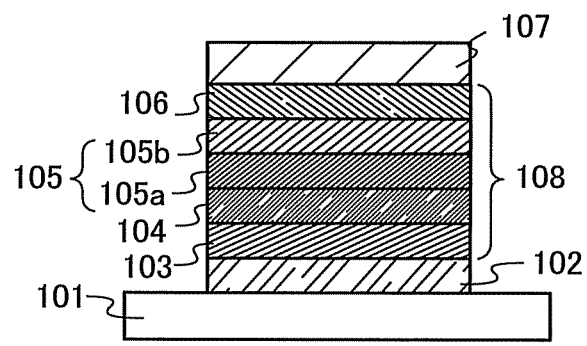

In Embodiment 3, light-emitting elements having structures that are different from those of the light-emitting elements given in Embodiment 2 will be described using FIGS. 3A and 3B. In Embodiment 3, as illustrated in FIG. 3A, a layer 130 for controlling transport of electron carriers are provided between the fourth layer 106 which is an electron-transport layer and the third layer 105 which is a light-emitting layer (also referred to as a light-emitting layer 105). Thus, a layer for controlling transport of electron carriers may be provided between an electron-transport layer and a light-emitting layer.

This layer for controlling transport of electron carriers is formed by adding a small amount of substance with a high electron-trapping property to a material with a high electron-transport property as aforementioned, or alternatively, by adding a material with a low LUMO (lowest unoccupied molecular orbital) energy level and a hole-transport property to a material with a high electron-transport property. By suppressing transport of electron carriers, the carrier balance can be adjusted. Such a structure is very effective in suppressing problems (e.g., shortening of element lifetime) caused when electrons pass through the third layer 105.

As another structure, the light-emitting layer 105 may include a plurality of layers which are two or more layers. FIG. 3B illustrates an example in which the light-emitting layer 105 includes a plurality of layers which are two layers:

a first light-emitting layer 105a and a second light-emitting layer 105b. For example, when the first light-emitting layer 105a and the second light-emitting layer 105b are stacked in that order from the second layer 104 side which is a hole-transport layer to form the light-emitting layer 105, a structure in which a substance with a hole-transport property is used as the host material of the first light-emitting layer 105a and a substance with an electron-transport property is used for the second light-emitting layer 105b may be employed.

For a light-emitting layer, any of the carbazole derivatives according to an embodiment of the present invention can be used alone or as a host or even as a dopant. When any of these carbazole derivatives is used as a host, a structure in which a dopant is dispersed in the carbazole derivative according to the embodiment of the present invention can provide light emission from the dopant. Alternatively, when any of the carbazole derivatives according to the embodiment of the present invention is used as a dopant, a structure in which the carbazole derivative is included in a layer containing a material (host) that has a band gap larger than the derivative can provide light emission from the carbazole derivative according to the embodiment of the present invention.

Further, the carbazole derivatives according to an embodiment of the present invention are bipolar substances which have a hole-transport property and a high electron-transport property. Therefore, for use of the hole-transport property, any of the carbazole derivatives can be used for the first light-emitting layer 105a, or for use of the electron-transport property, any of the carbazole derivatives can be used for the first light-emitting layer 105b. For each of the light-emitting layers 105a and 105b, the carbazole derivative can be used alone or as a host material or even as a dopant material. When any of the carbazole derivatives is used alone or as a host material, which of the light-emitting layer 105a with a hole-transport property and the light-emitting layer 105b with an electron-transport property includes the derivative may depend on the carrier-transport property of the carbazole derivative. Note that Embodiment 3 can be combined with any other embodiment as appropriate.

[Embodiment 4]

In Embodiment 4, an example of a light-emitting element including a stack of a plurality of units (also referred to as a stacked-type element) in which one unit means any of the light-emitting elements described in Embodiment 2 will be described with reference to FIG. 4. In this light-emitting element, a plurality of light-emitting units are formed between a first electrode and a second electrode. Note that in formation of such a light-emitting element including a stack of a plurality of units, electrodes that would be located between the units are omitted.

Figure 4:
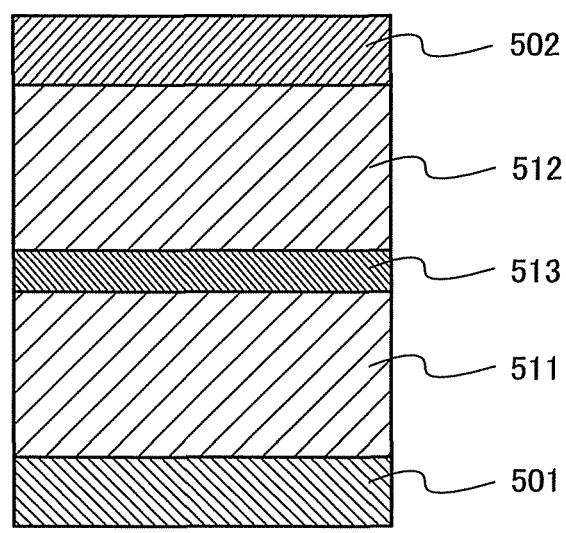
FIG. 4 illustrates a light-emitting element according to an embodiment of the present invention.

In FIG. 4, a first light-emitting unit 511 and a second light-emitting unit 512 are stacked between a first electrode 501 and a second electrode 502. Electrodes that are similar to the electrodes of Embodiment 2 can be applied to the first electrode 501 and the second electrode 502. Further, the first light-emitting unit 511 and the second light-emitting unit 512 may have either the same or different structure, which can be similar to those described in Embodiment 2.

A charge generation layer 513 includes a composite material of an organic compound and a metal oxide. This composite material of an organic compound and a metal oxide corresponds to the composite material described in Embodiment 2 and includes an organic compound and a metal oxide such as $V_2O_5$, $MoO_3$, or $WO_3$. As the organic compound, any of variety of compounds such as aromatic amine compounds, carbazole derivatives, aromatic hydrocarbons, oligomers, dendrimers, or high molecular compounds (such as polymers) can be used.

Further, as the organic compound, an organic compound having a hole mobility of $10^{-6}$ cm$^2$/(V·s) or more is preferably applied. Note that a substance other than these compounds may also be used as long as it is a substance in which the hole-transport property is higher than the electron-transport property. Since the composite material of an organic compound and a metal oxide has an excellent carrier-inject property and carrier-transport property, low-voltage driving or low-current driving can be realized.

Alternatively, for the charge generation layer 513, the composite material of an organic compound and a metal oxide may be combined with another material. For example, a layer including the composite material of an organic compound and a metal oxide may be combined with a layer including one compound selected from among electron-donating substances and a compound having a high electron-transport property. Further alternatively, for the charge generation layer 513, a layer including the composite material of an organic compound and a metal oxide may be combined with a transparent conductive film.

In any case, the charge generation layer 513 interposed between the first light-emitting unit 511 and the second light-emitting unit 512 may have any structure as long as electrons can be injected into the light-emitting unit on one side and holes can be injected into the light-emitting unit on the other side when a voltage is applied between the first electrode 501 and the second electrode 502.

In Embodiment 4, the light-emitting element having two light-emitting units is described. However, the present invention can be applied to a light-emitting element in which three or more light-emitting units are stacked. As in the light-emitting element according to Embodiment 4, by arranging a plurality of light-emitting units between a pair of electrodes so that the plurality of light-emitting units can be partitioned by a charge generation layer, light emission in a high luminance region can be achieved with current density kept low; thus, a light-emitting element having long lifetime can be realized. Further, when the light-emitting element is applied to a lighting apparatus, voltage drop due to the resistance of the electrode materials can be suppressed; accordingly, uniform light emission in a large area can be achieved. Furthermore, a light-emitting device capable of low-voltage driving with low power consumption can be realized. Note that Embodiment 4 can be combined with any other embodiment as appropriate.

[Embodiment 5]

In Embodiment 5, a light-emitting device formed using any of the carbazole derivatives according to an embodiment of the present invention is described using FIGS. 5A and 5B. FIG. 5A is a top view illustrating the light-emitting device, and FIG. 5B is a cross-sectional view of FIG. 5A which is taken along lines A-B and C-D. Reference numeral 601 denotes a driver circuit portion (a source side driver circuit), reference numeral 602 denotes a pixel portion, and reference numeral 603 denotes a driver circuit portion (a gate side driver circuit), which are shown by a dotted line. Further, reference numeral 604 denotes a sealing substrate, and reference numeral 605 denotes a sealing material. Reference numeral 607 denotes a space surrounded by the sealing material 605

Note that a leading wiring 608 is a wiring for transmitting signals that are input to the source side driver circuit 601 and the gate side driver circuit 603. The leading wiring 608 receives video signals, clock signals, start signals, reset signals, and the like from an FPC (flexible printed circuit) 609 serving as an external input terminal. Note that although only an FPC is illustrated here, this FPC may be provided with a PWB (printed wiring board). The light-emitting device in this specification includes not only a light-emitting device itself but also a light-emitting device to which an FPC or a PWB is attached.

Then, a cross-sectional structure will be described using FIG. 5B. The driver circuit portions and the pixel portion are provided over an element substrate 610, but only the source side driver circuit 601 which is the driver circuit portion and one pixel of the pixel portion 602 are illustrated. In the source side driver circuit 601, a CMOS circuit which is a combination of an n-channel TFT 623 and a p-channel TFT 624 is formed. The driver circuits may be formed using any of various types of circuits such as a CMOS circuit, a PMOS circuit, and an NMOS circuit. Note that in Embodiment 5, a driver-integrated type in which a driver circuit is formed over a substrate provided with a pixel portion is described; however, the present invention is not limited to this type, and the driver circuit can be formed outside the substrate instead of being formed over the substrate provided with the pixel portion.

Further, the pixel portion 602 includes a plurality of pixels each having a switching TFT 611, a current controlling TFT 612, and a first electrode 613 which is electrically connected to a drain of the current controlling TFT 612. Note that an insulator 614 is formed to cover an end portion of the first electrode 613. Here, a positive photosensitive acrylic resin film is used to form the insulator 614.

Furthermore, in order to improve coverage, the insulator 614 is provided such that either an upper end portion or a lower end portion of the insulator 614 has a curved surface with a curvature. For example, when a positive photosensitive acrylic resin is used as a material for the insulator 614, it is preferable that only the upper end portion of the insulator 614 have a curved surface with a radius of curvature (0.2 to 3 μm). Alternatively, the insulator 614 can be formed using either a negative type that becomes insoluble in an etchant by light irradiation or a positive type that becomes soluble in an etchant by light irradiation.

A layer 616 including a light-emitting substance and a second electrode 617 are formed over the first electrode 613. Here, it is preferable that the first electrode 613 serving as an anode be formed using a material with a high work function. For example, the first electrode 613 can be formed using a single-layer film of an ITO film, a film of indium tin oxide containing silicon, a film of indium oxide containing zinc oxide at 2 to 20 wt %, a titanium nitride film, a chromium film, a tungsten film, a Zn film, a Pt film, or the like, a stack of a titanium nitride film and a film containing aluminum as the main component, a stack of three layers: a titanium nitride film, a film containing aluminum as the main component, and another titanium nitride film, or the like. Note that with the use of a stack structure, resistance as a wiring is low, a good ohmic contact is formed, and further, the first electrode 613 can be made to function as an anode.

In addition, the layer 616 including a light-emitting substance is formed by any of a variety of methods, for example, an evaporation method using an evaporation mask, a droplet discharging method such as an inkjet method, a printing method, or a spin coating method. The layer 616 including a light-emitting substance includes any of the carbazole derivatives described in Embodiment 1. Further, another material included in the layer 616 including a light-emitting substance may be a low molecular material, an oligomer, a dendrimer, or a high molecular material.

As a material used for the second electrode 617 which is formed over the layer 616 including a light-emitting substance and functions as a cathode, a material having a low work function (e.g., Al, Mg, Li, Ca, an alloy or a compound thereof such as MgAg, MgIn, AlLi, LiF, or $CaF_2$) is preferably used. Note that when light generated in the layer 616 including a light-emitting substance is transmitted through the second electrode 617, the second electrode 617 may be a stack of a metal thin film with a reduced thickness and a transparent conductive film (e.g., a film of ITO, indium oxide containing zinc oxide at 2 to 20 wt %, indium oxide-tin oxide containing silicon or silicon oxide, or ZnO (zinc oxide)).

Furthermore, by attaching the sealing substrate 604 and the element substrate 610 to each other with the sealing material 605, a light-emitting element 618 is provided in the space 607 surrounded by the element substrate 610, the sealing substrate 604, and the sealing material 605. Note that the space 607 is filled with a filler, and here are also cases where the space 607 may be filled with an inert gas (e.g., nitrogen or argon) as such a filler, or where the space 607 may be filled with the sealing material 605. As the sealing material 605, an epoxy-based resin is preferably used. In addition, it is preferable that such a material allow penetration of as little moisture or oxygen as possible.

Furthermore, as a material used for the sealing substrate 604, a plastic substrate made of FRP (fiberglass-reinforced plastics), PVF (polyvinyl fluoride), polyester, acrylic, or the like can be used in addition to a glass substrate or a quartz substrate. As described above, a light-emitting device fabricated using any of the carbazole derivatives according to an embodiment of the present invention can be obtained.

The carbazole derivatives have a wide band gap and are bipolar substances which have a high electron-transport property and a high hole-transport property. Accordingly, by using any of the carbazole derivatives according to the embodiment of the present invention for a light-emitting element, the highly reliable light-emitting element with a good carrier balance can be obtained. Furthermore, with the use of any of the carbazole derivatives according to the embodiment of the present invention, a highly reliable light-emitting device and electronic device can be obtained.

Figure 6A:
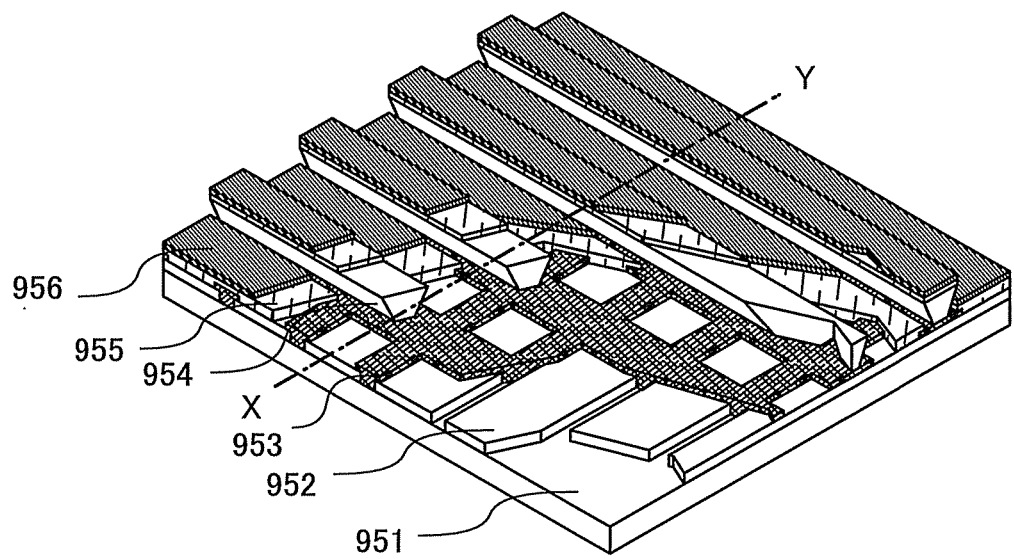
FIGS. 6A and 6B illustrate a light-emitting device according to an embodiment of the present invention.
Figure 6B:
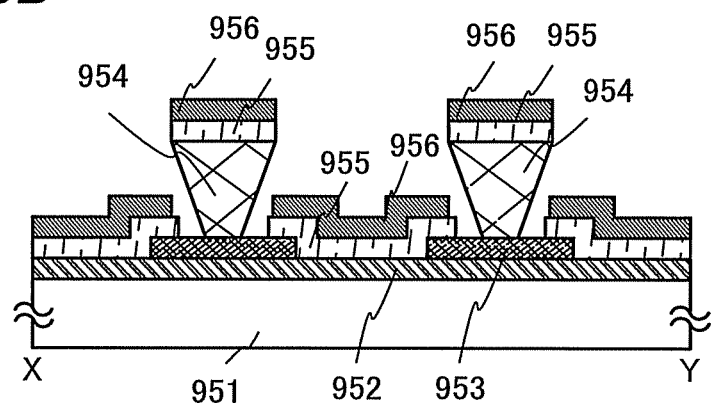

Although an active matrix light-emitting device which controls driving of a light-emitting element with a transistor is thus described in Embodiment 5, the light-emitting device may be a passive matrix light-emitting device. FIGS. 6A and 6B illustrate a passive matrix light-emitting device fabricated using any of the carbazole derivatives according to an embodiment of the present invention. In FIGS. 6A and 6B, a layer 955 including a light-emitting substance is provided between an electrode 952 and an electrode 956 over a substrate 951. An end portion of the electrode 952 is covered with an insulating layer 953. In addition, a partition layer 954 is provided over the insulating layer 953.

The sidewalls of the partition layer 954 slope so that the distance between one sidewall and the other sidewall gradually decreases toward the surface of the substrate. In other words, a cross section taken along the direction of the short side of the partition layer 954 is trapezoidal, and the lower side (a side in contact with the insulating layer 953, which is one of a pair of parallel sides of the trapezoidal cross section) is shorter than the upper side (a side not in contact with the insulating layer 953, which is the other of the pair of parallel sides). By the provision of the partition wall layer 954 in this manner, defects of the light-emitting element due to static charge or the like can be prevented. Also in the case of a passive matrix light-emitting device, by including a light-emitting element according to an embodiment of the present invention, a highly reliable light-emitting device can be obtained.

[Embodiment 6]

In Embodiment 6, electronic devices each including a light-emitting device described in Embodiment 5 will be described. The electronic devices of Embodiment 6 each have a highly reliable display portion including any of the carbazole derivatives described in Embodiment 1.

Examples of these electronic devices having a light-emitting element formed using any of the carbazole derivatives include cameras such as video cameras and digital cameras, goggle type displays, navigation systems, audio replay devices (e.g., car audio systems and audio systems), computers, game machines, portable information terminals (e.g., mobile computers, cellular phones, portable game machines, and electronic book readers), image replay devices in which a recording medium is provided (specifically, devices that are capable of replaying recording media such as DVDs (digital versatile discs) and equipped with a display device that can display an image), and the like. Specific examples of such electronic devices are illustrated in FIGS. 7A to 7D.

Figure 7A:
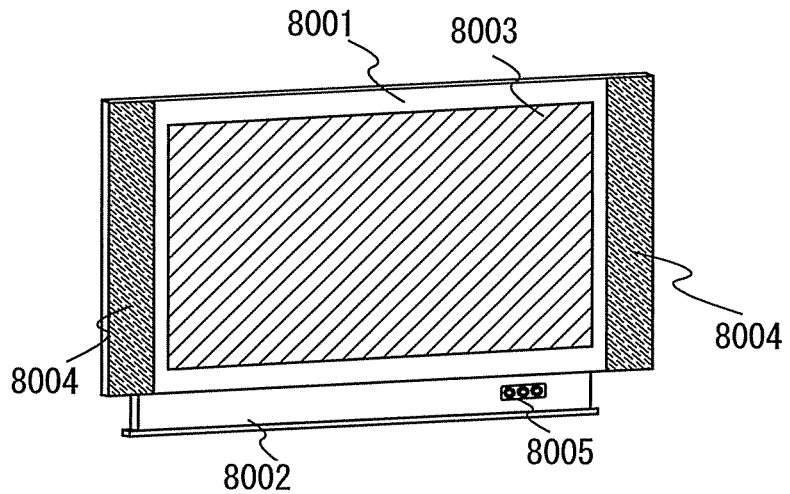
FIGS. 7A to 7D each illustrate an electronic device according to an embodiment of the present invention.

FIG. 7A illustrates a display device according to Embodiment 6, which includes a housing 8001, a supporting base 8002, a display portion 8003, a speaker portion 8004, video input terminals 8005, and the like. Note that the category of the display device includes all types of information display devices, for example, display devices for a personal computer, display devices for TV broadcast reception, display devices for advertisement display, and the like. In this display device, the display portion 8003 has light-emitting elements similar to those described in Embodiment 2 or Embodiment 3, which are arranged in matrix.

A feature of each light-emitting element is high reliability. The display portion 8003 including the light-emitting elements has a similar feature. Accordingly, in this display device, the amount of image display deterioration is small, and reliability is improved. With such a feature, a circuit having a function of compensating for deterioration or power supply circuits in the display device can be significantly reduced or downsized; accordingly, a reduction in the size and weight of the housing 8001 or the supporting base 8002 can be achieved.

Figure 7B:
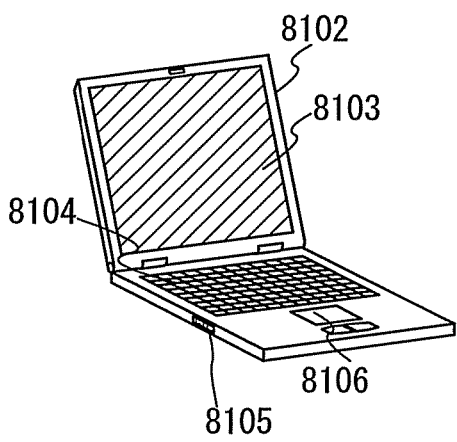

FIG. 7B illustrates a computer according to Embodiment 6, which includes a housing 8102, a display portion 8103, a keyboard 8104, an external connection port 8105, a pointing device 8106, and the like. In this computer, the display portion 8103 includes light-emitting elements similar to those described in Embodiment 2 or Embodiment 3, which are arranged in matrix. A feature of each light-emitting element is high reliability. The display portion 8103 including the light-emitting elements has a similar feature. Accordingly, in this computer, the amount of image display deterioration is small, and reliability is improved. With such a feature, a circuit having a function of compensating for deterioration or power supply circuits in the computer can be significantly reduced or downsized; accordingly, a reduction in the size and weight of the computer can be achieved.

Figure 7C:
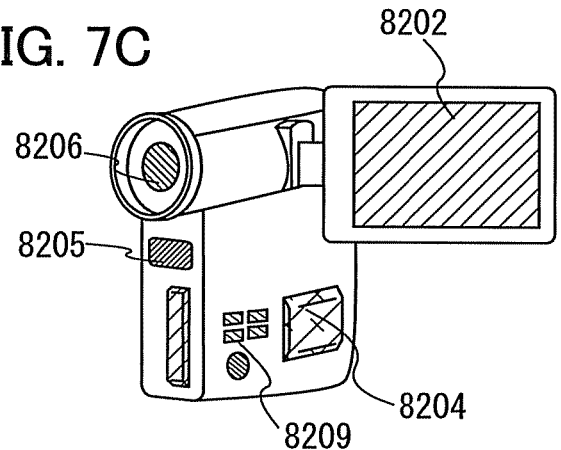

FIG. 7C illustrates a video camera according to Embodiment 6, which includes a display portion 8202, an external connection port 8204, a remote control receiving portion 8205, an image receiving portion 8206, operation keys 8209, and the like. In this video camera, the display portion 8202 includes light-emitting elements similar to those described in Embodiment 2 or Embodiment 3, which are arranged in matrix. A feature of each light-emitting element is high reliability. The display portion 8202 including the light-emitting elements has a similar feature. Accordingly, in this video camera, the amount of image display deterioration is small, and reliability is improved. With such a feature, a circuit having a function of compensating for deterioration or power supply circuits in the video camera can be significantly reduced or downsized; accordingly, a reduction in size and weight can be achieved. Thus, a product that is suitable for being carried around can be provided.

Figure 7D:
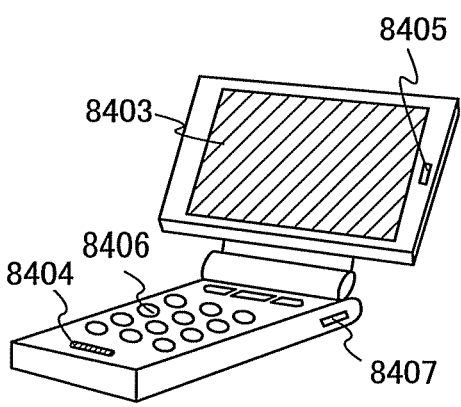

FIG. 7D illustrates a cellular phone according to Embodiment 6, which includes a display portion 8403, an audio input portion 8404, an audio output portion 8405, operation keys 8406, an external connection port 8407, and the like. In this cellular phone, the display portion 8403 includes light-emitting elements similar to those described in Embodiment 2 or Embodiment 3, which are arranged in matrix. A feature of each light-emitting element is high reliability. The display portion 8403 including the light-emitting elements has a similar feature. Accordingly, in this cellular phone, the amount of image display deterioration is small, and reliability is improved. With such a feature, a circuit having a function of compensating for deterioration or power supply circuits in the cellular phone can be significantly reduced or downsized; accordingly, a reduction in the size and weight of the main body can be achieved. In the cellular phone according to Embodiment 6, high image quality and a reduction in size and weight are achieved. Accordingly, a product that is suitable for being carried around can be provided.

As described above, the applicable range of a light-emitting device according to an embodiment of the present invention is wide so that this light-emitting device can be applied to electronic devices in a variety of fields. With the use of any of the carbazole derivatives according to an present invention, an electronic device including a highly reliable display portion can be provided. Further, the light-emitting device according to the embodiment of the present invention can also be used as a lighting device. An example in which a light-emitting element according to an embodiment of the present invention is used for a lighting device will be described using FIG. 8.

Figure 8:
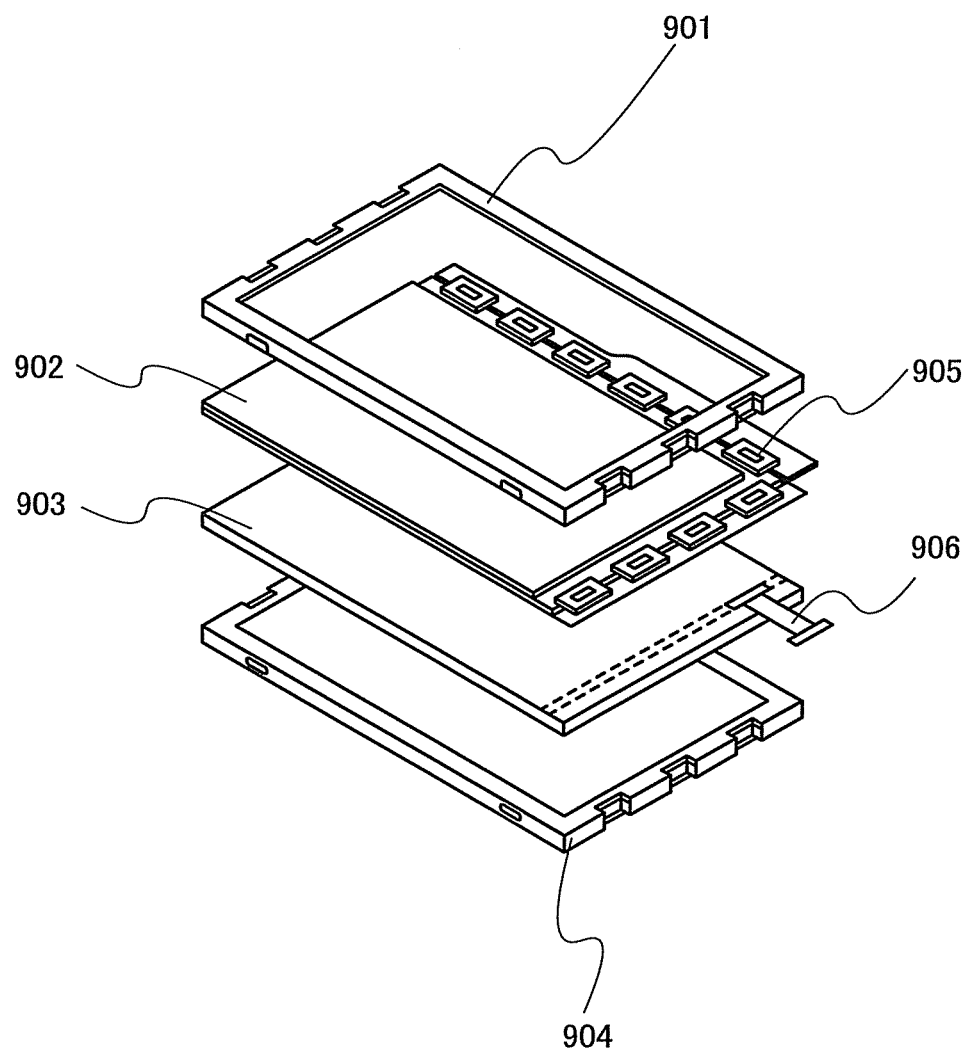
FIG. 8 illustrates an electronic device according to an embodiment of the present invention.

FIG. 8 illustrates an example of a liquid crystal display device in which a light-emitting device according to an embodiment of the present invention is used as a backlight. The liquid crystal display device illustrated in FIG. 8 includes a housing 901, a liquid crystal layer 902, a backlight 903, and a housing 904, and the liquid crystal layer 902 is connected to a driver IC 905. In addition, the light-emitting device according to the embodiment of the present invention is used as the backlight 903, and a current is supplied by a terminal 906.

By using a light-emitting device according to an embodiment of the present invention as a backlight of a liquid crystal display device, the highly reliable backlight can be obtained. Further, the light-emitting device according to the embodiment of the invention is a lighting device with plane light emission, and can have a large area. Therefore, the backlight can have a large area, and a liquid crystal display device having a large area can be obtained. Furthermore, since the light-emitting device according to the embodiment of the present invention is thin, the display device can also be thin.

Figure 9:
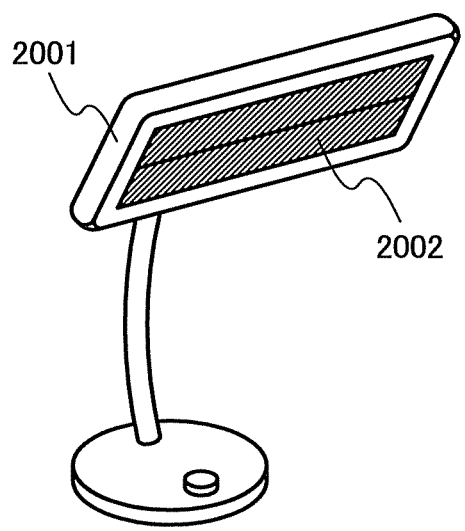
FIG. 9 illustrates a lighting apparatus according to an embodiment of the present invention.
Figure 10:
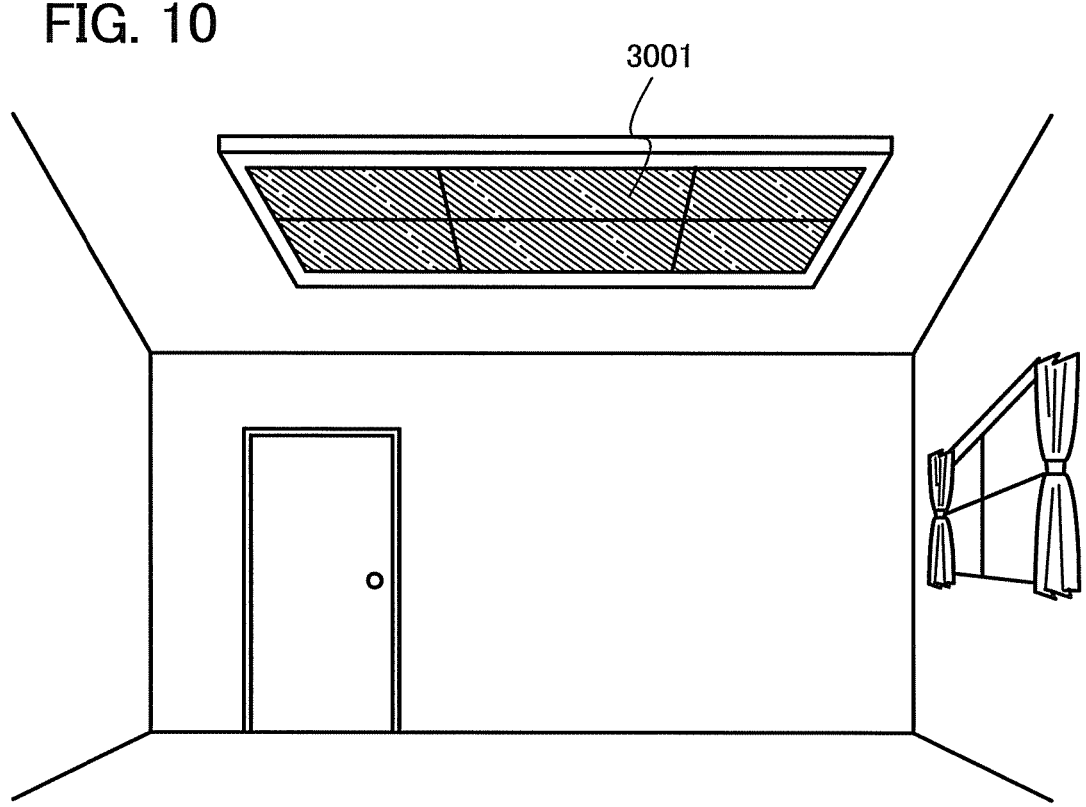
FIG. 10 illustrates a lighting apparatus according to an embodiment of the present invention.

FIG. 9 illustrates an example in which a light-emitting device according to an embodiment of the present invention is used as a desk lamp, which is one of lighting apparatus. The desk lamp illustrated in FIG. 9 includes a housing 2001 and a light source 2002, and the light-emitting device according to the embodiment of the present invention is used as the light source 2002. Since the light-emitting device according to the embodiment of the present invention is highly reliable, the desk lamp is also highly reliable. FIG. 10 illustrates an example in which a light-emitting device according to an embodiment of the present invention is used as an interior lighting apparatus 3001. Since the light-emitting device according to the embodiment of the present invention can have a large area, the light-emitting device can be used as a lighting apparatus having a large area. Furthermore, since the light-emitting device according to the embodiment of the present invention is thin, the light-emitting device can be used as a lighting apparatus that is thin.

[Examples of Production of Carbazole Derivatives]

Hereinafter, Examples 1 to 7 will be described as seven examples of methods for producing carbazole derivatives according to an embodiment of the present invention. However, it is natural that the present invention is not limited to these examples and is specified in the scope of claims.

EXAMPLE 1

[Example of Production of CzPAP]

In Example 1, an example in which 3-phenyl-9-[4-(10-phenyl-9-anthryl)phenyl]-9H-carbazole (abbreviation: CzPAP) represented by the above Structural Formula 1 is produced will be described. The synthesis reaction of this example includes two steps: Step 1 and Step 2.

[Step 1]

This step is a step of synthesizing 3-bromo-9-[4-(10-phenyl-9-anthryl)phenyl]-9H-carbazole. Step 1 is illustrated in Reaction Formula (E1-1) and will be detailed hereinbelow.

Reaction Formula (E1-1)

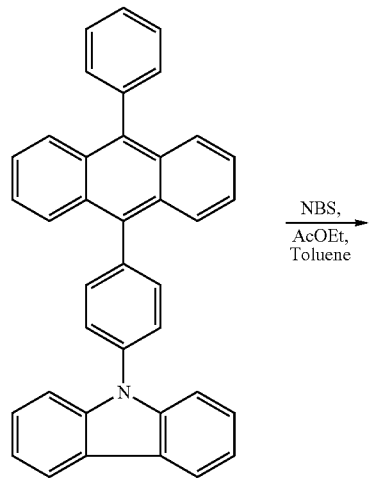

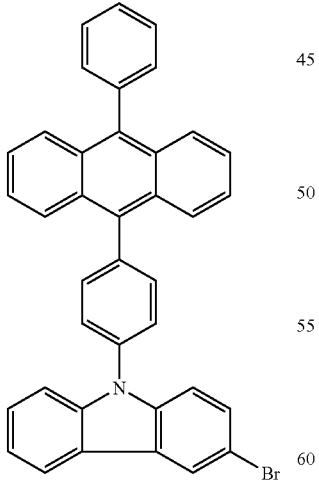

In a 1 L Erlenmeyer flask were added 5.0 g (10 mmol) of 9-[4-(10-phenyl-9-anthryl)phenyl]-9H-carbazole (abbreviation: CzPA), 600 mL of ethyl acetate, and 150 mL of toluene. This mixture was heated to about 50° C. or more and stirred to confirm dissolution of CzPA. To this solution was added 1.8 g (10 mmol) of N-bromosuccinimide (NBS). This solution was stirred at room temperature for 5 days under air.

After the solution was stirred, about 150 mL of an aqueous sodium thiosulfate solution was added to this solution, and the resulting solution was stirred for 1 hour. The organic layer of this mixture was washed with water, and the aqueous layer was extracted with toluene. The extract and the organic layer were combined and washed with saturated brine. The organic layer was dried with magnesium sulfate, and this mixture was gravity filtered. The resulting filtrate was concentrated to give a light yellow solid. The solid obtained was recrystallized with a mixed solvent of toluene and hexane to give the desired substance as 5.2 g of a light yellow powder in a yield of 90%.

[Step 2]

This step is a step of synthesizing 3-phenyl-9-[4-(10-phenyl-9-anthryl)phenyl]-9H-carbazole (abbreviation: CzPAP). The step is illustrated in Reaction Formula (E1-2) and will be detailed hereinbelow.

Reaction Formula (E1-2)

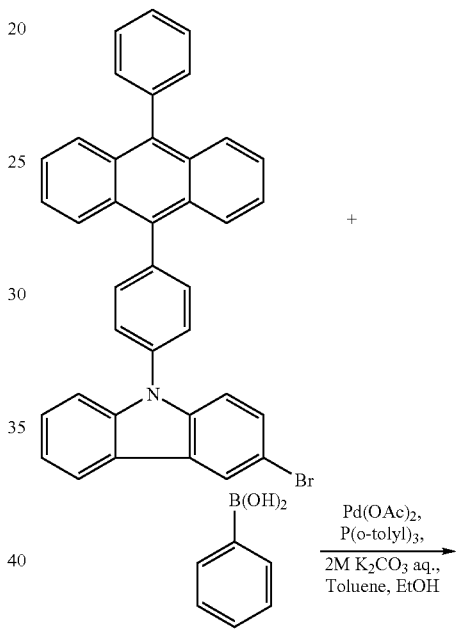

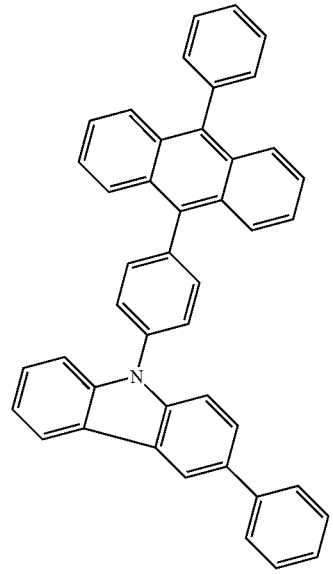

Structual Formula 1

In a 300 mL three neck flask were put 3.5 g (6.1 mmol) of 3-bromo-9-[4-(10-phenyl-9-anthryl)phenyl]-9H-carbazole, 0.74 g (6.1 mmol) of phenylboronic acid, and 0.36 g (1.2 mmol) of tri(ortho-tolyl)phosphine. The atmosphere in the flask was replaced with nitrogen. To this mixture were added 60 mL of toluene, 20 mL of ethanol, and 5.0 mL of an aqueous potassium carbonate solution (2.0 mol/L). This mixture was stirred to be degassed while the pressure was reduced. To this mixture was added 55 mg (0.24 mmol) of palladium(II) acetate. This mixture was stirred under a nitrogen stream at 80° C. for 2 hours.

After this mixture was stirred, the aqueous layer of this mixture was extracted with toluene. The extract and the organic layer were combined and washed with saturated brine. The organic layer was dried with magnesium sulfate, and this mixture was gravity filtered. An oily substance obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). An oily substance obtained by concentration of the resulting filtrate was purified by silica gel column chromatography (the developing solvent was a mixed solvent of a 5:1 ratio of hexane to toluene) to give a light yellow solid.

This light yellow solid was recrystallized with a mixed solvent of toluene and hexane to give the desired substance as 1.3 g of a light yellow powder in a yield of 37%. Sublimation purification of 1.3 g of the light yellow powder obtained was performed by a train sublimation method. The light yellow powder was heated at 270° C. with an argon flow rate of 4.0 mL/min under reduced pressure. After the sublimation purification, 1.2 g of a light yellow solid which was the desired compound was obtained in a yield of 89%.

By a nuclear magnetic resonance (NMR) method, this compound was confirmed to be 3-phenyl-9-[4-(10-phenyl-9-anthryl)phenyl]-9H-carbazole (abbreviation: CzPAP) which was the desired compound. The following are data of the $^1$H NMR measurement of the compound obtained: $^1$H NMR (CDCl$_3$, 300 MHz):δ=7.35-7.66 (m, 14H), 7.69-7.78 (m, 9H), 7.86 (d, J=8.1 Hz, 4H), 8.25 (d, J=7.8 Hz, 1H), 8.42 (s, 1H)

Figure 11A:
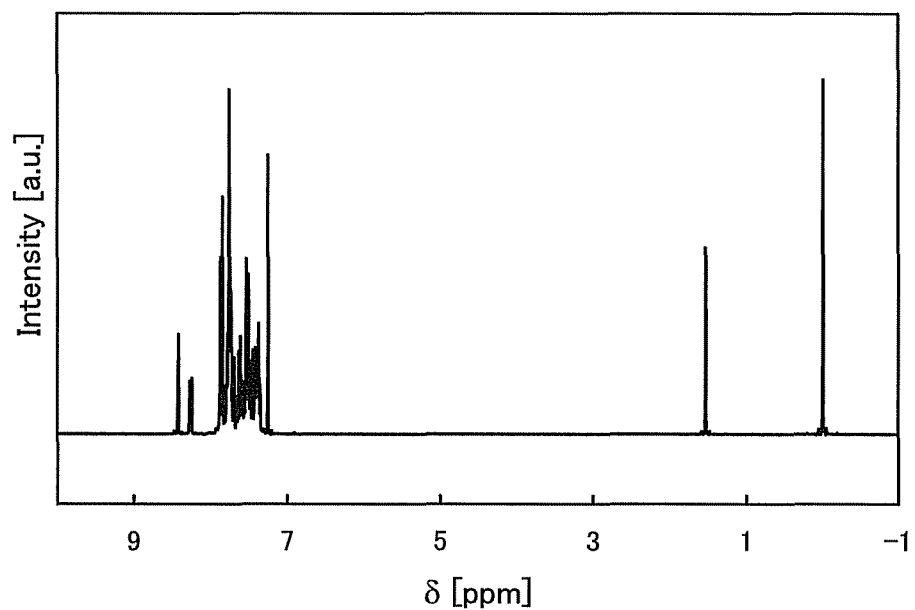
FIGS. 11A and 11B show ¹H NMR charts of CzPAP.
Figure 11B:
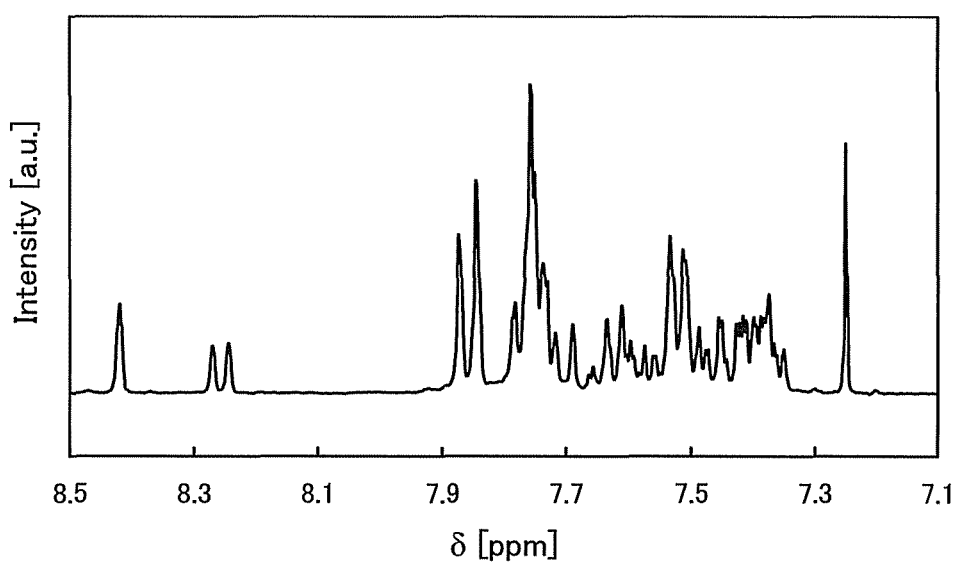

In addition, FIGS. 11A and 11B show $^1$H NMR charts. Note that FIG. 11B is a chart showing an enlarged part in the range of 7.1 ppm to 8.5 ppm in FIG. 11A.

Further, thermogravimetry-differential thermal analysis (TG-DTA) of CzPAP which was obtained was carried out. A high vacuum differential type differential thermal balance (TG-DTA2410SA, manufactured by Bruker AXS K.K.) was used. Accordingly, the temperature at which the weight was reduced to 95% of the weight at the start of the measurement (5% weight loss temperature) at atmospheric pressure was 404° C. This demonstrates that CzPAP has significantly high heat resistance.

Figure 12:
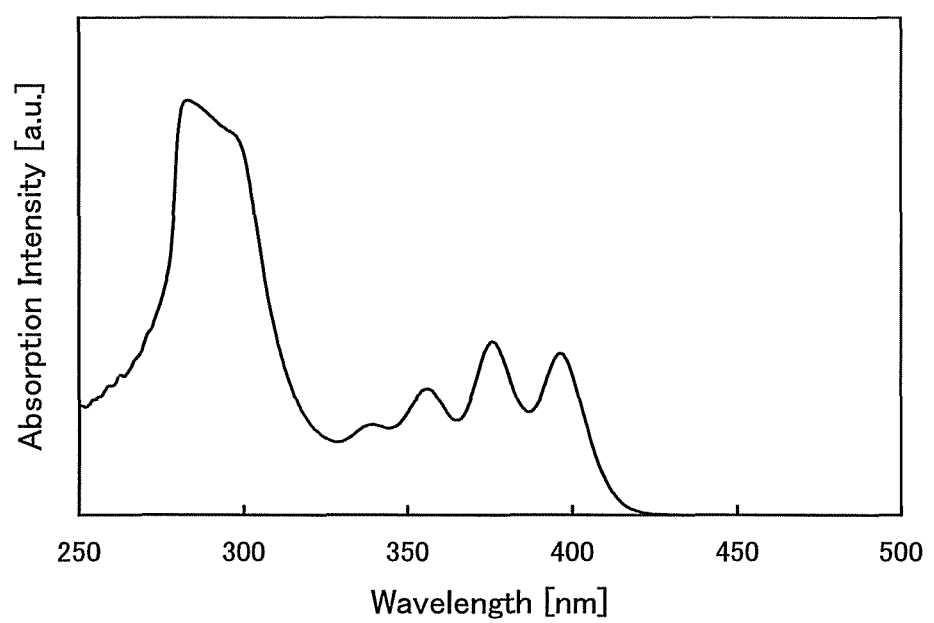
FIG. 12 shows an absorption spectrum of a toluene solution of CzPAP.
Figure 13:
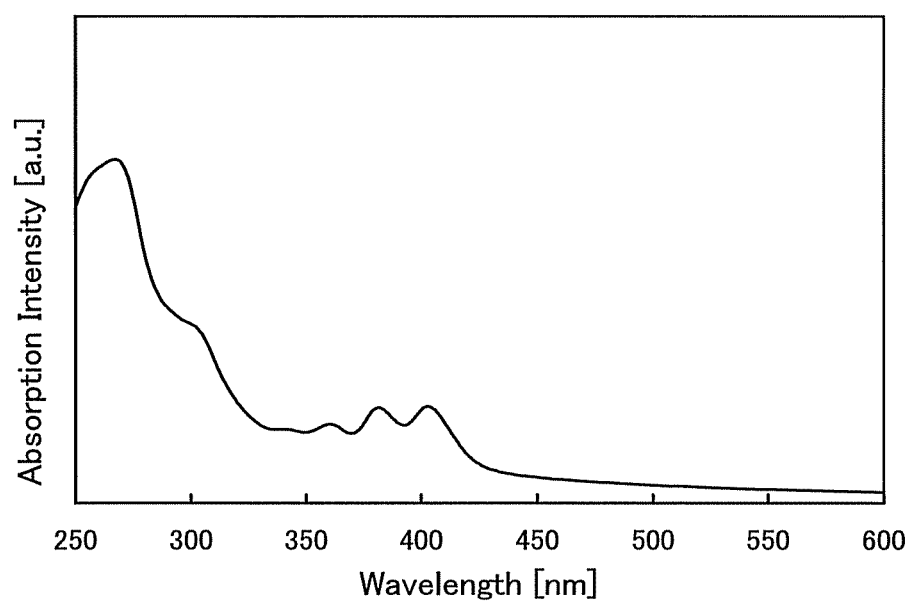
FIG. 13 shows an absorption spectrum of a thin film of CzPAP.

FIG. 12 shows an absorption spectrum of a toluene solution of CzPAP, and FIG. 13 shows an absorption spectrum of a thin film of CzPAP. An ultraviolet-visible spectrophotometer (V-550, manufactured by JASCO Corporation) was used for the measurement. The solution was put to a quartz cell to prepare a sample, and the thin film was obtained by evaporation to a quartz substrate to prepare a sample. FIG. 12 and FIG. 13 show the absorption spectrum of the toluene solution which was obtained by subtracting the absorption spectrum of a quartz cell that includes only toluene and the absorption spectrum of the thin film which was obtained by subtracting the absorption spectrum of the quartz substrate, respectively. In FIG. 12 and FIG. 13, the horizontal axis represents wavelength (nm) and the vertical axis represents absorption intensity (arbitrary unit). In the case of the toluene solution, absorption was observed at around 340 nm, 357 nm, 376 nm, and 397 nm. In the case of the thin film, absorption was observed at around 268 nm, 303 nm, 341 nm, 361 nm, 382 nm, and 403 nm.

Figure 14:
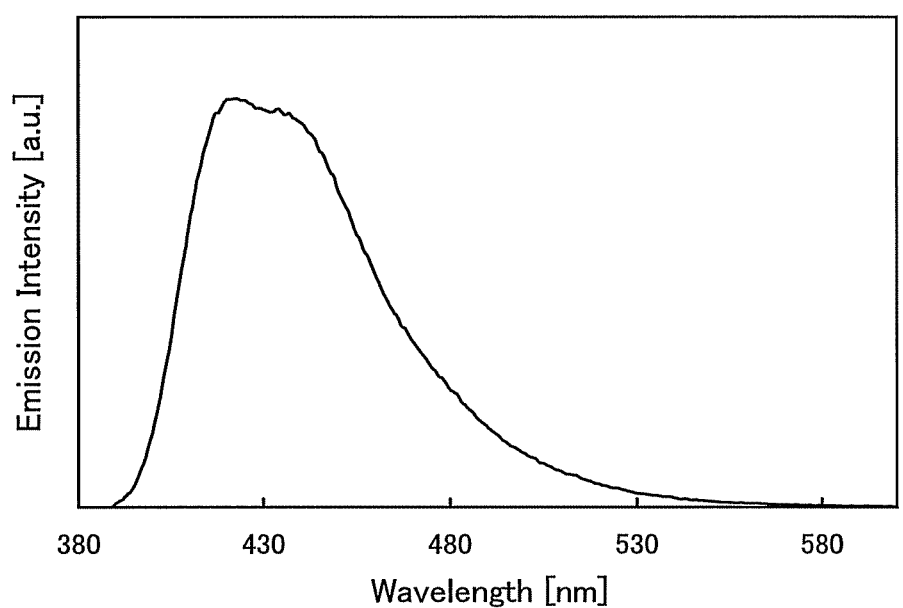
FIG. 14 shows an emission spectrum of a toluene solution of CzPAP.
Figure 15:
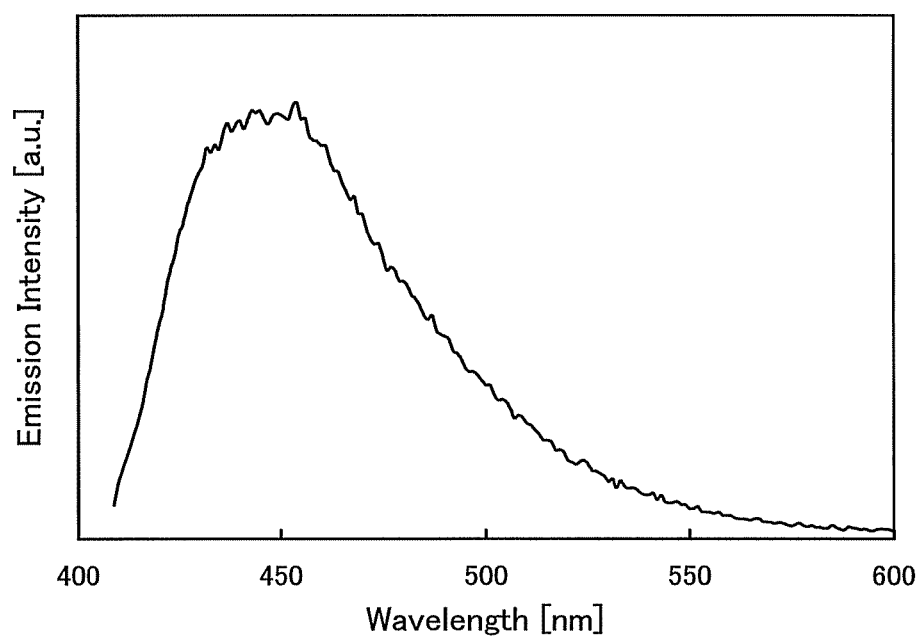
FIG. 15 shows an emission spectrum of a thin film of CzPAP.

Further, FIG. 14 shows an emission spectrum of the toluene solution of CzPAP (an excitation wavelength of 372 nm). FIG. 15 shows an emission spectrum of the thin film of CzPAP (an excitation wavelength of 399 nm). In FIGS. 14 and 15, the horizontal axis represents wavelength (nm) and the vertical axis represents emission intensity (arbitrary unit). In the case of the toluene solution, the maximum emission wavelength was 423 nm (an excitation wavelength of 372 nm). In the case of the thin film, the maximum emission wavelength was 444 nm (an excitation wavelength of 399 nm).

In addition, by measurement of a thin film of CzPAP in an atmosphere using a photoelectron spectrometer (AC-2, manufactured by Riken Keiki Co., Ltd.), the HOMO level was −5.84 eV. Furthermore, with the use of the absorption spectrum data of the thin film of CzPAP in FIG. 13, the absorption edge was obtained by a Tauc plot assuming direct transition. The absorption edge was estimated as an optical energy gap, whereby the energy gap was 2.94 eV. The LUMO level estimated from the HOMO level and the energy gap of CzPAP was −2.90 eV.

Further, the oxidation-reduction characteristics of CzPAP were measured by cyclic voltammetry (CV). Note that an electrochemical analyzer (ALS model 600A, a product of BAS Inc.) was used. For a solution used in the CV measurement, dehydrated dimethylformamide (DMF, produced by Sigma-Aldrich Inc., 99.8%, Catalog No. 22705-6) was used as a solvent.

At that time, tetra-n-butylammonium perchlorate (n-Bu$_4$NClO$_4$, produced by Tokyo Chemical Industry Co., Ltd., Catalog No. T0836), which was a supporting electrolyte, was dissolved in the solvent such that the concentration of tetra-n-butylammonium perchlorate was 100 mmol/L. Furthermore, the substance that is to be measured was dissolved in the solution such that the concentration thereof was 1 mmol/L. In addition, a platinum electrode (PIE platinum electrode, produced by BAS Inc.) was used as a working electrode, a platinum electrode (Pt counter electrode for VC-3, (5 cm), produced by BAS Inc.) was used as an auxiliary electrode, and an Ag/Ag$^+$ electrode (RES reference electrode for nonaqueous solvent, produced by BAS Inc.) was used as a reference electrode. Note that the measurement was conducted at room temperature.

The oxidation characteristics of CzPAP were examined by 100 cycles of measurements in which a scan for changing the potential of the working electrode with respect to the reference electrode from −0.01 V to 1.15 V and then from 1.15 V to −0.01 V was set to one cycle. Note that the scan rate for the CV measurements was set to 0.1 V/s. Further, the reduction characteristics of CzPAP were examined by 100 cycles of measurements in which a scan for changing the potential of the working electrode with respect to the reference electrode from −1.45 V to −2.35 V and then from −2.35 V to −1.45 V was set to one cycle. Note that the scan rate for the CV measurements was set to 0.1 V/s.

Figure 16:
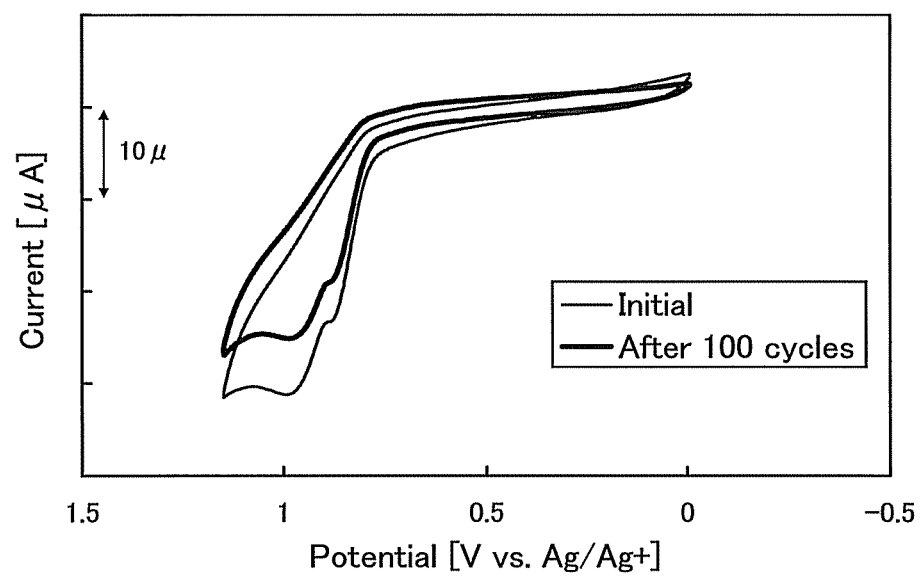
FIG. 16 shows CV measurement results of CzPAP.
Figure 17:
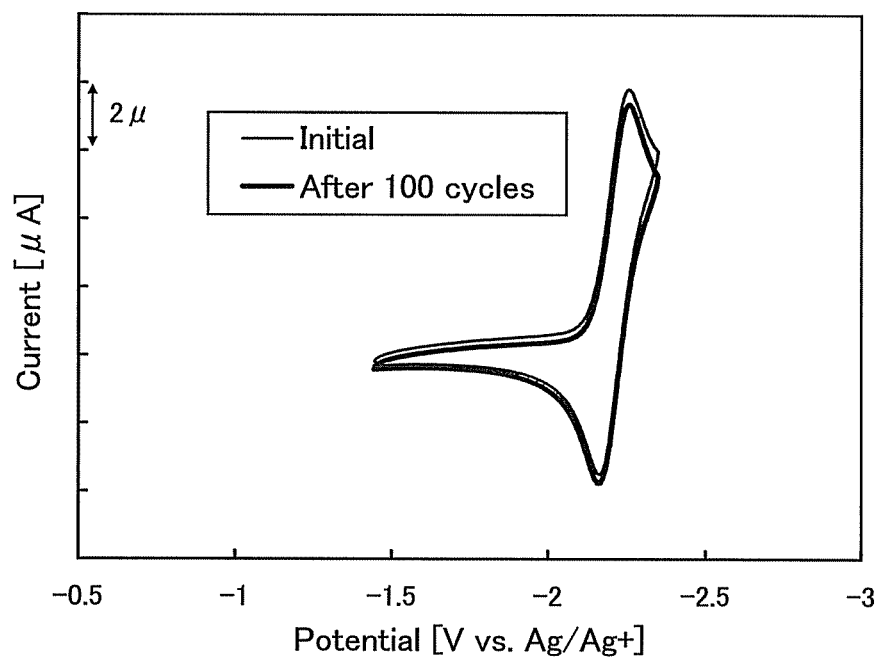
FIG. 17 shows CV measurement results of CzPAP.

FIG. 16 shows CV measurement results of the oxidation characteristics of CzPAP, and FIG. 17 shows CV measurement results of the reduction characteristics of CzPAP. In FIGS. 16 and 17, the horizontal axis represents potential (V) of the working electrode with respect to the reference electrode, and the vertical axis represents value of a current (μA) flowing between the working electrode and the auxiliary electrode. From FIG. 16, a current exhibiting oxidation is observed at around +0.84 V (vs. the Ag/Ag$^+$ electrode). From FIG. 17, a current exhibiting reduction is observed at around −2.21 V (vs. the Ag/Ag$^+$ electrode).

After the 100 cycles of measurements in which the scan was repeated, there was no significant change in the peak position and peak intensity of the CV curves exhibiting the oxidation and reduction reactions. The peak intensity for the oxidation characteristics maintained 82% of the initial state, and the peak intensity for the reduction characteristics maintained 94% of the initial state. Accordingly, it is found that the carbazole derivative according to Example 1 is stable to repetitive oxidation-reduction reactions.

Examples in which CzPAP produced in Example 1 is produced by each of the first and second known production methods described above will be described below. These examples are described for comparison and reference. Comparative Example 1 corresponds to the first known method, and Comparative Example 2 corresponds to the second known method.

COMPARATIVE EXAMPLE 1

Synthesis of CzPAP by First Known Method

In Comparative Example 1, an example will be described in which 3-phenyl-9-[4-(10-phenyl-9-anthryl)phenyl]-9H-carbazole (abbreviation: CzPAP) represented by Structural Formula 1 is produced by the first known method which is a known production method, as described above.

[Step 1]

This step is a step of synthesizing 3-phenyl-9H-carbazole. The step is illustrated in Reaction Formula (R1-1) and will be detailed hereinbelow.

In a 100 mL three neck flask were put 0.50 g (2.0 mmol) of 3-bromo-9H-carbazole, 0.25 g (2.0 mmol) of phenylboronic acid, and 0.15 g (0.50 mmol) of tri(ortho-tolyl)phosphine. The atmosphere in the flask was replaced with nitrogen. To this mixture were added 30 mL of toluene, 10 mL of ethanol, and 2.0 mL of an aqueous potassium carbonate solution (2.0 mol/L). This mixture was stirred to be degassed while the pressure was reduced. To this mixture was added 23 mg (0.10 mmol) of palladium(II) acetate. This mixture was stirred under a nitrogen stream at 80° C. for 2 hours.

After this mixture was stirred, the aqueous layer was extracted with toluene. The extract and the organic layer were combined and washed with saturated brine. Then, the mixture was separated into an aqueous layer and an organic layer. The organic layer was dried with magnesium sulfate, and this mixture was gravity filtered. A solid obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). The resulting filtrate was concentrated to give a white solid. This solid was recrystallized with a mixed solvent of toluene and hexane to give the desired substance as 0.23 g of a white powder in a yield of 47%.

[Step 2]

This step is a step of synthesizing 3-phenyl-9-[4-(10-phenyl-9-anthryl)phenyl]-9H-carbazole (abbreviation: CzPAP). The step is illustrated in Reaction Formula (R1-2) and will be detailed hereinbelow.

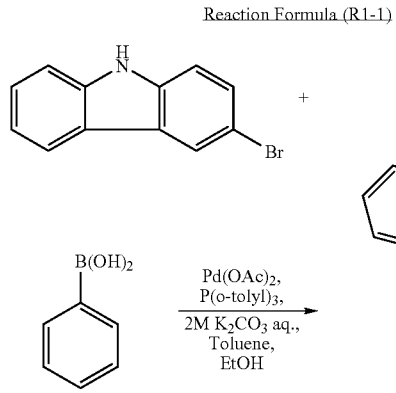

Reaction Formula (R1-1)

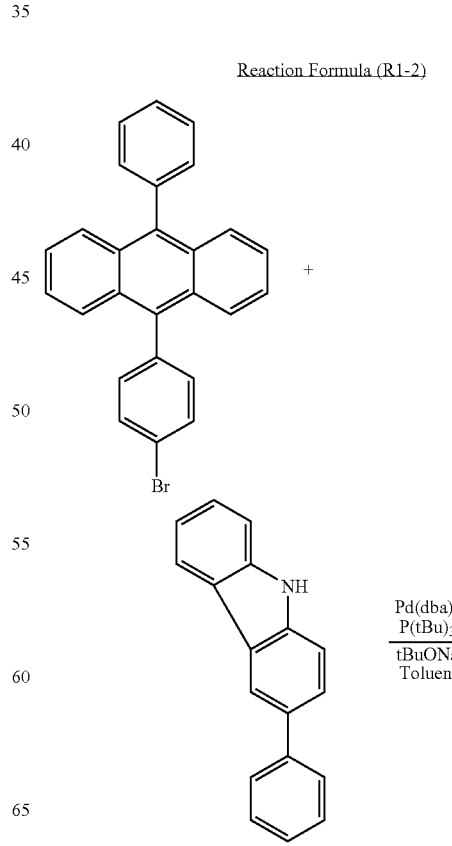

Reaction Formula (R1-2)

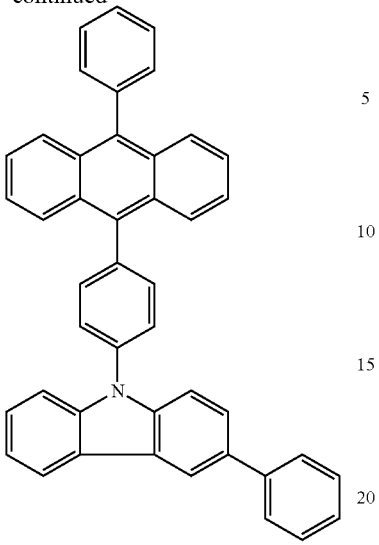

Structual Formula I

In a 100 mL three neck flask were put 0.39 g (0.94 mmol) of 9-(4-bromophenyl)-10-phenylanthracene, 0.23 g (0.94 mmol) of 3-phenyl-9H-carbazole, and 0.19 g (2.0 mmol) of sodium tert-butoxide. The atmosphere in the flask was replaced with nitrogen. Then, to this mixture were added 20 mL of toluene and 0.20 mL of a solution of tri(tert-butyl) phosphine (10 wt %) in hexane. This mixture was stirred to be degassed while the pressure was reduced. After that, 27 mg (0.047 mmol) of bis(dibenzylideneacetone)palladium(0) was added to the mixture.

This mixture was stirred under a nitrogen stream at 110° C. for 2 hours. Then, this mixture was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). A solid obtained by concentration of the resulting filtrate was purified by silica gel column chromatography (the developing solvent was a mixed solvent of a 5:1 ratio of hexane to toluene). The light yellow solid obtained was recrystallized with a mixed solvent of toluene and hexane to give the desired compound as 0.44 g of a light yellow powder in a yield of 81%.

As in Example of Production of CzPAP in Example 1, by a nuclear magnetic resonance (NMR) method, this compound was confirmed to be 3-phenyl-9-[4-(10-phenyl-9-anthryl) phenyl]-9H-carbazole (abbreviation: CzPAP) which was the desired compound.

COMPARATIVE EXAMPLE 2

Synthesis of CzPAP by Second Known Method

In Comparative Example 2, an example will be described in which 3-phenyl-9-[4-(10-phenyl-9-anthryl)phenyl]-9H-carbazole (abbreviation: CzPAP) represented by Structural Formula 1 is produced by the second known method which is a known production method, as described above.

[Step 1]

This step is a step of synthesizing 9-(4-bromophenyl)-3-phenyl-9H-carbazole. The step is illustrated in Reaction Formula (R2-1) and will be detailed hereinbelow.

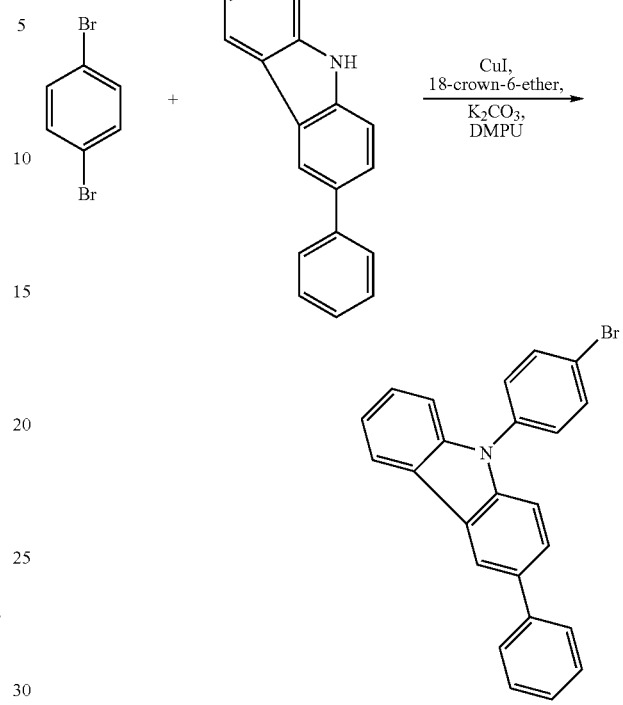

Reaction Formula (R2-1)

In a 500 mL three neck flask were put 8.0 g (34 mmol) of 1,4-dibromobenzene, 7.0 g (28 mmol) of 3-phenyl-9H-carbazole, and 0.27 g (1.0 mmol) of 18-crown-6-ether. This mixture was stirred while being heated at about 130° C., so that 1,4-dibromobenzene was melted. After that, to this mixture were added 3.0 mL of 1,3-dimethyl-3,4,5,6-tetrahydro-2(1H)-pyrimidinone (DMPU), 9.5 g (69 mmol) of potassium carbonate, and 0.20 g (1.0 mmol) of copper(I) iodide, followed by stirring at 170° C. for 3 hours. Then, this mixture was cooled to about 110° C. Next, 100 mL of toluene was added to this mixture, which was cooled to room temperature.

This mixture was suction filtered. The resulting filtrate was washed with dilute hydrochloric acid three times, with a saturated aqueous sodium hydrogen carbonate solution three times, and with saturated brine once. Then, the mixture was separated into an aqueous layer and an organic layer. The organic layer was dried with magnesium sulfate, and this mixture was gravity filtered. An oily substance obtained by concentration of the resulting filtrate was purified by silica gel column chromatography (the developing solvent was a mixed solvent of a 7:1 ratio of hexane to toluene) to give a colorless oily substance. This oily substance was melted in a small amount of hexane. Methanol was added to this mixture, followed by irradiation with ultrasonic waves to precipitate a white solid. This solid was collected by suction filtration to give the desired substance as 2.5 g of a white powder in a yield of 22%.

[Step 2]

This step is a step of synthesizing 4-(3-phenyl-9H-carbazol-9-yl)phenylboronic acid. The step is illustrated in Reaction Formula (R2-2) and will be detailed hereinbelow.

Reaction Formula (R2-2)

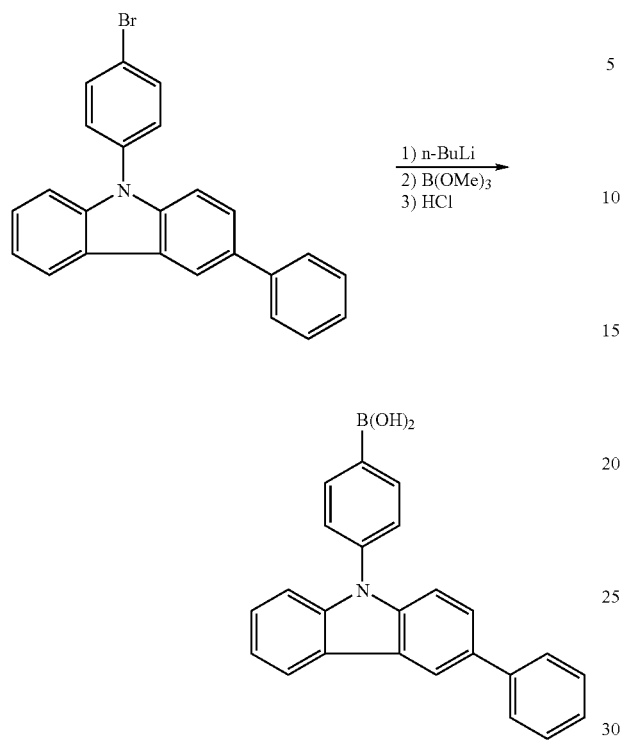

Reaction Formula (R2-3)

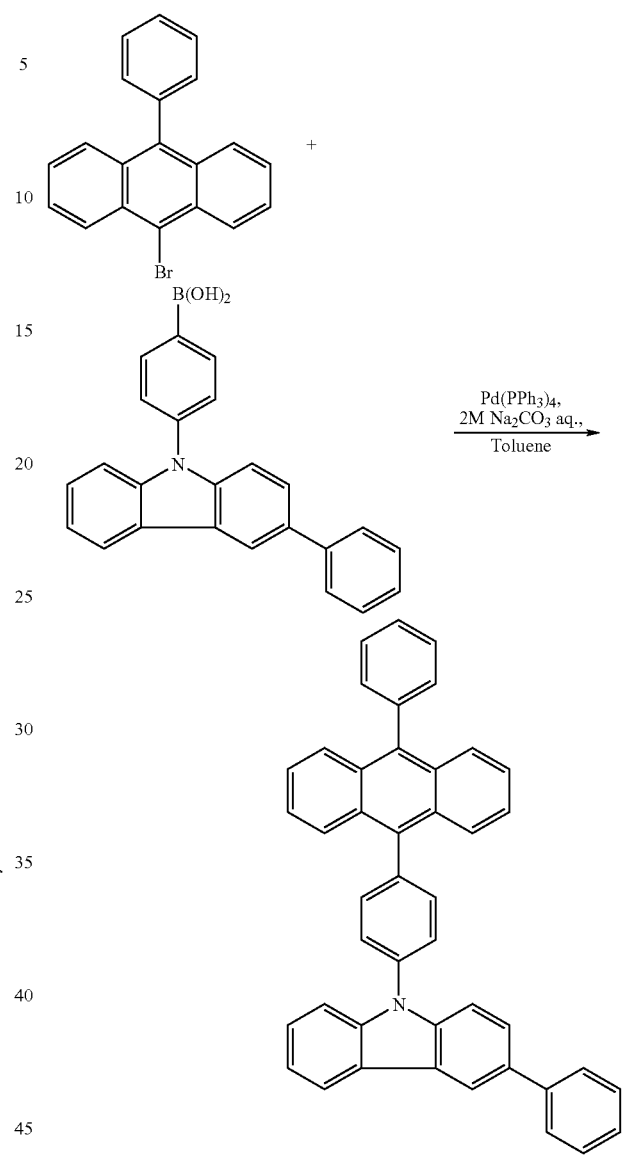

Structual Formula 1

In a 300 mL three neck flask was put 2.5 g (6.2 mmol) of 9-(4-bromophenyl)-3-phenyl-9H-carbazole. The atmosphere in the flask was replaced with nitrogen. In this flask was put 100 mL of tetrahydrofuran (THF), and this solution was cooled to −80° C. To this solution was added 4.2 mL (7.0 mmol) of a solution of n-butyllithium (1.6 mol/L) in hexane by being dripped with a syringe. After completion of dripping, this solution was stirred at the same temperature for 1 hour. Then, 0.72 mL (7.5 mmol) of trimethyl borate was added to this solution, and the mixture was stirred for 2 hours while being returned to room temperature. After that, about 50 mL of dilute hydrochloric acid (1.0 mol/L) was added to this solution, followed by stirring for 2 hours.

After being stirred, this mixture was separated into an aqueous layer and an organic layer. The aqueous layer was extracted with ethyl acetate. The extract and the organic layer were combined and washed with a saturated aqueous sodium hydrogen carbonate solution and saturated brine. The organic layer was dried with magnesium sulfate, followed by gravity filtration of this mixture. The resulting filtrate was concentrated to give an oily substance. This oily substance was melted in a small amount of chloroform. Hexane was added to this mixture, followed by irradiation with ultrasonic waves to precipitate a white solid. This solid was collected by suction filtration to give the desired substance as 1.5 g of a white powder in a yield of 67%.

[Step 3]

This step is a step of synthesizing 3-phenyl-9-[4-(10-phenyl-9-anthryl)phenyl]-9H-carbazole (abbreviation: CzPAP). The step is illustrated in Reaction Formula (R2-3) and will be detailed hereinbelow.

In a 100 mL three neck flask were put 1.4 g (4.1 mmol) of 9-bromo-10-phenylanthracene and 1.5 g (4.1 mmol) of 4-(3-phenyl-9H-carbazol-9-yl)phenylboronic acid. The atmosphere in the flask was replaced with nitrogen. Then, to this mixture were added 50 mL of toluene and 5.0 mL of an aqueous potassium carbonate solution (2.0 mol/L). The mixture was stirred to be degassed while the pressure was reduced. To this mixture was added 0.24 g (0.20 mmol) of tetrakis(triphenylphosphine)palladium(0), and the mixture was stirred under a nitrogen stream at 80° C. for 9 hours.

After being stirred, this mixture was separated into an aqueous layer and an organic layer. The aqueous layer was extracted with toluene. The extract and the organic layer were combined and washed with saturated brine. The organic layer was dried with magnesium sulfate, followed by gravity filtration of this mixture. A solid obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). An oily substance obtained by concentration of the resulting filtrate was purified by silica gel column chromatography (the developing solvent was a mixed solvent of a 5:1 ratio of hexane to toluene) to give a light yellow oily substance.

This oily substance was recrystallized with a mixed solvent of toluene and hexane to give the desired substance as 1.9 g of a light yellow powder in a yield of 83%. As in Example of Production of CzPAP, by a nuclear magnetic resonance (NMR) method, this compound was confirmed to be 3-phenyl-9-[4-(10-phenyl-9-anthryl)phenyl]-9H-carbazole (abbreviation: CzPAP) which was the desired compound.

EXAMPLE 2

[Example of Production of CzPAαNP]

In Example 2, an example in which 3-[4-(1-naphthyl)phenyl]-9-[4-(10-phenyl-9-anthryl)phenyl]-9H-carbazole (abbreviation: CzPAαNP) represented by the above Structural Formula 2 is produced will be described. The example is illustrated in Reaction Formula (E2) and will be detailed hereinbelow.

Reaction Formula (E2)

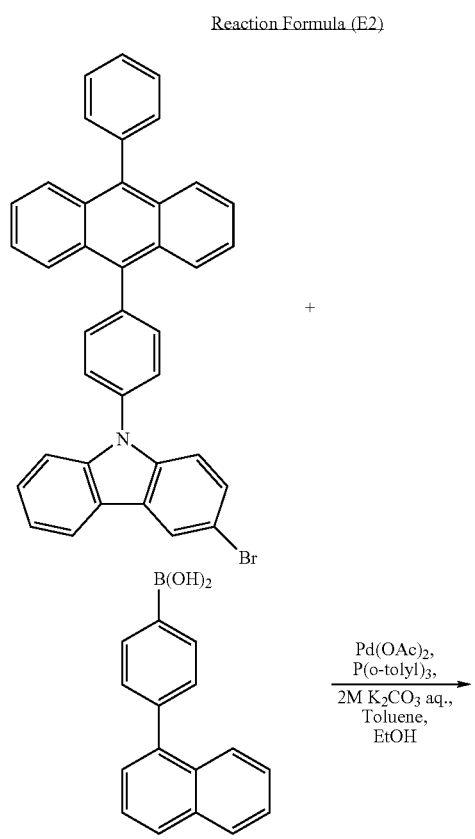

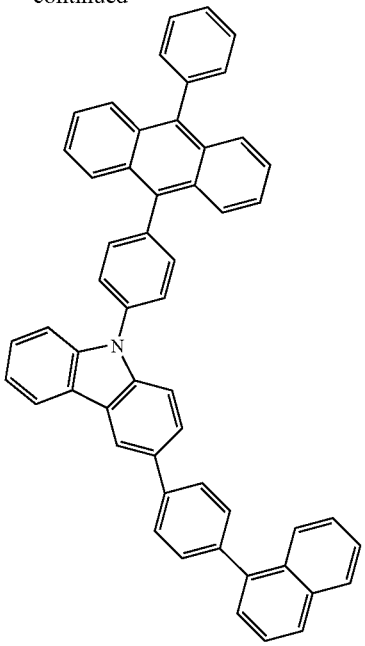

Structual Formula 2

In a 200 mL three neck flask were put 2.5 g (4.4 mmol) of 3-bromo-9-[4-(10-phenyl-9-anthryl)phenyl]-9H-carbazole, 1.1 g (4.4 mmol) of 4-(1-naphthyl)phenylboronic acid, and 0.33 g (1.1 mmol) of tri(ortho-tolyl)phosphine. The atmosphere in the flask was replaced with nitrogen. To this mixture were added 5.0 mL of an aqueous potassium carbonate solution (2.0 mol/L), 60 mL of toluene, and 20 mL of ethanol. This mixture was stirred to be degassed while the pressure was reduced. To this mixture was added 49 mg (0.22 mmol) of palladium(II) acetate. This mixture was stirred under a nitrogen stream at 80° C. for 5 hours.

After being stirred, the mixture was separated into an aqueous layer and an organic layer. The aqueous layer was extracted with toluene. The extract and the organic layer were combined and washed with saturated brine. Then, the organic layer was dried with magnesium sulfate, followed by gravity filtration of this mixture. An oily substance obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). An oily substance obtained by concentration of the resulting filtrate was purified by silica gel column chromatography (the developing solvent was a mixed solvent of a 5:1 ratio of hexane to toluene) to give a light yellow oily substance.

This oily substance was recrystallized with a mixed solvent of toluene and hexane to give the desired substance as 2.4 g of a light yellow powder in a yield of 79%. Sublimation purification of 2.3 g of the light yellow powder obtained was performed by a train sublimation method. The light yellow powder was heated at 340° C. with an argon flow rate of 4.0 mL/min under reduced pressure. After the sublimation purification, 2.2 g of a light yellow solid which was the desired substance was obtained in a yield of 95%. By a nuclear magnetic resonance (NMR) method, this compound was confirmed to be 3-[4-(1-naphthyl)phenyl]-9-[4-(10-phenyl-9-anthryl)phenyl]-9H-carbazole (abbreviation: CzPAαNP) which was the desired compound.

The following are data of the $^1$H NMR measurement of the compound obtained: $^1$H NMR (CDCl$_3$, 300 MHz):δ=7.37-7.67 (m, 17H), 7.70-7.80 (m, 6H), 7.85-7.96 (m, 9H), 8.06 (d, J=8.1 Hz, 1H), 8.29 (d, J=7.8 Hz, 1H), 8.52 (d, J=0.90 Hz, 1H)

Figure 18A:
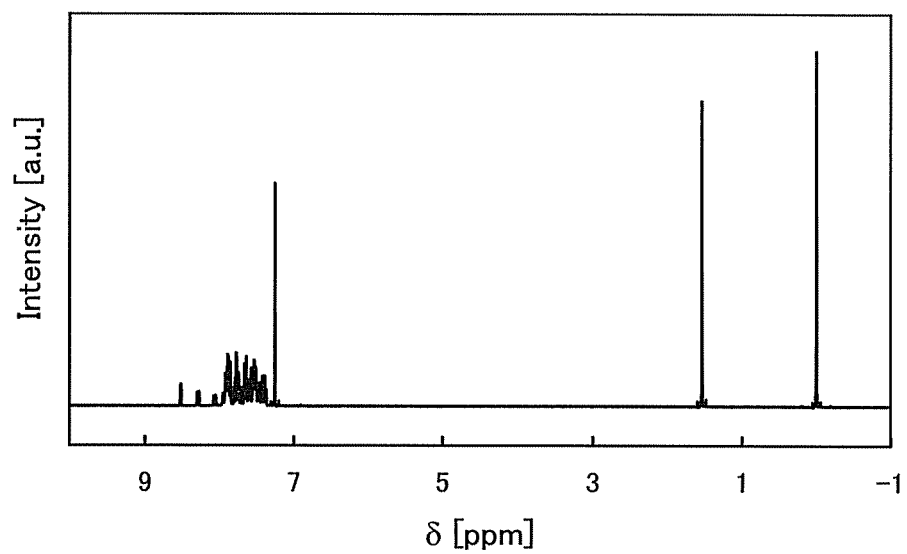
FIGS. 18A and 18B show ¹H NMR charts of CzPAαNP.
Figure 18B:
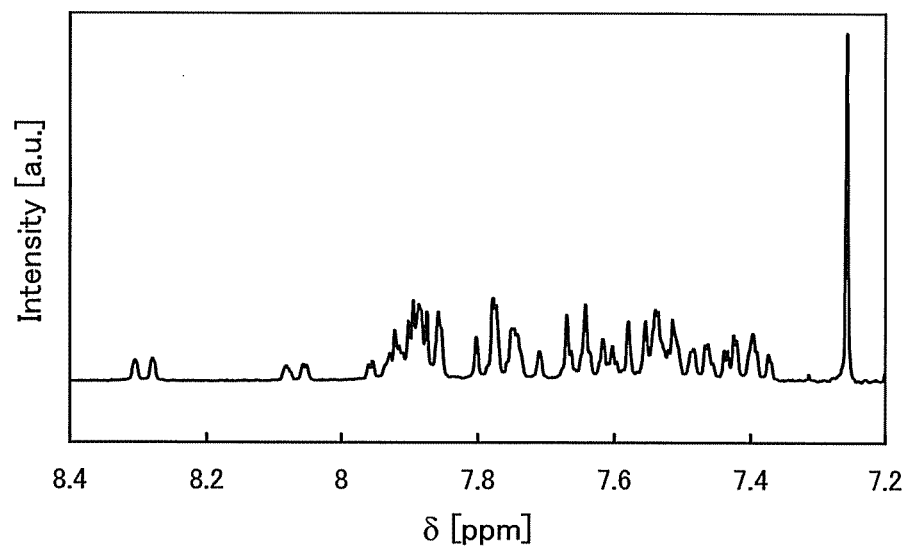

In addition, FIGS. 18A and 18B show ¹H NMR charts. Note that FIG. 18B is a chart showing an enlarged part in the range of 7.2 ppm to 8.4 ppm in FIG. 18A.

EXAMPLE 3

[Example of Production of CzPAαN]

In Example 3, an example in which 3-(1-naphthyl)-9-[4-(10-phenyl-9-anthryl)phenyl]-9H-carbazole (abbreviation: CzPAαN) represented by the above Structural Formula 4 is produced will be described. The example is illustrated in Reaction Formula (E3) and will be detailed hereinbelow.

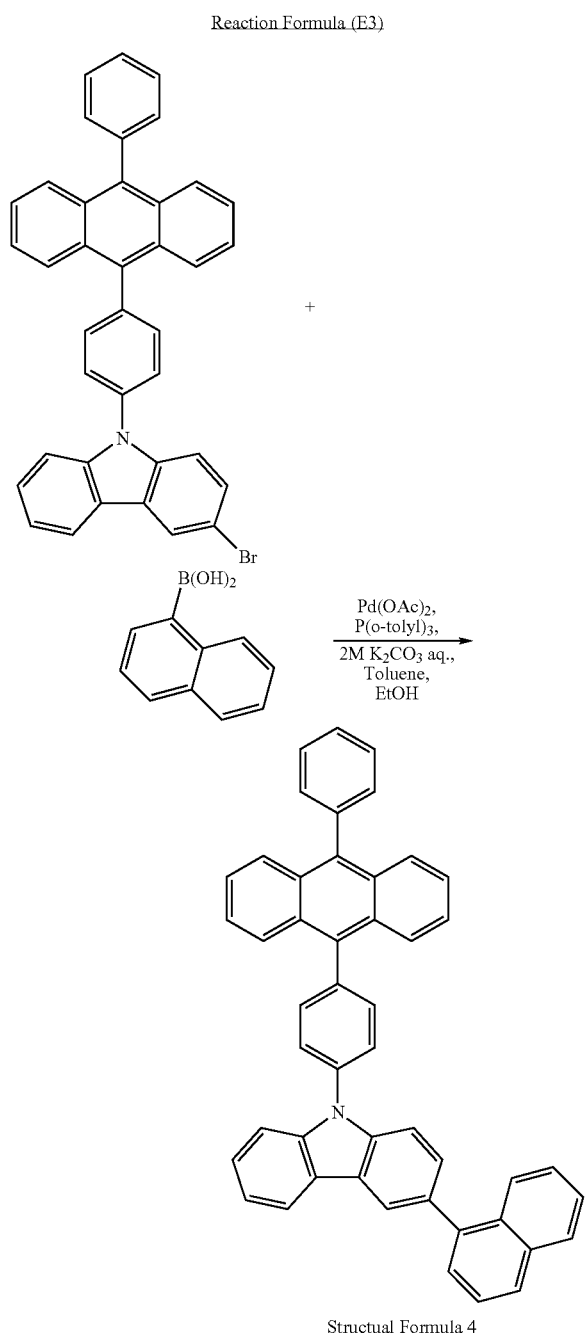

Reaction Formula (E3)

Structual Formula 4

In a 200 mL three neck flask were put 2.8 g (4.9 mmol) of 3-bromo-9-[4-(10-phenyl-9-anthryl)phenyl]-9H-carbazole, 0.84 g (4.9 mmol) of 1-naphthylboronic acid, and 0.36 g (1.2 mmol) of tri(ortho-tolyl)phosphine. The atmosphere in the flask was replaced with nitrogen. To this mixture were added 5.0 mL of an aqueous potassium carbonate solution (2.0 mol/L), 60 mL of toluene, and 20 mL of ethanol This mixture was stirred to be degassed while the pressure was reduced. To this mixture was added 55 mg (0.24 mmol) of palladium(II) acetate. The resulting mixture was stirred under a nitrogen stream at 80° C. for 4 hours. After being stirred, the mixture was separated into an aqueous layer and an organic layer. The aqueous layer was extracted with toluene. The extract and the organic layer were combined and washed with saturated brine. The organic layer was dried with magnesium sulfate, followed by gravity filtration of this mixture.

An oily substance obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). An oily substance obtained by concentration of the resulting filtrate was purified by silica gel column chromatography (the developing solvent was a mixed solvent of a 5:1 ratio of hexane to toluene) to give a light yellow oily substance. This light yellow solid obtained was recrystallized with a mixed solvent of toluene and hexane to give the desired substance as 1.8 g of a light yellow powder in a yield of 60%.

Sublimation purification of 1.8 g of the light yellow powder obtained was performed by a train sublimation method. The light yellow powder was heated at 320° C. with an argon flow rate of 4.0 mL/min under reduced pressure. After the sublimation purification, 1.7 g of a light yellow solid which was the desired substance was obtained in a yield of 94%. By a nuclear magnetic resonance (NMR) method, this compound was confirmed to be 3-(1-naphthyl)-9-[4-(10-phenyl-9-anthryl)phenyl]-9H-carbazole (abbreviation: CzPAαN).

The following are data of the ¹H NMR measurement of the compound obtained: ¹H NMR (CDCl$_3$, 300 MHz):δ=7.34-7.67 (m, 16H), 7.72-7.81 (m, 6H), 7.85-7.96 (m, 6H), 8.07 (d, J=8.4 Hz, 1H), 8.20 (d, J=7.8 Hz, 1H), 8.32 (d, J=1.5 Hz, 1H)

Figure 19A:
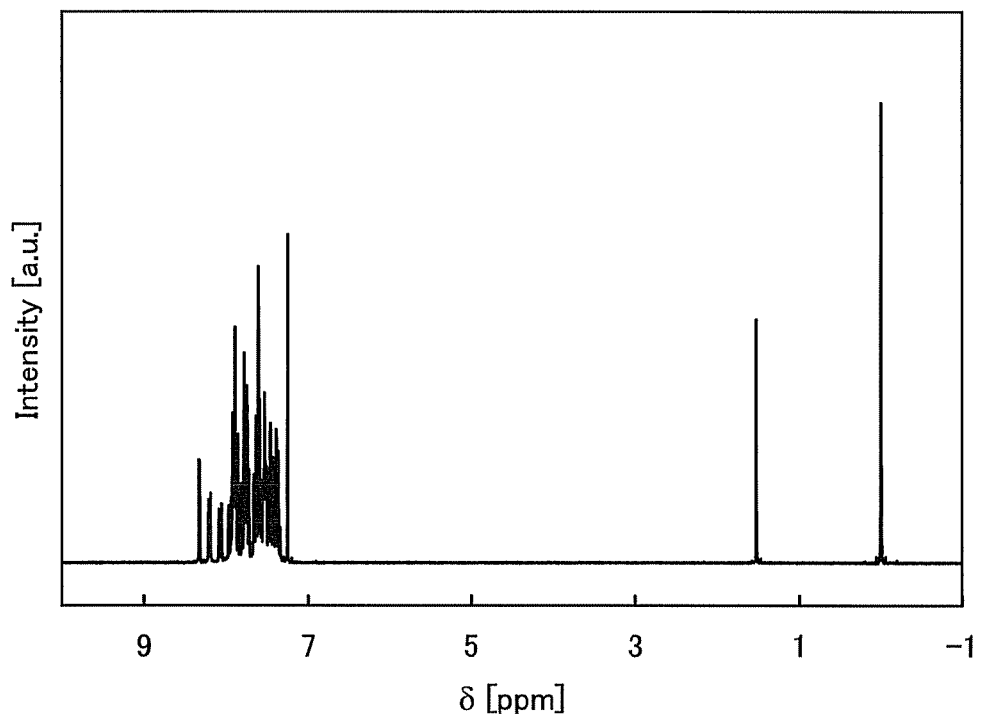
FIGS. 19A and 19B show ¹H NMR charts of CzPAαN.
Figure 19B:
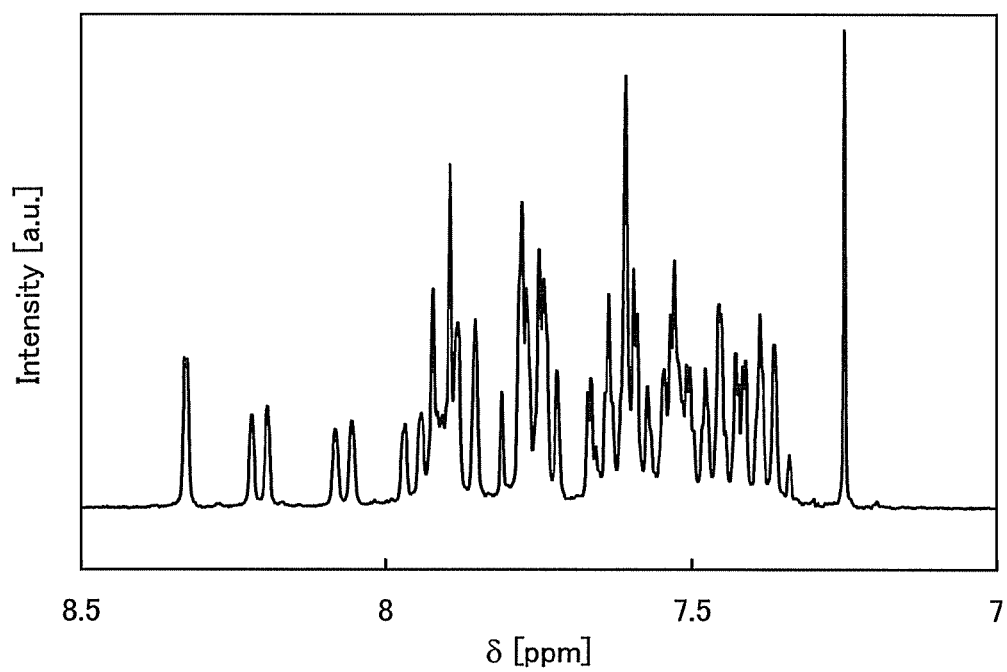

In addition, FIGS. 19A and 19B show ¹H NMR charts. Note that FIG. 19B is a chart showing an enlarged part in the range of 7.0 ppm to 8.5 ppm in FIG. 19A.

EXAMPLE 4

[Example of Production of CzPAβN]

In Example 3, an example in which 3-(2-naphthyl)-9-[4-(10-phenyl-9-anthryl)phenyl]-9H-carbazole (abbreviation: CzPAβN) represented by the above Structural Formula 5 is produced will be described. The example is illustrated in Reaction Formula (E4) and will be detailed hereinbelow.

Reaction Formula (E4)

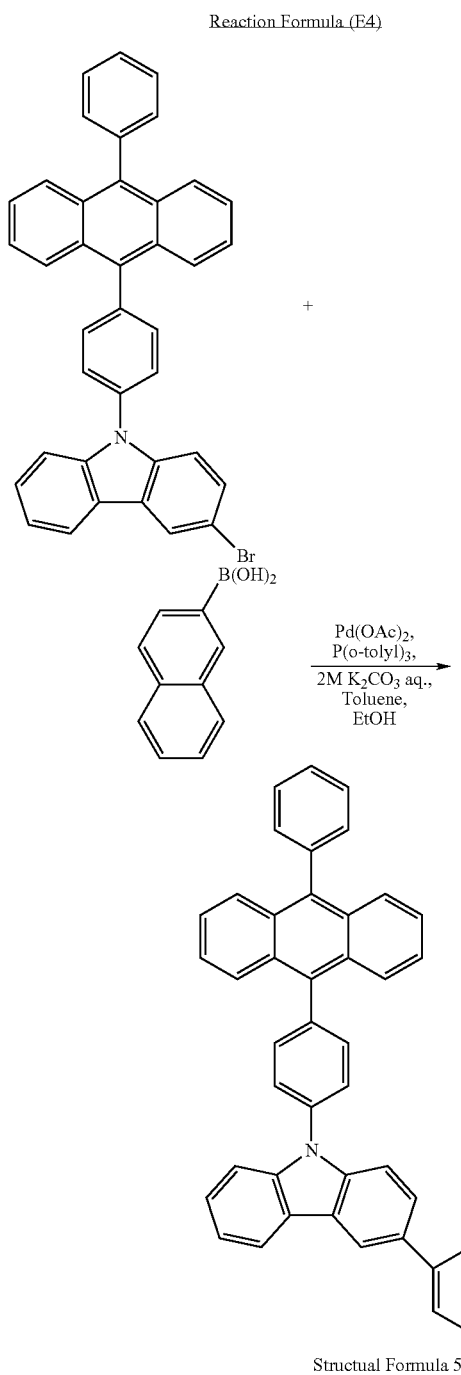

Structural Formula 5

In a 100 mL three neck flask were put 1.0 g (1.7 mmol) of 3-bromo-9-[4-(10-phenyl-9-anthryl)phenyl]-9H-carbazole, 0.30 g (1.7 mmol) of 2-naphthylboronic acid, and 0.13 g (0.42 mmol) of tri(ortho-tolyl)phosphine. The atmosphere in the flask was replaced with nitrogen. To this mixture were added 30 mL of toluene, 10 mL of ethanol, and 2.0 mL of an aqueous potassium carbonate solution (2.0 mol/L). This mixture was stirred to be degassed while the pressure was reduced. To this mixture was added 19 mg (0.085 mmol) of palladium(II) acetate. The resulting mixture was stirred under a nitrogen stream at 80° C. for 3 hours.

After being stirred, the mixture was separated into an aqueous layer and an organic layer. The aqueous layer was extracted with toluene. The extract and the organic layer were combined and washed with saturated brine. The organic layer was dried with magnesium sulfate, followed by gravity filtration of this mixture. An oily substance obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). An oily substance obtained by concentration of the resulting filtrate was purified by silica gel column chromatography (the developing solvent was a mixed solvent of a 5:1 ratio of hexane to toluene) to give a light yellow oily substance. This light yellow solid obtained was recrystallized with a mixed solvent of toluene and hexane to give the desired substance as 0.73 g of a light yellow powder in a yield of 69%.

Sublimation purification of 0.71 g of the light yellow powder obtained was performed by a train sublimation method. The light yellow powder was heated at 310° C. with an argon flow rate of 4.0 mL/min under reduced pressure. After the sublimation purification, 0.64 g of a light yellow solid which was the desired substance was obtained in a yield of 90%. By a nuclear magnetic resonance (NNW) method, this compound was confirmed to be 3-(2-naphthyl)-9-[4-(10-phenyl-9-anthryl)phenyl]-9H-carbazole CzPAβN) which was the desired compound.

The following are data of the $^1$H NMR measurement of the compound obtained: $^1$H NMR (CDCl$_3$, 300 MHz):δ=7.37-7.66 (m, 13H), 7.70-7.80 (m, 6H), 7.85-8.00 (m, 9H), 8.20 (s, 1H), 8.30 (d, J=4.8 Hz, 1H), 8.54 (s, 1H)

Figure 20A:
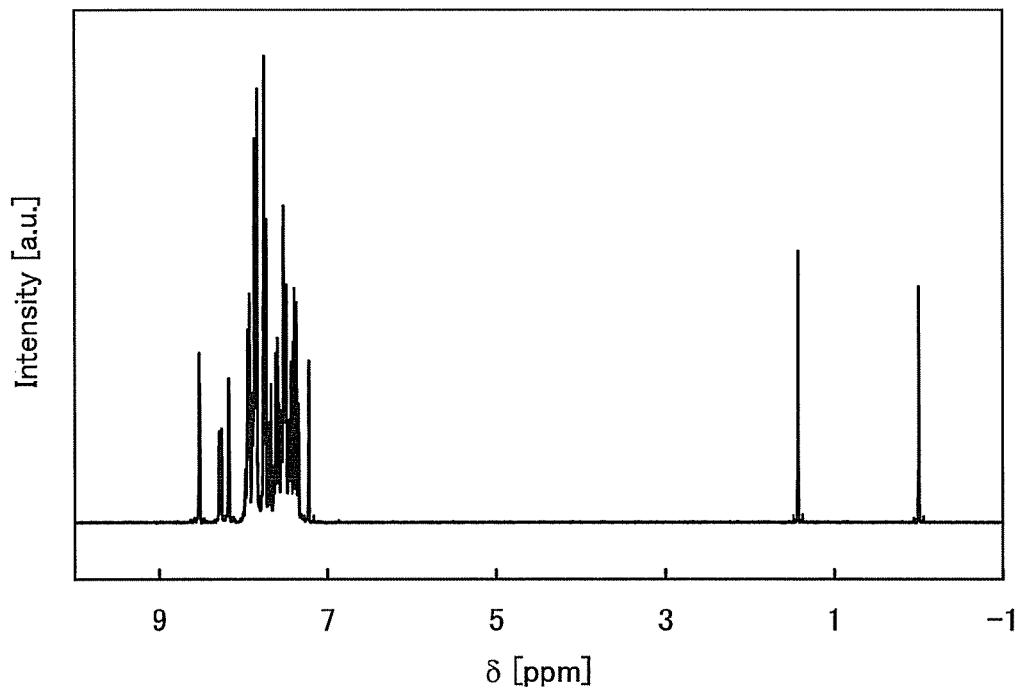
FIGS. 20A and 20B show ¹H NMR charts of CzPAβN.
Figure 20B:
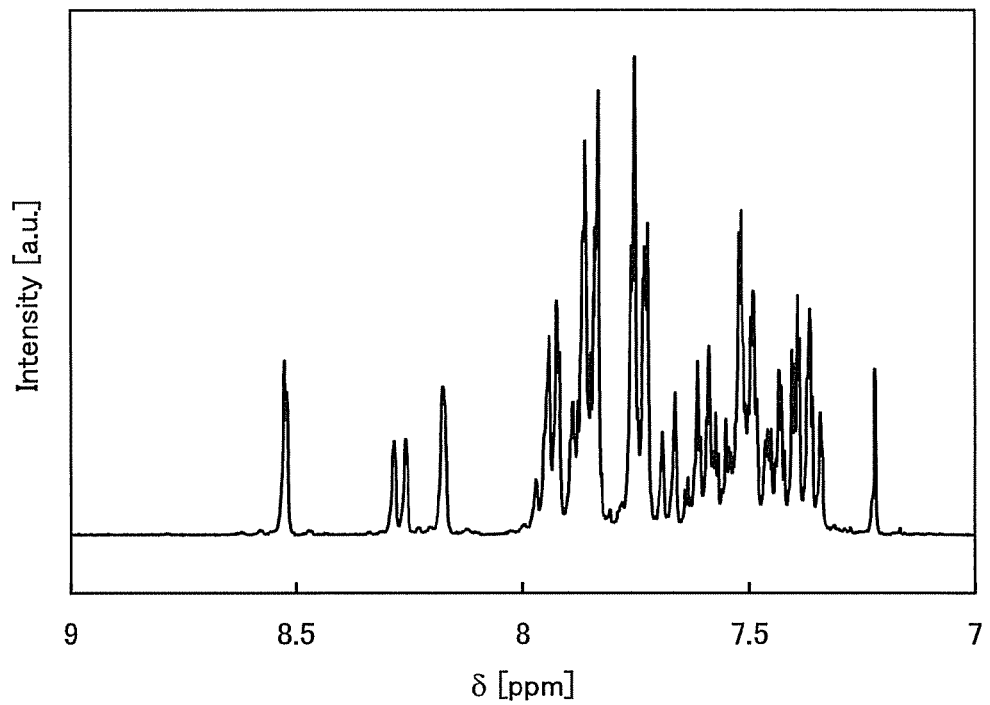

In addition, FIGS. 20A and 20B show $^1$H NMR charts. Note that FIG. 20B is a chart showing an enlarged part in the range of 7.0 ppm to 9.0 ppm in FIG. 20A.

EXAMPLE 5

[Example of Production of CzPApB]

In Example 5, an example in which 3-(biphenyl-4-yl)-9-[4-(10-phenyl-9-anthryl)phenyl]-9H-carbazole (abbreviation: CzPApB) represented by the above Structural Formula 6 is produced will be described. The example is illustrated in Reaction Formula (E5) and will be detailed hereinbelow.

Reaction Formula (E5)

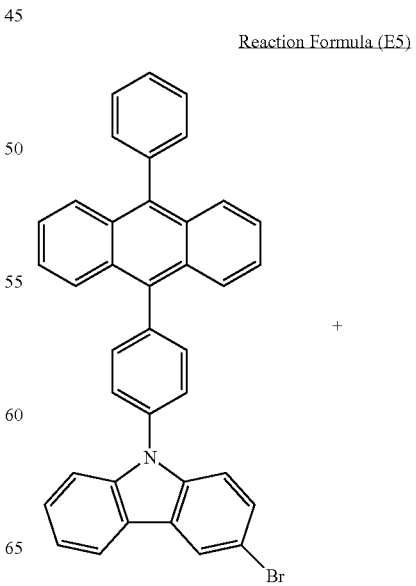

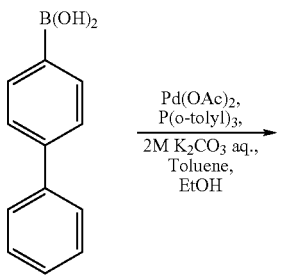

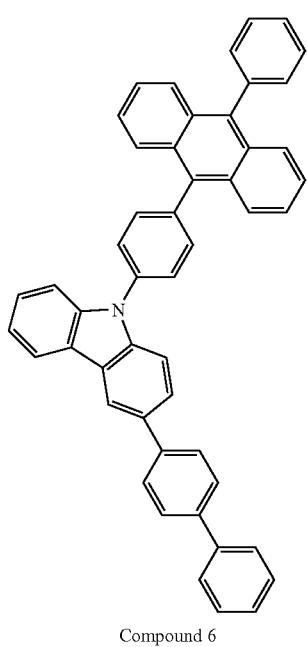

Compound 6

In a 300 mL three neck flask were put 3.0 g (5.2 mmol) of 3-bromo-9-[4-(10-phenyl-9-anthryl)phenyl]-9H-carbazole, 1.0 g (5.2 mmol) 4-biphenylboronic acid, and 0.40 g (1.3 mmol) of tri(ortho-tolyl)phosphine. The atmosphere in the flask was replaced with nitrogen. To this mixture were added 60 mL of toluene, 20 mL of ethanol, and 5.0 mL of an aqueous potassium carbonate solution (2.0 mol/L). This mixture was stirred to be degassed while the pressure was reduced. To this mixture was added 58 mg (0.26 mmol) of palladium(II) acetate. This mixture was stirred under a nitrogen stream at 80° C. for 3 hours, whereby a light black solid was precipitated.

This mixture was cooled to room temperature. Then, the solid precipitated was collected by suction filtration. The solid collected was dissolved in about 100 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). The resulting filtrate was concentrated to give a light yellow powder. The solid obtained was recrystallized with toluene to give the desired substance as 2.0 g of a light yellow powdered solid in a yield of 59%.

Sublimation purification of 1.8 g of the light yellow powder obtained was performed by a train sublimation method. The light yellow powder was heated at 320° C. with an argon flow rate of 4.0 mL/min under reduced pressure. After the sublimation purification, 1.5 g of a light yellow solid which was the desired substance was obtained in a yield of 84%. By a nuclear magnetic resonance (NMR) method, this compound was confirmed to be 3-(biphenyl-4-yl)-9-[4-(10-phenyl-9-anthryl)phenyl]-9H-carbazole (abbreviation: CzPApB) which was the desired compound.

The following are data of the $^1$H NMR measurement of the compound obtained: $^1$H NMR (CDCl$_3$, 300 MHz): δ=7.35-7.80 (m, 25H), 7.82-7.88 (m, 6H), 8.27 (d, J=7.8 Hz, 1H), 8.47 (d, J=1.5 Hz, 1H)

Figure 21A:
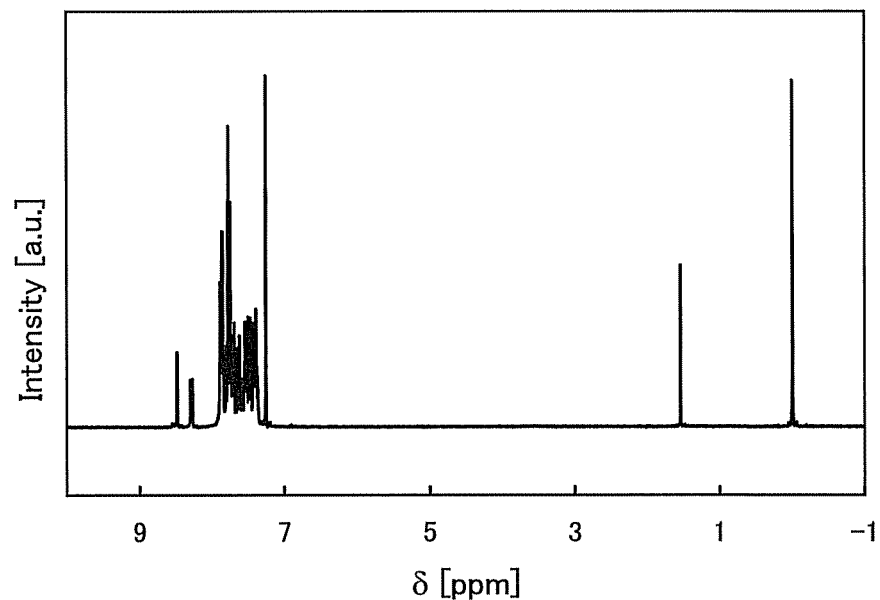
FIGS. 21A and 21B show ¹H NMR charts of CzPAρB.
Figure 21B:
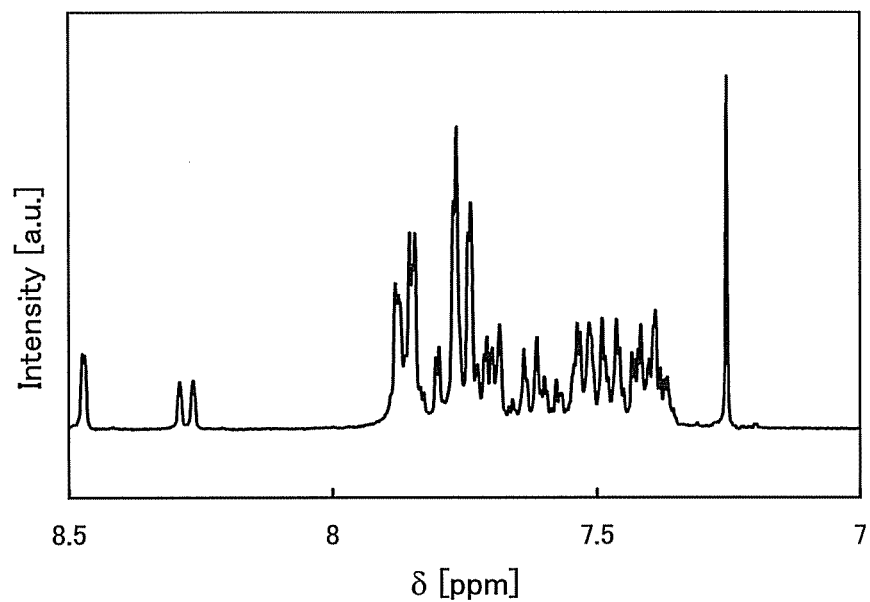

In addition, FIGS. 21A and 21B show $^1$NMR charts. Note that FIG. 21B is a chart showing an enlarged part in the range of 7.0 ppm to 8.5 ppm in FIG. 21A.

EXAMPLE 6

[Example of Production of CzPAoB]

In Example 6, an example in which 3-(biphenyl-2-yl)-9-[4-(10-phenyl-9-anthryl)phenyl]-9H-carbazole (abbreviation: CzPAoB) represented by Structural Formula 8 below is produced will be described. The example is illustrated in Reaction Formula (E6) and will be detailed hereinbelow.

Reaction Formula (E6)

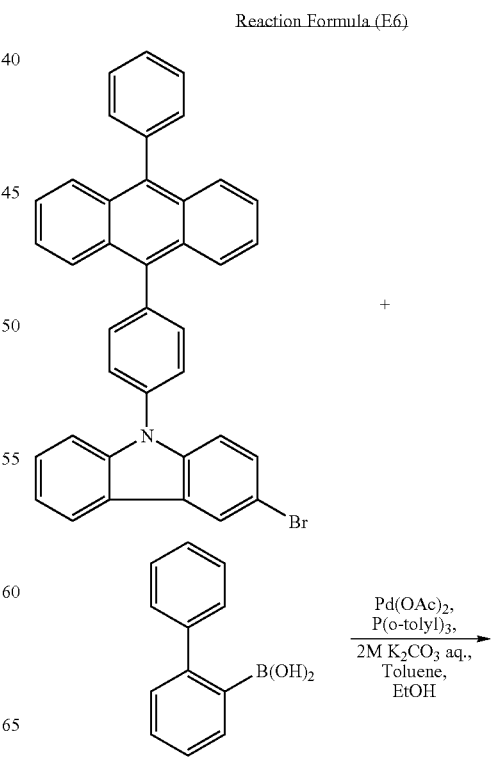

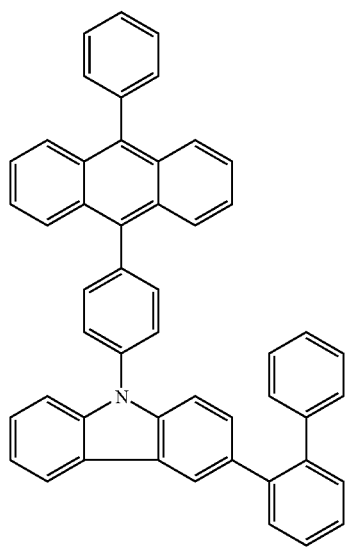

Structual Formula 8

In a 300 mL three neck flask were put 3.0 g (5.2 mmol) of 3-bromo-9-[4-(10-phenyl-9-anthryl)phenyl]-9H-carbazole, 1.0 g (5.2 mmol) of 2-biphenylboronic acid, and 0.40 g (1.3 mmol) of tri(ortho-tolyl)phosphine. The atmosphere in the flask was replaced with nitrogen. To this mixture were added 60 mL of toluene, 20 mL of ethanol, and 5.0 mL of an aqueous potassium carbonate solution (2.0 mol/L). This mixture was stirred to be degassed while the pressure was reduced. To this mixture was added. 58 mg (0.26 mmol) of palladium(II) acetate.

This mixture was stirred under a nitrogen stream at 80° C. for 3 hours. After being stirred, the mixture was separated into an aqueous layer and an organic layer. The aqueous layer was extracted with toluene. The extract and the organic layer were combined and washed with saturated brine. The organic layer was dried with magnesium sulfate, followed by gravity filtration of this mixture. An oily substance obtained by concentration of the resulting filtrate was dissolved in about 10 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). An oily substance obtained by concentration of the resulting filtrate was purified by silica gel column chromatography (the developing solvent was a mixed solvent of a 5:1 ratio of hexane to toluene) to give a light yellow oily substance. This light yellow solid obtained was recrystallized with a mixed solvent of toluene and hexane to give the desired substance as 2.0 g of a light yellow powder in a yield of 67%.

Sublimation purification of 2.0 g of the light yellow powder obtained was performed by a train sublimation method. The light yellow powder was heated at 280° C. with an argon flow rate of 4.0 mL/min under reduced pressure. After the sublimation purification, 1.9 g of a light yellow solid which was the desired substance was obtained in a yield of 93%. By a nuclear magnetic resonance (NMR) method, this compound was confirmed to be 3-(biphenyl-2-yl)-9-[4-(10-phenyl-9-anthryl)phenyl]-9H-carbazole (abbreviation: CzPAoB) which was the desired compound.

The following are data of the $^1$H NMR measurement of the compound obtained: $^1$H NMR (DMSO-d$_6$, 300 MHz): δ=7.14-7.27 (m, 6H), 7.33 (t, J=7.5 Hz, 1H), 7.45-7.81 (m, 22H), 7.87 (d, J=8.1 Hz, 2H), 8.21 (d, J=9.0 Hz, 2H)

Figure 22A:
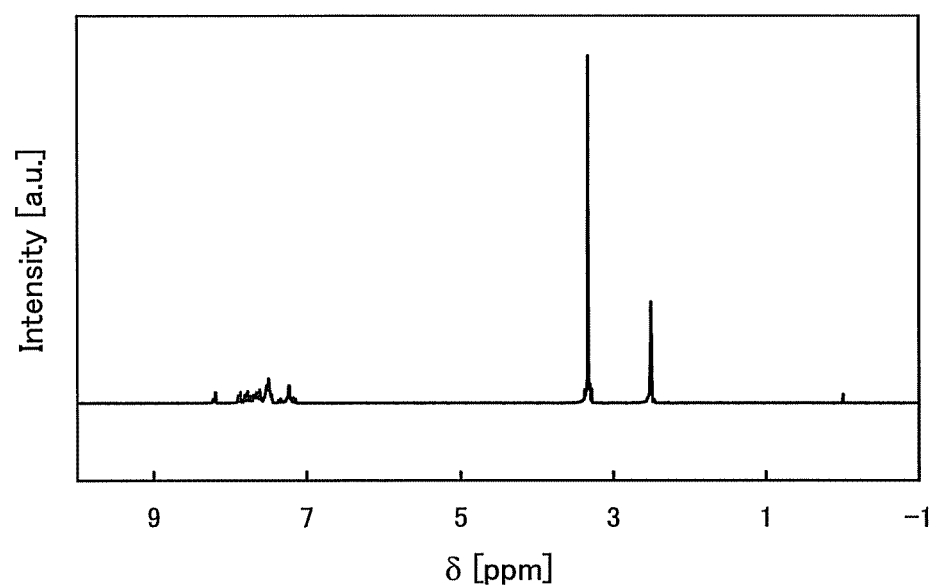
FIGS. 22A and 22B show ¹H NMR charts of CzPAoB.
Figure 22B:
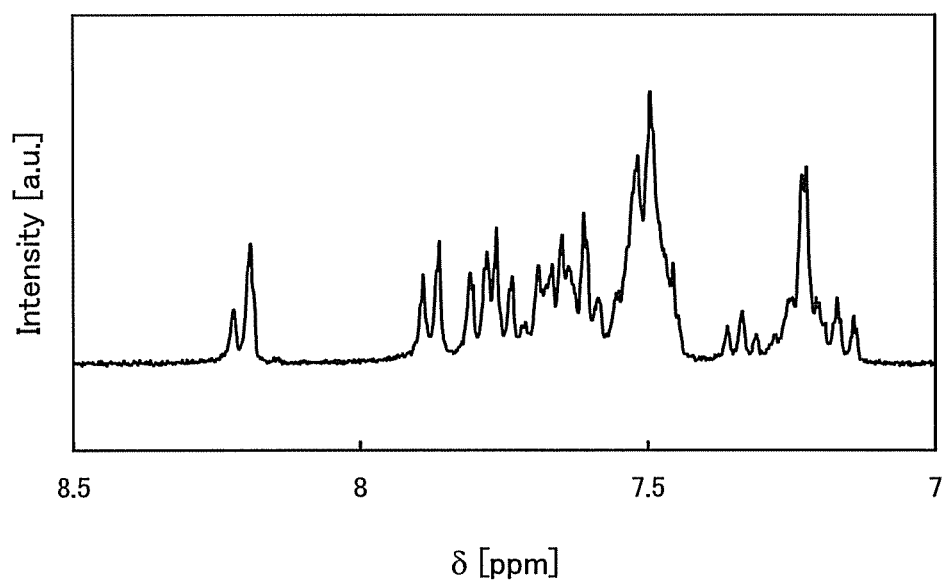

In addition, FIGS. 22A and 22B show $^1$H NMR charts. Note that FIG. 22B is a chart showing an enlarged part in the range of 7.0 ppm to 8.5 ppm in FIG. 22A.

EXAMPLE 7

[Example of Production of CzPAFL]

In Example 7, an example in which 3-(9,9-dimethylfluoren-2-yl)-9-[4-(10-phenyl-9-anthryl)phenyl]-9H-carbazole (abbreviation: CzPAFL) represented by the above Structural Formula 15 is produced will be described. The example is illustrated in Reaction Formula (E7) and will be detailed hereinbelow.

Reaction Formula (E7)

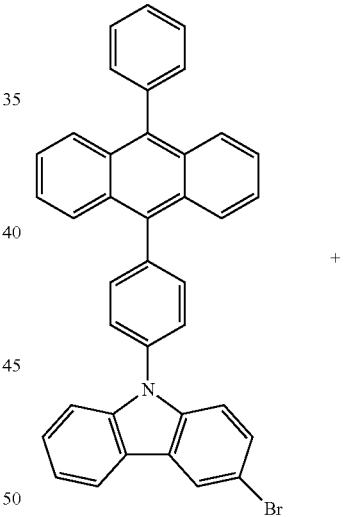

+

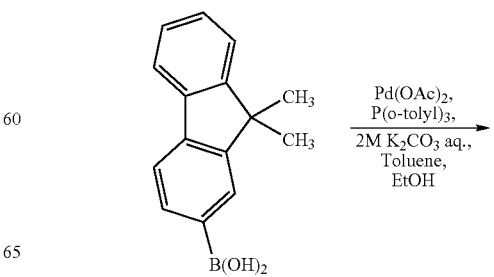

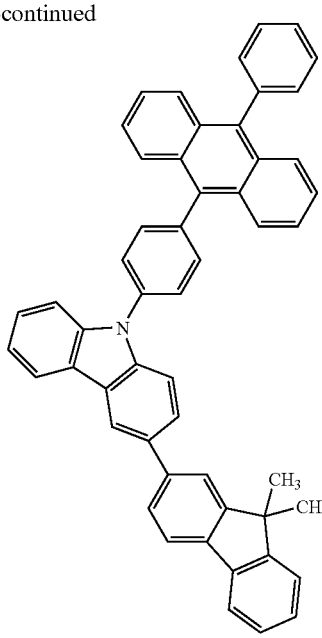

Structual Formula 15

In a 100 mL three neck flask were put 0.80 g (1.4 mmol) of 3-bromo-9-[4-(10-phenyl-9-anthryl)phenyl]-9H-carbazole, 0.33 g (1.4 mmol) of 9,9-dimethylfluorene-2-boronic acid, and 0.11 g (0.35 mmol) of tri(ortho-tolyl)phosphine. The atmosphere in the flask was replaced with nitrogen. To this mixture were added 2.0 mL of an aqueous potassium carbonate solution (2.0 mol/L), 30 mL of toluene, and 10 mL of ethanol. This mixture was stirred to be degassed while the pressure was reduced.

To this mixture was added 16 mg (0.070 mmol) of palladium(II) acetate. This mixture was stirred under a nitrogen stream at 80° C. for 4 hours, whereby a light black solid was precipitated. This mixture was cooled to room temperature. Then, the solid precipitated was collected by suction filtration. The solid collected was dissolved in about 50 mL of toluene. The mixture was added to the filtrate resulting from the above suction filtration. This mixture was separated into an aqueous layer and an organic layer. The aqueous layer was extracted with toluene. The extract and the organic layer were combined and washed with saturated brine. The organic layer was dried with magnesium sulfate, followed by gravity filtration of this mixture.

A solid obtained by concentration of the resulting filtrate was dissolved in about 50 mL of toluene. This solution was suction filtered through Celite (manufactured by Wako Pure Chemical Industries, Ltd., Catalog No. 531-16855), alumina, and Florisil (manufactured by Wako Pure Chemical Industries, Ltd., Catalog No. 540-00135). A solid obtained by concentration of the resulting filtrate was purified by silica gel column chromatography (the developing solvent was a mixed solvent of a 5:1 ratio of hexane to toluene) to give a light yellow solid. This solid was recrystallized with a mixed solvent of toluene and hexane to give the desired substance as 0.57 g of a light yellow powder in a yield of 54%.

Sublimation purification of 0.54 g of the light yellow powder obtained was performed by a train sublimation method. The light yellow powder was heated at 330° C. with an argon flow rate of 4.0 mL/min under reduced pressure. After the sublimation purification, 0.50 g of a light yellow solid which was the desired substance was obtained in a yield of 93%. By a nuclear magnetic resonance (NMR) method, this compound was confirmed to be 3-(9,9-dimethylfluoren-2-yl)-9-[4-(10-phenyl-9-anthryl)phenyl]-9H-carbazole (abbreviation: CzPAFL) which was the desired compound.

The following are data of the $^1$H NMR measurement of the compound obtained: $^1$H NMR (CDCl$_3$, 300 MHz):δ=1.61 (s, 6H), 7.34-7.54 (in, 11H), 7.57-7.66 (m, 3H), 7.70-7.81 (m, 10H), 7.84-7.89 (m, 5H), 8.30 (d, J=7.5 Hz, 1H), 8.47 (s, 1H)

Figure 23A:
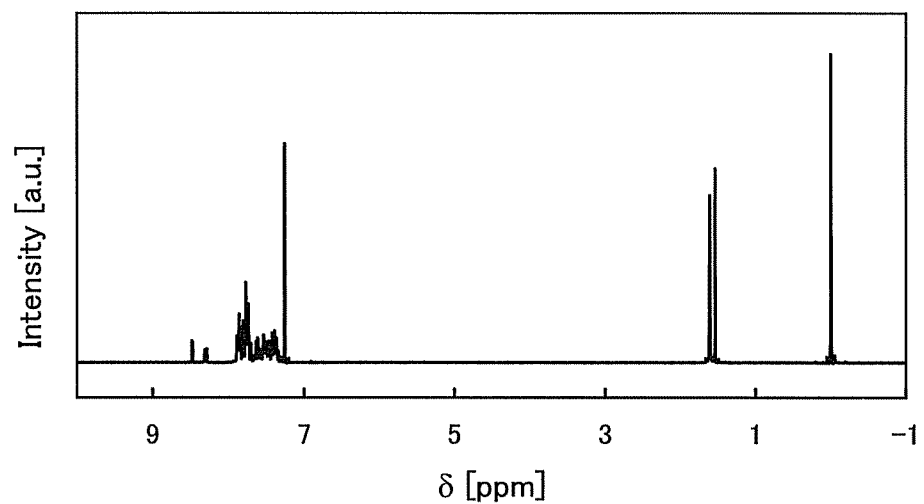
FIGS. 23A and 23B show ¹H NMR charts of CzPAFL.
Figure 23B:
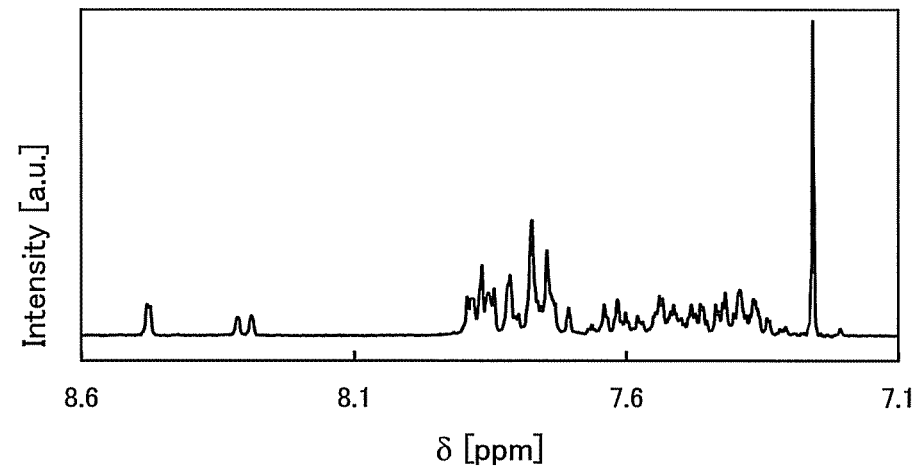

In addition, FIGS. 23A and 23B show $^1$H NMR charts. Note that FIG. 23B is a chart showing an enlarged part in the range of 7.1 ppm to 8.6 ppm in FIG. 23A.

[Example of Production of Light-Emitting Elements]

Figure 24:
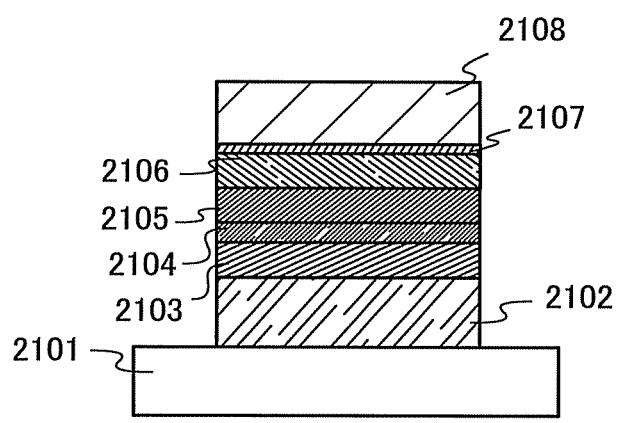
FIG. 24 illustrates an example of formation of light-emitting elements according to an embodiment of the present invention.

In this example of the production, an example in which light-emitting elements are formed using carbazole derivatives produced by a production method of Embodiment 1 will be described with reference to FIG. 24. In addition, Table 1 shows an element structure of each of Light-Emitting Elements 1 and 2, in which all the mixture ratios are weight ratios.

TABLE 1

|  | Light-Emitting Element 1 | Light-Emitting Element 2 |
|---|---|---|
| First Electrode 2102 | ITSO 110 nm | ITSO 110 nm |
| First Layer 2103 | NPB:MoOx (=4:1) 50 nm | NPB:MoOx (=4:1) 50 nm |
| Second Layer 2104 | NPB 10 nm | NPB 10 nm |
| Third Layer 2105 | CzPAP:PCBAPA (=1:0.1) 30 nm | CzPAP:2PCAPA (=1:0.05) 30 nm |
| Fourth Layer 2106 | Alq 10 nm | Alq:DPQd (=1:0.005) 10 nm |
|  | Bphen 20 nm | Bphen 30 nm |
| Fifth Layer 2107 | LiF 1 nm | LiF 1 nm |
| Second Electrode 2108 | Al 200 nm | Al 200 nm |

Hereinafter, a method of forming Light-Emitting Elements 1 and 2 according to this example will be described in turn. First, an example of formation of Light-Emitting Element 1 will be described. For Light-Emitting Element 1, indium tin oxide containing silicon oxide (ITSO) was deposited on a glass substrate 2101 by a sputtering method, whereby a first electrode 2102 was formed. Note that the thickness of the first electrode was 110 nm and the area of the electrode was set to 2 mm×2 mm.

Next, the glass substrate provided with the first electrode was fixed to a substrate holder provided in a vacuum evaporation apparatus such that the surface on which the first electrode was formed faced downward. After the pressure was reduced to approximately $10^{-4}$ Pa, 4,4'-bis[N-(1-naphthyl)-N-phenylamino]biphenyl (abbreviation: NPB) and molybdenum(VI) oxide were co-evaporated on the first electrode 2102, whereby a layer including a composite material of an organic compound and an inorganic compound was formed as a first layer 2103. The thickness of the first layer was set to 50 nm, and the weight ratio of NPB to molybdenum(VI)

oxide was adjusted to be 4:1 (=NPB:molybdenum oxide). Note that the co-evaporation method refers to an evaporation method by which evaporation of a plurality of materials is conducted from a plurality of evaporation sources at the same time in one treatment chamber. Successively, NPB was evaporated to form a 10-nm-thick film as a second layer 2104 as a hole-transport layer.

Next, on the second layer 2104, CzPAP produced in Example 1 and 4-(10-phenyl-9-anthryl)-4'-(9-phenyl-9H-carbazol-3-yl)triphenylamine (abbreviation: PCBAPA) were co-evaporated with the weight ratio of CzPAP to PCBAPA being 1:0.1, whereby a third layer 2105 was formed as a light-emitting layer. The thickness of the light-emitting layer was set to 30 nm.

Next, on the third layer 2105, a 10-nm-thick film of Alq and a 20-nm-thick film of Bphen were formed by evaporation and stacked, whereby a fourth layer 2106 was formed as an electron-transport layer. Further, lithium fluoride (LiF) was evaporated on the fourth layer 2106 to a thickness of 1 nm, whereby a fifth layer 2107 was formed as an electron-inject layer. Lastly, a 200-nm-thick film of aluminum was formed as a second electrode 2108 which serves as a cathode. Thus, Light-Emitting Element 1 of this example was completed.

Next, an example of formation of Light-Emitting Element 2 will be described. Light-Emitting Element 2 was formed in a manner similar to that of Light-Emitting Element 1 except the third layer 2105 and the fourth layer 2106. For Light-Emitting Element 2, on the second layer 2104, CzPAP produced in Example 1 and 9,10-diphenyl-2-[4N-phenyl-N-(9-phenyl-9H-carbazol-3-yl)amino]anthracene (abbreviation: 2PCAPA) were co-evaporated with the weight ratio of CzPAP to 2PCAPA being 1:0.05, whereby the third layer 2105 was formed as a light-emitting layer. The thickness of the third layer was set to 30 nm.

Next, on the third layer 2105, a 10-nm-thick film formed by co-evaporation of Alq and N,N'-diphenylquinacridone (abbreviation: DPQd) with the weight ratio of Alq to DPQd being 1:0.005 and a 30-nm-thick film formed by evaporation of Bphen were stacked, whereby the fourth layer 2106 was formed as an electron-transport layer. Thus, Light-Emitting Element 2 of this example was completed. Note that in all of the above evaporation steps, a resistance heating method was adopted. In addition, Structural Formulae of NPB, PCBAPA, 2PCAPA, DPQd, Alq, and Bphen are illustrated below.

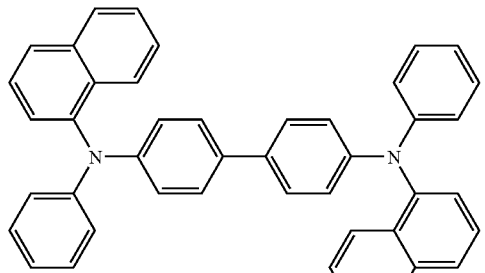

NPB

-continued

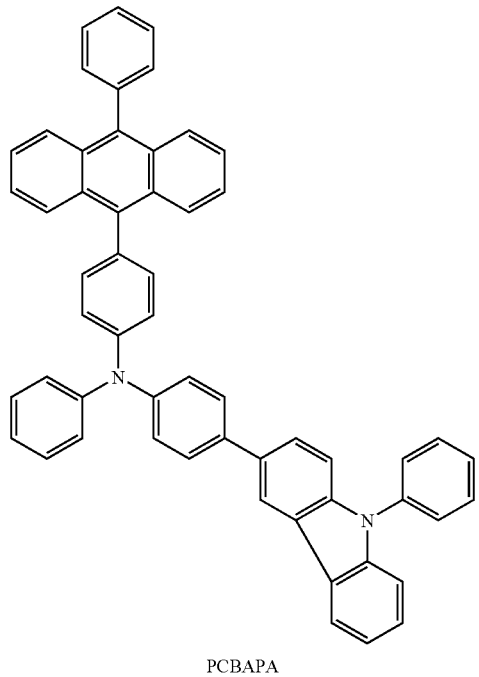

PCBAPA

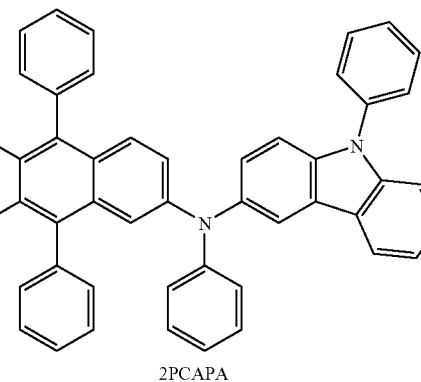

2PCAPA

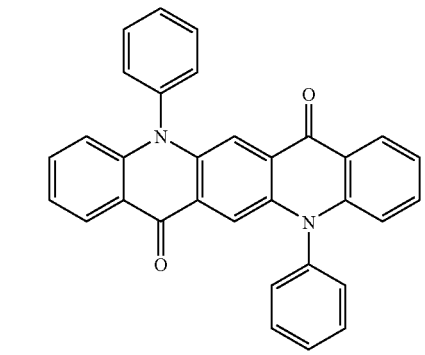

DPQd

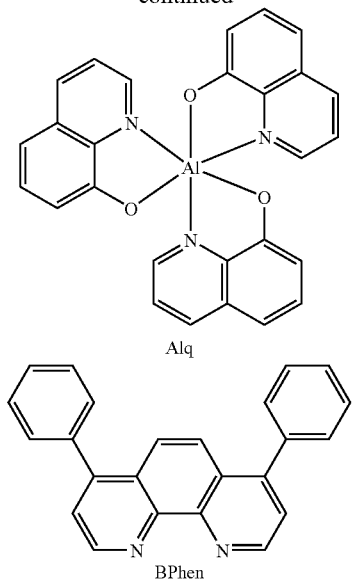

Alq

BPhen

The thus obtained Light-Emitting Elements 1 and 2 were sealed in a glove box containing a nitrogen atmosphere so as not to be exposed to air. Then, operation characteristics of Light-Emitting Elements 1 and 2 were measured. Note that the measurement was carried out at room temperature (in the atmosphere kept at 25° C.).

Figure 25:
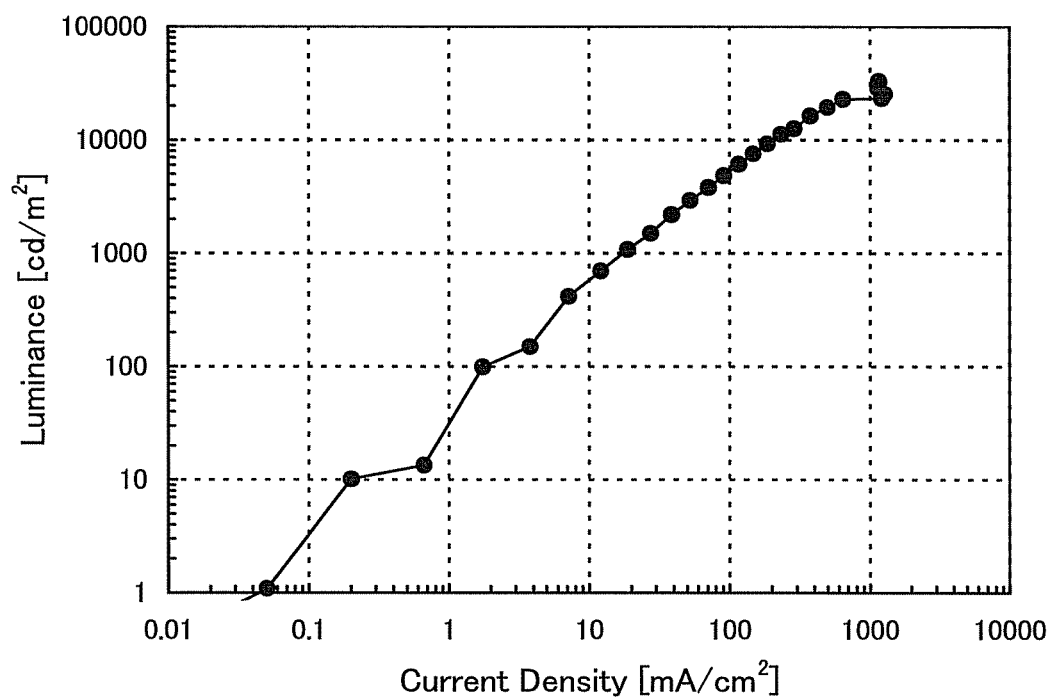
FIG. 25 shows current density vs. luminance characteristics of Light-Emitting Element 1.
Figure 26:
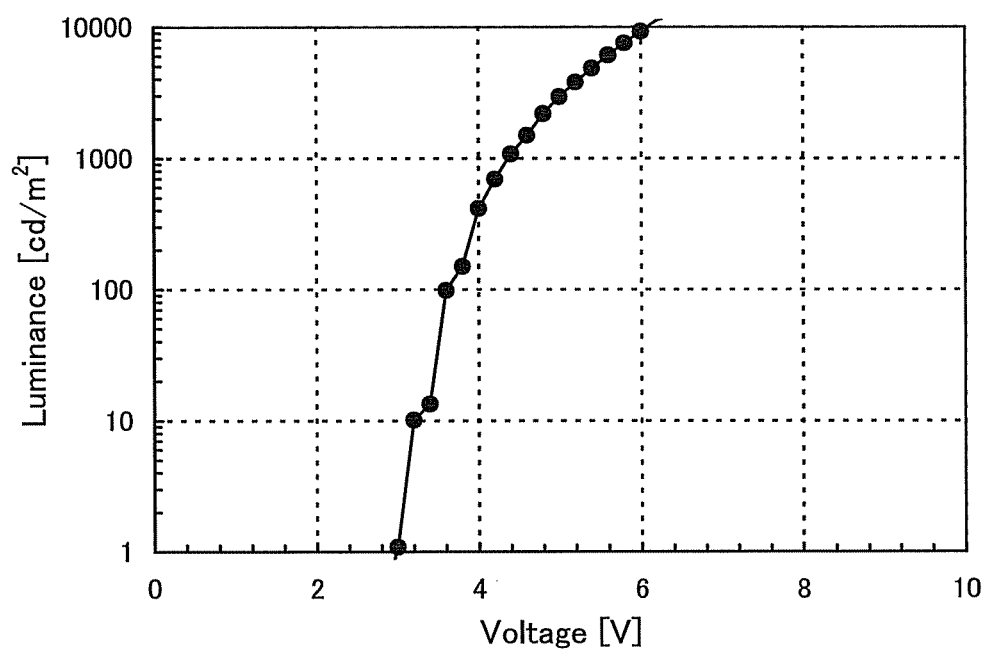
FIG. 26 shows voltage vs. luminance characteristics of Light-Emitting Element 1.
Figure 27:
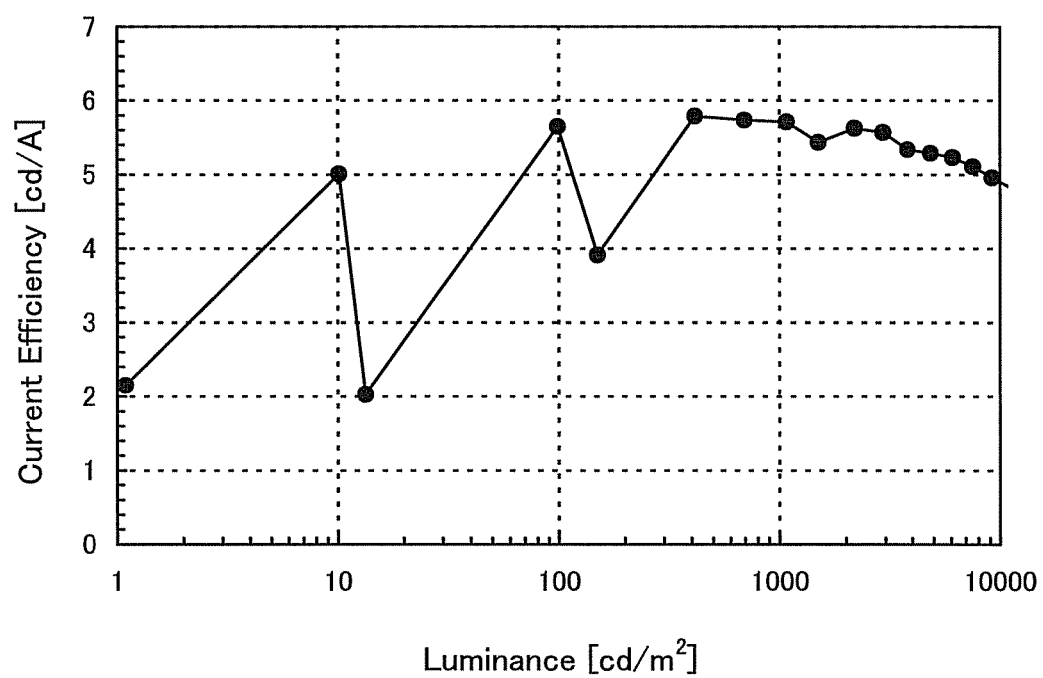
FIG. 27 shows luminance vs. current efficiency characteristics of Light-Emitting Element 1.
Figure 28:
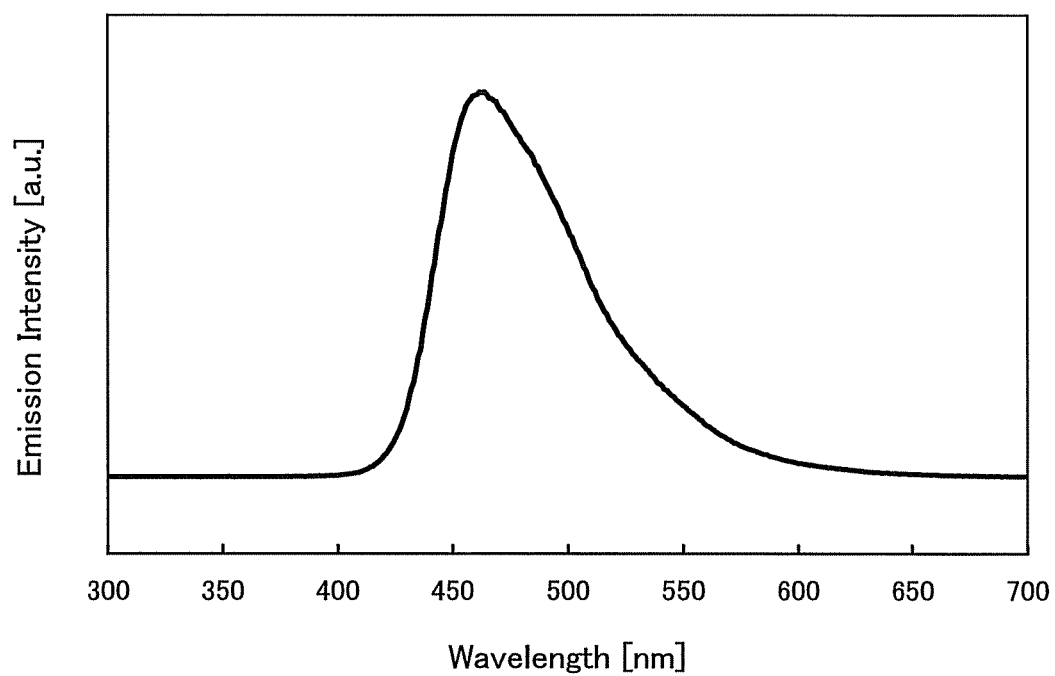
FIG. 28 shows an emission spectrum of Light-Emitting Element 1.

FIG. 25 shows current density vs. luminance characteristics of Light-Emitting Element 1. In FIG. 25, the horizontal axis represents current density (mA/cm$^2$) and the vertical axis represents luminance (cd/m$^2$). FIG. 26 shows voltage vs. luminance characteristics of Light-Emitting Element 1. In FIG. 26, the horizontal axis represents applied voltage (V) and the vertical axis represents luminance (cd/m$^2$). FIG. 27 shows luminance vs. current efficiency characteristics of Light-Emitting Element 1. In FIG. 27, the horizontal axis represents luminance (cd/m$^2$) and the vertical axis represents current efficiency (cd/A). FIG. 28 shows an emission spectrum of Light-Emitting Element 1 at a current of 1 mA. FIG. 28 indicates that Light-Emitting Element 1 exhibits light emission from PCBAPA which is a blue light-emitting material.

Light-Emitting Element 1 exhibited excellent blue light emission where the CIE chromaticity coordinates were (x=0.16, y=0.20) when the luminance was 1080 cd/m$^2$. In addition, the current efficiency and external quantum efficiency at a luminance of 1080 cd/m$^2$ were 5.7 cd/A and 3.9% respectively. Further, the voltage, current density, and power efficiency at a luminance of 1080 cd/m$^2$ were 4.4 V, 18.9 mA/cm$^2$, and 4.1 lm/W, respectively.

Figure 29:
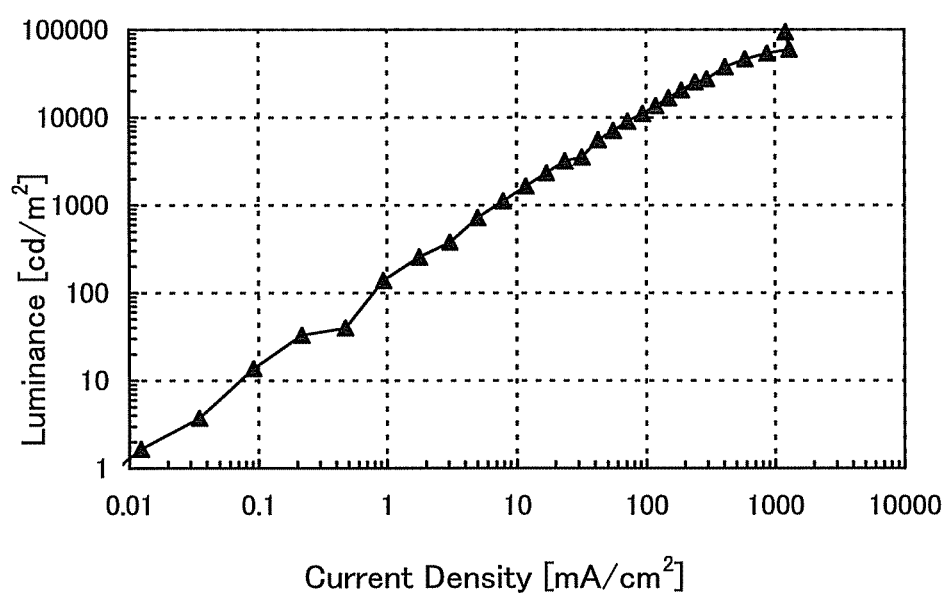
FIG. 29 shows current density vs. luminance characteristics of Light-Emitting Element 2.
Figure 30:
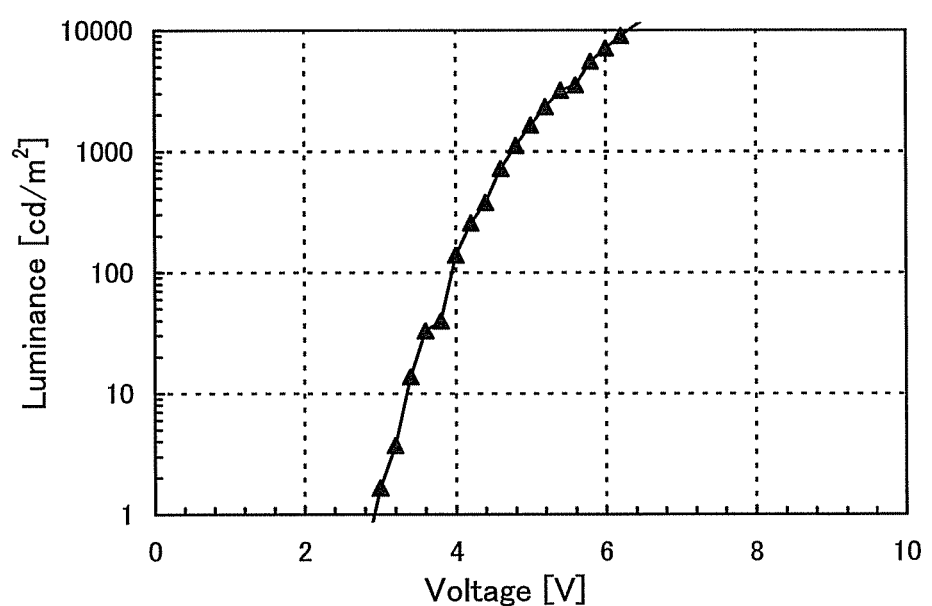
FIG. 30 shows voltage vs. luminance characteristics of Light-Emitting Element 2.
Figure 31:
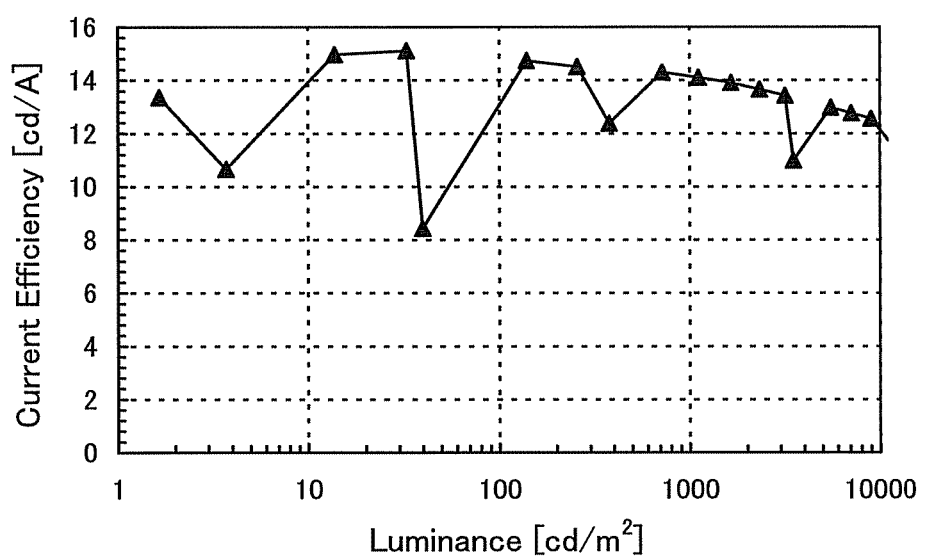
FIG. 31 shows luminance vs. current efficiency characteristics of Light-Emitting Element 2.
Figure 32:
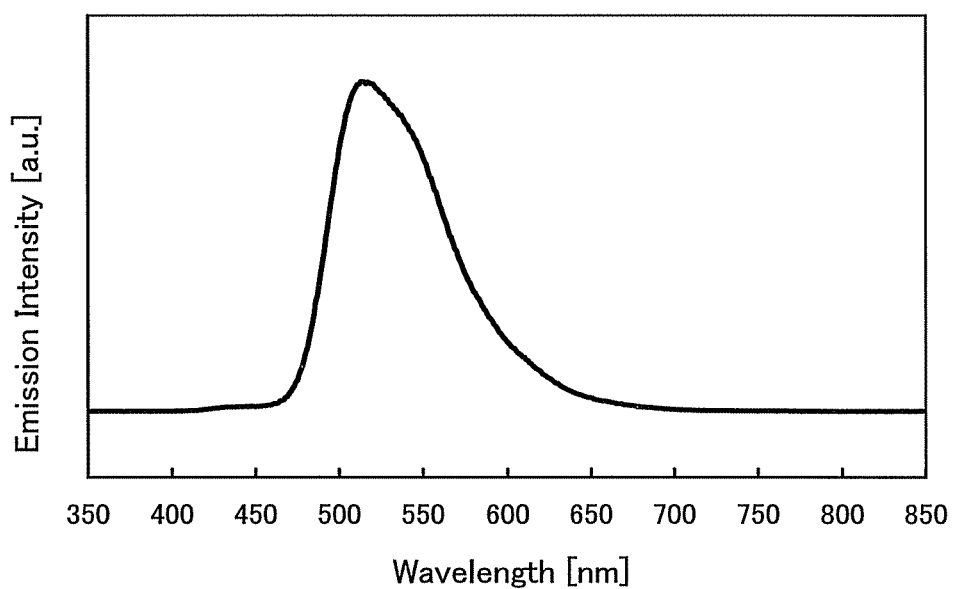
FIG. 32 shows an emission spectrum of Light-Emitting Element 2.

FIG. 29 shows current density vs. luminance characteristics of Light-Emitting Element 2. In FIG. 29 the horizontal axis represents current density (mA/cm$^2$) and the vertical axis represents luminance (cd/m$^2$). FIG. 30 shows voltage vs. luminance characteristics of Light-Emitting Element 2. In FIG. 30, the horizontal axis represents applied voltage (V) and the vertical axis represents luminance (cd/m$^2$). FIG. 31 shows luminance vs. current efficiency characteristics of Light-Emitting Element 2. In FIG. 31, the horizontal axis represents luminance (cd/m$^2$) and the vertical axis represents current efficiency (cd/A). FIG. 32 shows an emission spectrum of Light-Emitting Element 2 at a current of 1 mA. FIG. 32 indicates that Light-Emitting Element 2 exhibits light emission from 2PCAPA which is a green light-emitting material.

Light-Emitting Element 2 exhibited excellent green light emission where the CIE chromaticity coordinates were (x=0.29, y=0.61) when the luminance was 5520 cd/m$^2$. In addition, the current efficiency at a luminance of 5520 cd/m$^2$ were 13 cd/A. Further, the voltage, current density, and power efficiency at a luminance of 5520 cd/m$^2$ were 5.8 V, 42.6 mA/cm$^2$, and 7.0 lm/W, respectively.

Further, reliability testing of Light-Emitting Elements 1 and 2 which were formed was carried out as follows. For Light-Emitting Element 1, the luminance was measured after every certain period of time passes, while the same amount of current as that flowing through Light-Emitting Element 1 when light emission with a luminance of 1000 cd/m$^2$ was obtained in the initial state was continuously made flow. Also for Light-Emitting Element 2, the luminance was measured after every certain period of time passes, while the same amount of current as that flowing through Light-Emitting Element 2 when light emission with a luminance of 5000 cd/m$^2$ was obtained in the initial state was continuously made flow.

Figure 33:
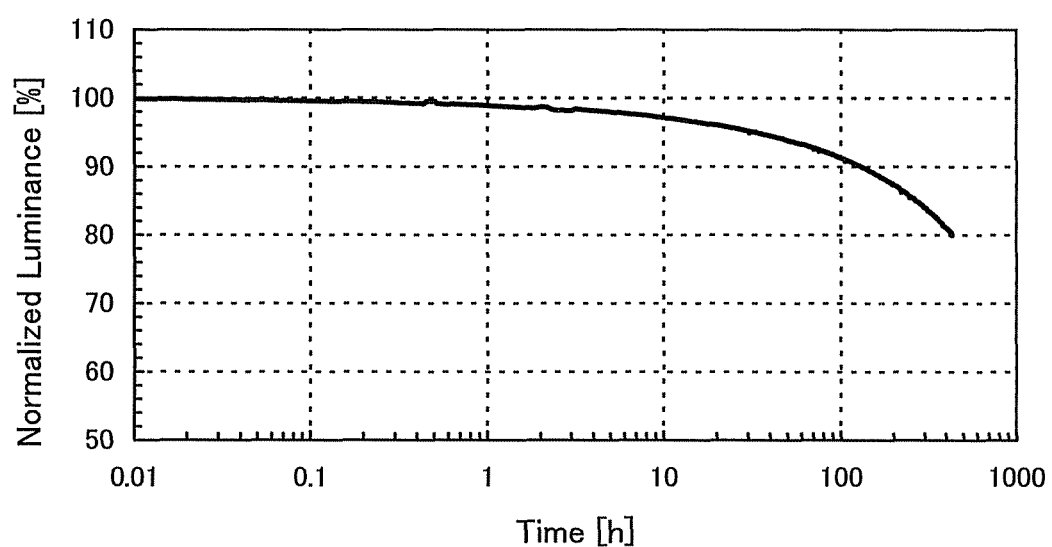
FIG. 33 shows results obtained by reliability testing of Light-Emitting Element 1.
Figure 34:
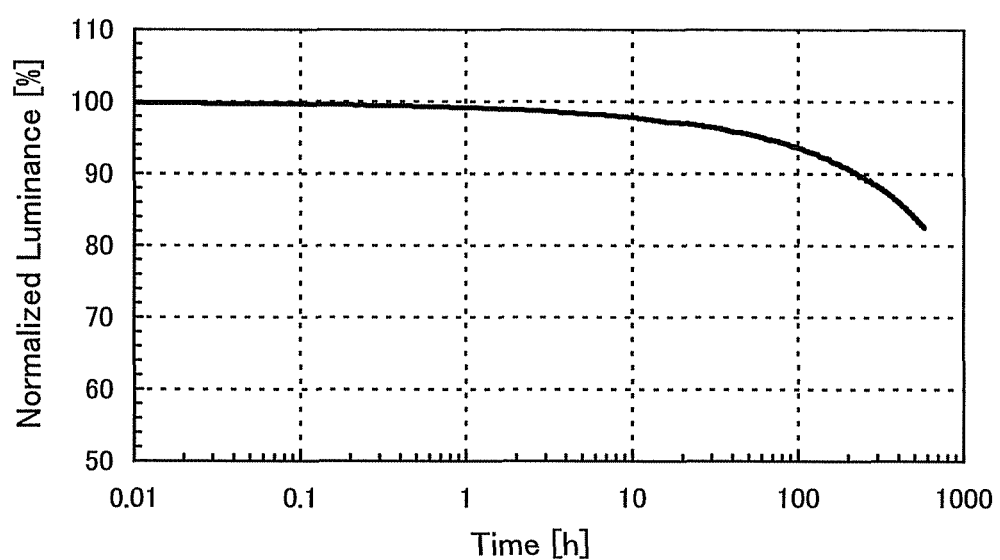
FIG. 34 shows results obtained by reliability testing of Light-Emitting Element 2.

FIG. 33 shows results obtained by the reliability testing of Light-Emitting Element 1, and FIG. 34 shows results obtained by the reliability testing of Light-Emitting Element 2. FIG. 33 and FIG. 34 each show a change in luminance over time. Note that in FIG. 33 and FIG. 34, the horizontal axis represents current flow time (hour) and the vertical axis represents the proportion of luminance with respect to the initial luminance at each time, that is, normalized luminance (%). As can be seen from FIG. 33, Light-Emitting Element 1 maintains 80% of the initial luminance even after 430 hours; thus, Light-Emitting Element 1 is found to have long lifetime in which luminance does not easily deteriorate over time. Further, as can be seen from FIG. 34, Light-Emitting Element 2 maintains 82% of the initial luminance even after 570 hours; thus, Light-Emitting Element 2 is found to have long lifetime in which luminance does not easily deteriorate over time.

As described above, Light-Emitting Elements 1 and 2 which were highly reliable were obtained. According to this example, it was confirmed that the light-emitting elements according to the embodiment of the present invention each have the characteristics as a light-emitting element and function sufficiently. Further, from the results of the reliability testing, it is understood that a highly reliable light-emitting element in which a short circuit due to defects of the film or the like is not caused even if the element is continuously made to emit light can be obtained.

[Example of Production of Chemical Substances Used in the Example of Production of Light-Emitting Elements]

A substance used in Example of Production of Light-Emitting Element 1, 4-(10-phenyl-9-anthryl)-4'-(9-phenyl-9H-carbazol-3-yl)triphenylamine (abbreviation: PCBAPA), is a novel substance and has a structure below. Hereinafter, a method for producing this substance will be described as an example of production of the chemical substances used in Example of Production of Light-Emitting Elements. The production process includes three reaction steps, and each step will be specifically described below.

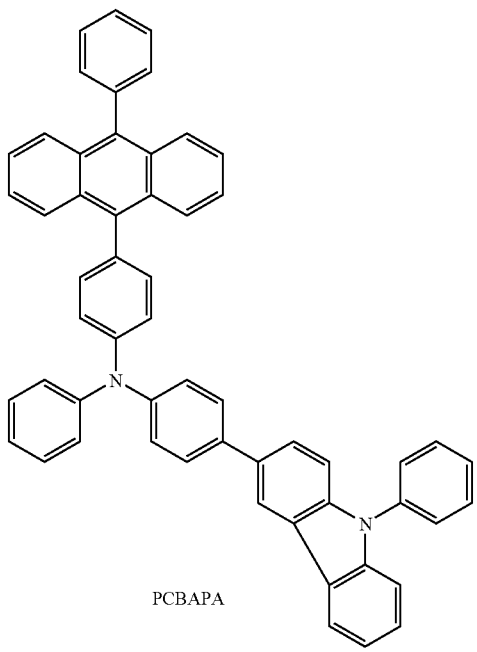 [SMILES: c1ccc(-c2c3ccccc3c(-c3ccc(N(c4ccccc4)c4ccc(-c5ccc6c(c5)c5ccccc5n6-c5ccccc5)cc4)cc3)c3ccccc23)cc1]

PCBAPA

[First Step]
First Step is a step of synthesizing 9-phenyl-9H-carbazole-3-boronic acid and illustrated in the following Reaction Formula (P1).

Reaction Formula (P1)

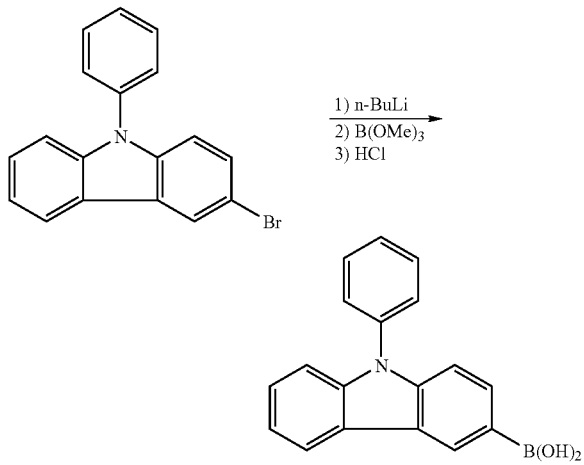

In this step, first, in a 500 mL three neck flask was put 10 g (31 mmol) of 3-bromo-9-phenyl-9H-carbazole. The atmosphere in the flask was replaced with nitrogen. In the flask was put 150 mL of tetrahydrofuran (THF), and 3-bromo-9-phenyl-9H-carbazole was dissolved therein. This solution was cooled to −80° C. To this solution was added 20 mL (32 mmol) of a solution of n-butyllithium (1.58 mol/L) in hexane by being dripped with a syringe. After that, the solution was stirred at the same temperature for 1 hour.

After the solution was stirred, 3.8 mL (34 mmol) of trimethyl borate was added to this solution. The solution was stirred for about 15 hours while the temperature of the solution was being returned to room temperature. Then, about 150 mL (1.0 mol/L) of dilute hydrochloric acid was added to this solution, followed by stirring for 1 hour. After being stirred, this mixture was separated into an aqueous layer and an organic layer. The aqueous layer was extracted with ethyl acetate. The extract and the organic layer were combined and washed with a saturated aqueous sodium hydrogen carbonate solution. The organic layer was dried with magnesium sulfate, and then this mixture was gravity filtered. The resulting filtrate was concentrated to give an oily light brown substance. This oily substance was dried under reduced pressure to give the desired substance as 7.5 g of a light brown solid in a yield of 86%.

[Second Step]
Second Step is a step of synthesizing 4-(9-phenyl-9H-carbazol-3-yl)diphenylamine (abbreviation: PCBA) and illustrated in the following Reaction Formula (P2).

Reaction Formula (P2)

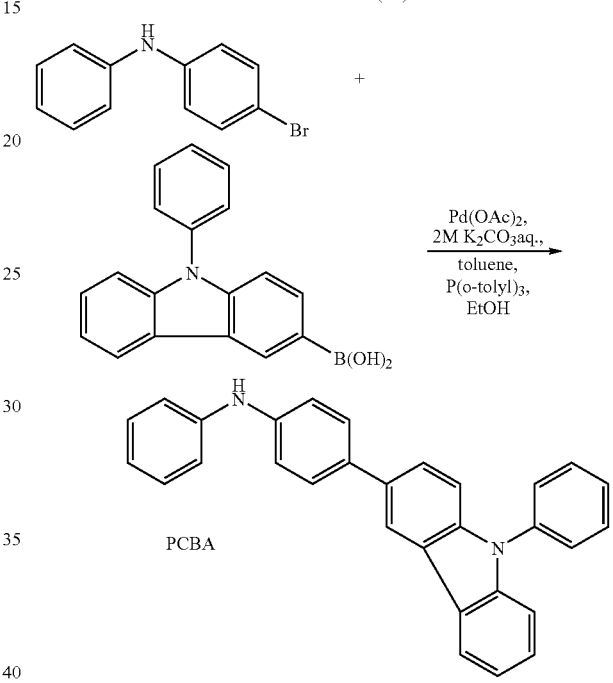

PCBA

In this step, first, in a 500 mL three neck flask were put 6.5 g (26 mmol) of 4-bromo-diphenylamine, 7.5 g (26 mmol) of 9-phenyl-9H-carbazole-3-boronic acid, and 400 mg (1.3 mmol) of tri(ortho-tolyl)phosphine. The atmosphere in the flask was replaced with nitrogen. To this mixture were added 100 mL of toluene, 50 mL of ethanol, and 14 mL of an aqueous potassium carbonate solution (2.0 mol/L). Under reduced pressure, this mixture was degassed while being stirred. After that, 67 mg (30 mmol) of palladium(II) acetate was added to the mixture.

This mixture was refluxed for 10 hours at 100° C. After that, this mixture was separated into an aqueous layer and an organic layer. The aqueous layer was extracted with toluene. The extract and the organic layer were combined and washed with saturated brine. The organic layer was dried with magnesium sulfate, followed by gravity filtration of this mixture. The resulting filtrate was concentrated to give an oily light brown substance. This oily substance was purified by silica gel column chromatography (the developing solvent was a mixed solvent of a 4:6 ratio of hexane to toluene). A white solid obtained after the purification was recrystallized with a mixed solvent of dichloromethane and hexane to give the desired substance as 4.9 g of a white solid in a yield of 45%. The solid obtained by the above Second Step was measured by a nuclear magnetic resonance (NMR) method.

The measurement data obtained by $^1$H NMR are described below. The measurement results indicate that PCBA, which was a source material of the synthesis of PCBAPA, was obtained. $^1$H NMR (DMSO-d$_6$, 300 MHz):δ=6.81-6.86 (m, 1H), 7.12(dd, J$_1$=0.9 Hz, J$_2$=8.7 Hz, 2H), 7.19 (d, J=8.7 Hz, 2H), 7.23-7.32 (m, 3H), 7.37-7.4 7(m, 3H), 7.51-7.57 (m, 1H), 7.61-7.73 (m, 7H) 8.28 (s, 1H), 8.33 (d, J=7.2 Hz, 1H), 8.50 (d, J=1.5 Hz, 1H)

[Third Step]

Third Step is a step of synthesizing PCBAPA and illustrated in the following Reaction Formula (P3).

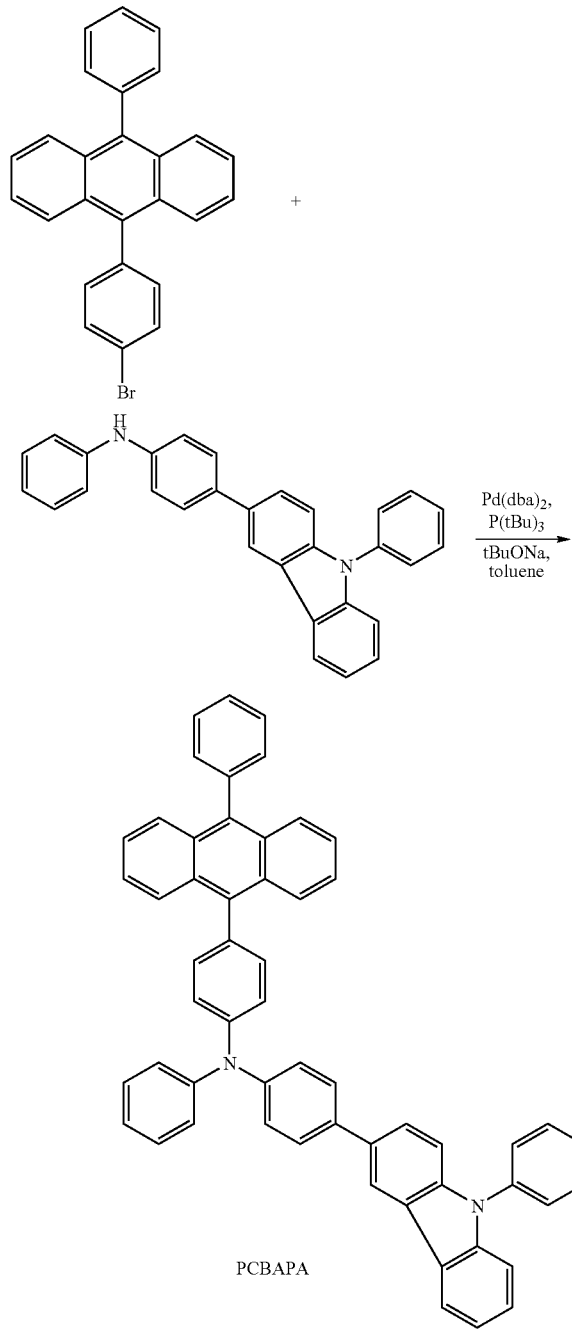

PCBAPA

In this step, first, in a 300 mL three neck flask were put 7.8 g (12 mmol) of 9-(4-bromophenyl)-10-phenylanthracene, 4.8 g (12 mmol) of PCBA, and 5.2 g (52 mmol) of sodium tert-butoxide. The atmosphere in the flask was replaced with nitrogen. To the mixture were added 60 mL of toluene and 0.30 mL of a solution of tri(tert-butyl)phosphine (10 wt %) in hexane. Under reduced pressure, this mixture was degassed while being stirred. After that, 136 mg (0.24 mmol) of bis (dibenzylideneacetone)palladium(0) was added to the mixture.

The mixture was stirred at 100° C. for 3 hours. Then, about 50 mL of toluene was added to this mixture, followed by suction filtration through Celite (manufactured by Wako Pure Chemical Industries, Ltd., Catalog No. 531-16855), alumina, and Florisil (manufactured by Wako Pure Chemical Industries, Ltd., Catalog No. 540-00135). The resulting filtrate was concentrated to give a yellow solid. This solid was recrystallized with a mixed solvent of toluene and hexane to give the desired substance as 6.6 g of a light yellow powder of PCBAPA in a yield of 75%.

The solid obtained by the above Third Step was measured by a nuclear magnetic resonance (NMR) method. The measurement data obtained by $^1$H NMR are described below. The measurement results indicate that PCBAPA was obtained. $^1$H NMR (CDCl$_3$, 300 MHz):δ=7.09-7.14 (m, 1H), 7.28-7.72 (m, 33H), 7.88 (d, J=8.4 Hz, 2H), 8.19 (d, J=7.2 Hz, 1H), 8.37 (d, J=1.5 Hz, 1H)

This application is based on Japanese Patent Application serial no. 2008-240299 filed with Japan Patent Office on Sep. 19, 2008, the entire contents of which are hereby incorporated by reference.

What is claimed is:

1. A method for producing a carbazole derivative represented by General Formula (1) comprising:

coupling 9-[4-(10-phenyl-9-anthryl)phenyl]-9H-carbazole having an active site at the 3-position of the carbazole skeleton with an aromatic compound having an active site,

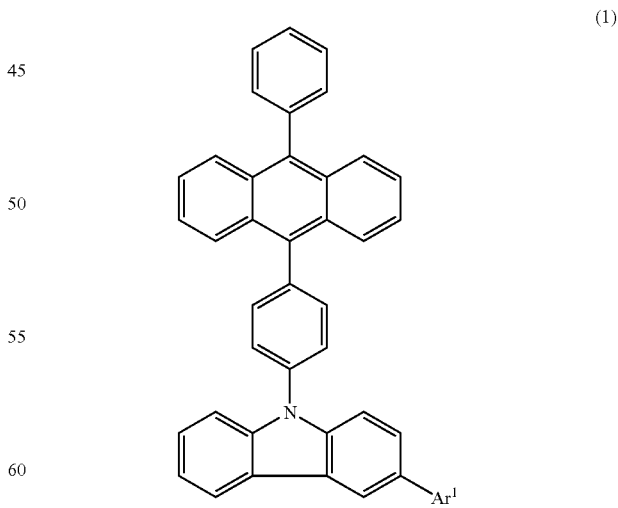

(1)

wherein Ar$^1$ represents an aryl group with 6 to 13 carbon atoms in a ring, wherein the aromatic compound is represented by Compound (A2), and

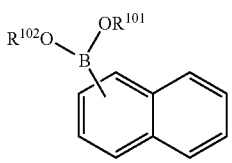

(A2)

wherein $R^{101}$ and $R^{102}$ independently represent hydrogen or an alkyl group having 1 to 6 carbon atoms.

2. The method according to claim 1,
wherein the coupling is carried out using a palladium catalyst.

3. A method for producing a carbazole derivative represented by General Formula (1) comprising:
forming 9-[4-(10-phenyl-9-anthryl)phenyl]-9H-carbazole having an active site at the 3-position: and
coupling the 9-[4-(10-phenyl-9-anthryl)phenyl]-9H-carbazole having the active site at the 3-position of the carbazole skeleton with an aromatic compound having an active site,

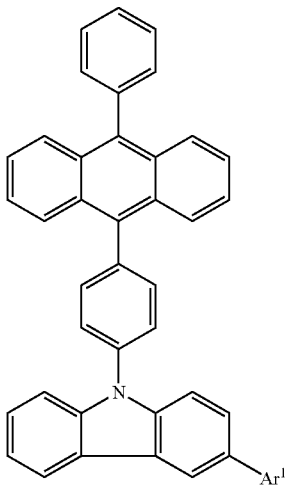

(1)

wherein $Ar^1$ represents an aryl group with 6 to 13 carbon atoms in a ring,
wherein the aromatic compound is represented by Compound (A2), and

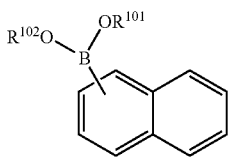

(A2)

wherein $R^{101}$ and $R^{102}$ independently represent hydrogen or an alkyl group having 1 to 6 carbon atoms.

4. The method according to claim 3,
wherein the coupling is carried out using a palladium catalyst.

5. The method according to claim 1,
wherein the active site of the 9-[4-(10-phenyl-9-anthryl)phenyl]-9H-carbazole is any one of halogen group, boronic acid group, boronic ester group, trifluoromethanesulfonic acid group, and thiocyanate group.

6. The method according to claim 1,
wherein the active site of the 9-[4-(10-phenyl-9-anthryl)phenyl]-9H-carbazole is one of halogen or triflate.

7. A method for producing a carbazole derivative represented by General Formula (1) comprising:
halogenating the 3-position of the carbazole skeleton of 9-[4-(10-phenyl-9-anthryl)phenyl]-9H-carbazole: and
coupling the halogenated 9-[4-(10-phenyl-9-anthryl)phenyl]-9H-carbazole with an aromatic compound having an active site,

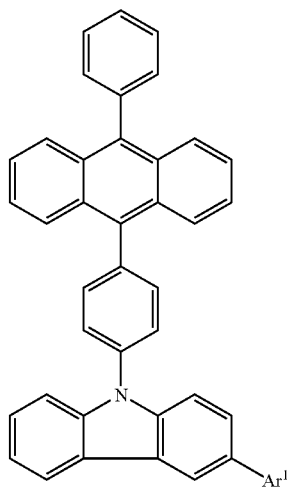

(1)

wherein $Ar^1$ represents an aryl group with 6 to 13 carbon atoms in a ring,
wherein the aromatic compound is represented by Compound (A2), and

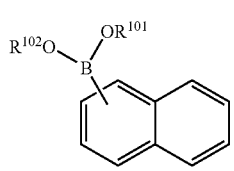

(A2)

wherein $R^{101}$ and $R^{102}$ independently represent hydrogen or an alkyl group having 1 to 6 carbon atoms.

8. The method according to claim 7, wherein the step of halogenation is performed by using iodine or bromine.

9. The method according to claim 7,
wherein the halogenation is bromination, and
wherein the bromination is carried out using a brominating agent.

10. The method according to claim 9, wherein the brominating agent includes bromine or N-bromosuccinimide.

11. The method according to claim 9, wherein a solvent for the bromination is chloroform or carbon tetrachloride.

12. The method according to claim 9, wherein a solvent for the bromination is one selected from the group consisting of ethyl acetate, tetrahydrofuran, dimethylformamide, acetic acid, and water.

13. The method according to claim 7,
wherein the halogenation is iodination, and
wherein the iodination is carried out using a iodinating agent.

14. The method according to claim 13, wherein the iodinating agent is one of selected from the group consisting of N-iodosuccinimide, 1,3-diiodo-5,5-dimethylimidazolidine-2,4-dione, 2,4,6,8-tetraiodo-2,4,6,8-tetraazabicyclo[3,3,0]octane-3,7-dione, and 2-iodo-2,4,6,8-tetraazabicyclo[3,3,0]octane-3,7-dione.

15. The method according to claim 13, wherein a solvent for the iodination is at least one selected from the group consisting of aromatic hydrocarbon, ether, saturated hydrocarbon, halogen, nitrile, ester, acetic acid, and water.

16. The method according to claim 7,
wherein the coupling is carried out using a palladium catalyst.

17. The method according to claim 3, wherein the active site of the 9-[4-(10-phenyl-9-anthryl)phenyl]-9H carbazole is an organotin group, a magnesium halide group, an organozinc group or an organozirconium group.

18. A method for producing a carbazole derivative represented by General Formula (1) comprising:
coupling 9-[4-(10-phenyl-9-anthryl)phenyl]-9H-carbazole having an active site at the 3-position of the carbazole skeleton with an aromatic compound having an active site,

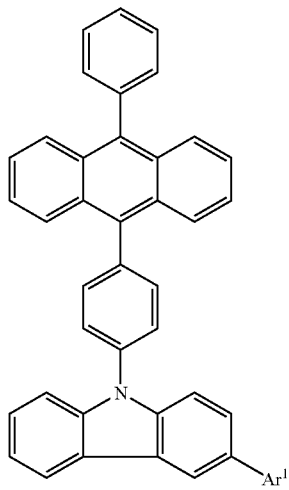

(1)

wherein Ar¹ represents an aryl group with 6 to 13 carbon atoms in a ring,
wherein the aromatic compound is one selected from the group consisting of

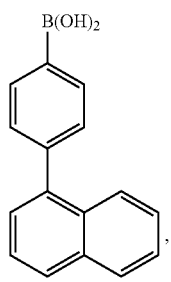

,

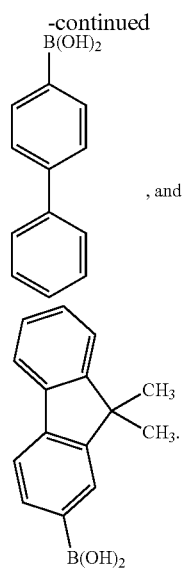

, and

19. The method according to claim 18,
wherein the coupling is carried out using a palladium catalyst.

20. A method for producing a carbazole derivative represented by General Formula (1) comprising:
forming 9-[4-(10-phenyl-9-anthryl)phenyl]-9H-carbazole having an active site at the 3-position: and
coupling the 9-[4-(10-phenyl-9-anthryl)phenyl]-9H-carbazole having the active site at the 3-position of the carbazole skeleton with an aromatic compound having an active site,

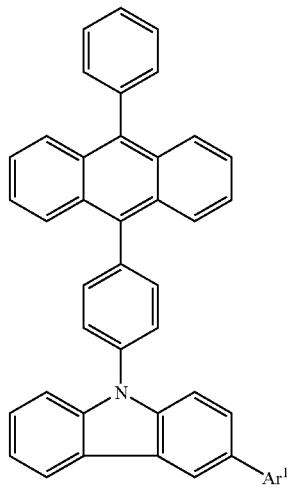

(1)

wherein Ar¹ represents an aryl group with 6 to 13 carbon atoms in a ring,
wherein the aromatic compound is one selected from the group consisting of

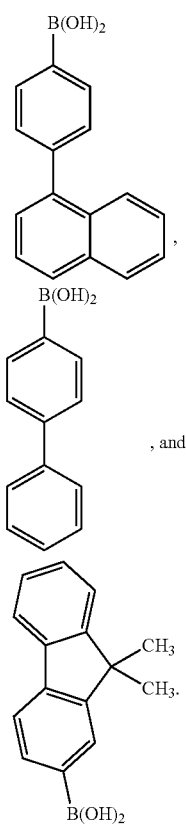
, and

21. The method according to claim 20, wherein the 9-[4-(10-phenyl-9-anthryl)phenyl]-9H-carbazole having the active site at the 3-position is formed by halogenating the 3-position of the carbazole skeleton of 9-[4-(10-phenyl-9-anthryl)phenyl]-9H-carbazole.

22. The method according to claim 21, wherein the step of halogenation is performed by using iodine or bromine.

23. The method according to claim 21,
wherein the halogenation is bromination, and
wherein the bromination is carried out using a brominating agent.

24. The method according to claim 23, wherein the brominating agent includes bromine or N-bromosuccinimide.

25. The method according to claim 23, wherein a solvent for the bromination is chloroform or carbon tetrachloride.

26. The method according to claim 23, wherein a solvent for the bromination is one selected from the group consisting of ethyl acetate, tetrahydrofuran, dimethylformamide, acetic acid, and water.

27. The method according to claim 21,
wherein the halogenation is iodination, and
wherein the iodination is carried out using a iodinating agent.

28. The method according to claim 27, wherein the iodinating agent is one of selected from the group consisting of N-iodosuccinimide, 1,3-diiodo-5,5-dimethylimidazolidine-2,4-dione, 2,4,6,8-tetraiodo-2,4,6,8-tetraazabicyclo[3,3,0]octane-3,7-dione, and 2-iodo-2,4,6,8-tetraazabicyclo[3,3,0]octane-3,7-dione.

29. The method according to claim 27, wherein a solvent for the iodination is at least one selected from the group consisting of aromatic hydrocarbon, ether, saturated hydrocarbon, halogen, nitrile, ester, acetic acid, and water.

30. The method according to claim 20,
wherein the coupling is carried out using a palladium catalyst.

31. The method according to claim 20,
wherein the active site of the 9-[4-(10-phenyl-9-anthryl)phenyl]-9H-carbazole is any one of halogen group, boronic acid group, boronic ester group, trifluoromethanesulfonic acid group, and thiocyanate group.

32. The method according to claim 20,
wherein the active site of the 9-[4-(10-phenyl-9-anthryl)phenyl]-9H-carbazole is one of halogen or triflate.

33. The method according to claim 20, wherein the active site of the 9-[4-(10-phenyl-9-anthryl)phenyl]-9H carbazole is an organotin group, a magnesium halide group, an organozinc group or an organozirconium group.

* * * * *

UNITED STATES PATENT AND TRADEMARK OFFICE
CERTIFICATE OF CORRECTION

PATENT NO.       : 8,669,373 B2
APPLICATION NO.  : 12/560903
DATED            : March 11, 2014
INVENTOR(S)      : Hiroki Suzuki et al.

Page 1 of 1

It is certified that error appears in the above-identified patent and that said Letters Patent is hereby corrected as shown below:

In the Specification:

Column 12, Line 18; Change "CzPAρB." to --CzPApB.--.

Column 37, Lines 57 to 58; Change "tetrazabicyclo" to --tetraazabicyclo--.

Column 42, Line 40; Change ")phenyl]-N,N" to --)phenyl]-N'--.

Column 43, Line 25; Change "Miming" to --forming--.

Column 43, Line 27; Change "thereof; or" to --thereof, or--.

Column 56, Line 51; Change "(PIE" to --(PTE--.

Column 56, Line 55; Change "(RES" to --(RE5--.

Column 66, Line 7; Change "ethanol This" to --ethanol. This--.

Column 68, Line 24; Change "(NNW)" to --(NMR)--.

Column 68, Line 26; Change "CzPAβN)" to --(abbreviation: CzPAβN)--.

Column 70, Line 23; Change "$^1$NMR" to --$^1$H NMR--.

Column 71, Line 42; Change "added. 58 mg" to --added 58 mg--.

Column 74, Line 14; Change "(in, 11H)," to --(m, 11H),--.

Column 75, Line 34; Change "2-[4N-phenyl" to --2-[N-phenyl--.

In the Claims:

Column 83, Line 65, Claim 5; Change "claim 1," to --claim 3,--.

Column 84, Line 3, Claim 6; Change "claim 1," to --claim 3,--.

Signed and Sealed this
Thirtieth Day of September, 2014

Michelle K. Lee
*Deputy Director of the United States Patent and Trademark Office*